United States Patent
Ruben et al.

(10) Patent No.: US 6,433,139 B1
(45) Date of Patent: Aug. 13, 2002

(54) SECRETED PROTEIN HPEAD48

(75) Inventors: Steven M. Ruben, Olney; Craig A. Rosen, Laytonsville; Henrik S. Olsen, Gaithersburg, all of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/288,143

(22) Filed: Apr. 8, 1999

Related U.S. Application Data

(63) Continuation-in-part of application No. PCT/US98/21142, filed on Oct. 8, 1998.
(60) Provisional application No. 60/061,463, filed on Oct. 9, 1997, provisional application No. 60/061,529, filed on Oct. 9, 1997, provisional application No. 60/071,498, filed on Oct. 9, 1997, provisional application No. 60/061,527, filed on Oct. 9, 1997, provisional application No. 60/061,536, filed on Oct. 9, 1997, and provisional application No. 60/061,532, filed on Oct. 9, 1997.

(51) Int. Cl.[7] .................................................. C07K 1/00
(52) U.S. Cl. ....................... 530/350; 530/350; 530/300; 536/23.1; 435/7.1; 435/6
(58) Field of Search .......................... 536/23.1; 530/350, 530/300; 435/6, 7.1

(56) References Cited

PUBLICATIONS

Bischoff et al., "Nucleotide Sequences of *Bacillus subtilis* Flagellar . . . ", J. of Bact., 174(12):4017–4025 (Jun. 1992).
Genbank Accession No. X70772 (Jul. 21, 1995).
Chang et al., "Identification, Characterization, and Sequence . . . ", J. of Vir., 65(6):2884–2894 (Jun. 1991).
Van der Meer et al., "Characterization of the *Lactococcus lactis* . . . ", J. of Bact., 175(9):2578–2588 (May 1993).
Schmuck et al., "Cloning and functional characterization . . . ", FEBS Letters 342:85–90 (1994).
Takeuchi et al., "A Mitotic Role for a Novel . . . ", Mol. Biol. Of the Cell, 4:247–260 (Mar. 1993).
Genbank Accession No. U12702 (Jan. 24, 1995).
Genbank Accession No. AA437293 (May 30, 1997).
Genbank Accession No. AA447438 (Jun. 4, 1997).
Genbank Accession No. AA183135 (Jan. 7, 1997).
Genbank Accession No. B64076 (May 26, 1995).
Genbank Accession No. AA374532 (Apr. 21, 1997).
Genbank Accession No. AA485289 (Aug. 11, 1997).
Genbank Accession No. D80195 (Feb. 9, 1996).
Genbank Accession No. C16143 (Sep. 30, 1996).
Genbank Accession No. AA338221 (Apr. 21, 1997).
Genbank Accession No. AA326904 (Apr. 20, 1997).
Laidler et al., "A SecY Homolog in *Arabidopsis thaliana* ", J. of Biol. Chem., 270(30):17664–17667 (1995).
Warren et al., "Cloning of the cDNA's coding for cat . . . ", Gene, 168:247–249 (1996).
Maucuer et al., "Stathmin Gene Family: Phylogenetic . . . ", J. of Biol. Chem., 268(22):16420–16429 (1993).

*Primary Examiner*—Karen Cochrane Carlson
*Assistant Examiner*—Hope A. Robinson
(74) *Attorney, Agent, or Firm*—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

48 Claims, No Drawings

SECRETED PROTEIN HPEAD48

This application is a continuation-in-part, claiming benefit of priority under 35 U.S.C. §120 of International Application No. PCT/US98/21142, filed Oct. 8, 1998 and published in the English language, which claims benefit under 35 U.S.C. §119(e) based on U.S. Provisional Application Nos. 60/061,463; 60/061,529; 60/071,498; 60/061,527; 60/061,536; and 60/061,532; each of which was filed on Oct. 9, 1997.

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of the coding sequence, but do not comprise all or a portion of any intron. In another embodiment, the nucleic acid comprising the coding sequence does not contain coding sequences of a genomic flanking gene (i.e., 5' or 3' to the gene in the genome).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The strain is being maintained under the Budapest Treaty and will be made available to a patent office signatory to the Budapest Treaty.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA- that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention
Features of Protein Encoded by Gene No: 1

The translation product of this gene shares sequence homology with several human sodium-dependent phosphate transporters (See e.g., Genebank Acc. Nos. gi|2062692 and gi|450532), and a rabbit renal cortical Na/Pa-i-contransporter which is thought to be important in cellular metabolism and kidney function (See Genbank Accession No. gi|165690).

In specific embodiments, polypeptides of the invention comprise the following amino acid sequence: HELG-GLLADFLLSRKILRLITIRKLFTAIGVLFPSVILVSLP WVRSSHSMTMTFLVLSSAISSFCESGALVNFLD IAPRYTGFLKGLLQVFAHIAGAISPTAAGFAAG FFISQDSEFGWRNVFLLSAAVNISGLVFYLIFGRAD VQDWAKEQTFTHL (SEQ ID NO:123); HELGGLLAD-FLLSRKILRLITI (SEQ ID NO:125); RKLFAIGVLFPS-VIL VSLPWVRS (SEQ ID NO:126); SHSMTMTFLVLS-SAISSFCESGAL (SEQ ID NO:127);

VNFLDIAPRYTGFLKGLLQVFAH (SEQ ID NO:128; IAGAISPTAAGFFISQDSEF GWRN (SEQ ID NO:129); VFLLSAAVNISGLVFYLIFGRADVQDWA KEQTFFHL (SEQ ID NO:130); LMKNPAAVGEMAPAMCAKTCNSPLRKPVYRGAISKKLTRAPDSQKLL-MAEDSTKKVMVMLWLD-LTQGRDTRITDGKRTPMAVKSFLMVMSLR IFLERRKSASRPPSSC (SEQ ID NO:124); LMKN-PAAVGEMAPAMCAKTCNSPL RKPV (SEQ ID NO:131); YRGAISKKLTRAPDSQKLLMAED STKKVMVM (SEQ ID NO:132); and/or LWLDLTQGRDTRITDGKRTP-MAVKSFLMVMSLRIFLERR KSASRPPSSC (SEQ ID NO:133). Polynucleotides encoding these polypeptides are also encompassed by the invention.

This gene is expressed primarily in human adult small intestine.

Therefore, polynucleotides and polypeptides of the invention are useful as reagents for differential identification of the tissue(s) or cell type(s) present in a biological sample and for diagnosis of diseases and conditions which include, but are not limited to, renal and gastrointestinal disorders, or other disorders where ion homeostasis is aberrant. Similarly, polypeptides and antibodies directed to these polypeptides are useful in providing immunological probes for differential identification of the tissue(s) or cell type(s). For a number of disorders of the above tissues or cells, particularly of the renal system, expression of this gene at significantly higher or lower levels may be routinely detected in certain tissues or cell types (e.g., renal, neural, gastrointestinal, and cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 67 as residues: Thr-27 to Arg-45.

The tissue distribution in small intestine combined with the homology to a family of Sodium-dependent phosphate transporters suggests that polynucleotides and polypeptides corresponding to this gene are useful for the study, diagnosis and treatment of renal and gastrointestinal disorders and/or diseases. The protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 666 of SEQ ID NO:11, b is an integer of 15 to 680, where both a and b correspond to the positions of nucleotide residues shown in SEQ ID NO:11, and where b is greater than or equal to a+14.

Features of Protein Encoded by Gene No: 2

The translation product of this gene shares sequence homology with several members of a recently described subfamily of P-type ATPases, these ATPases are thought to play a general role in ATP-dependent aminophospholipid transport. Members of this subfamily include, the human FIC1 PROTEIN (see Genbank Accession No. gi|3628757) which is thought to play an essential role in enterohepatic circulation of bile acids, as it's deletion has been linked to Cholestasis, or impaired bile flow. Other members include, the putative E1–E2 ATPase from Mus musculus, which is thought to be important in phagocytosis, blood clotting, and cellular metabolism (See Genbank Accession No.gi|2895095 (AF011337)), and Bovine and Murine chromaffin granule ATPase II homologs (see Genbank Accession No. gi|4115341 and gi|1663648).

In specific embodiments, polypeptides of the invention comprise the following amino acid sequence: EYSTP-DTVHLRKTILFSVKVPVLSEKMY-CICPKSSVMFRARHCSCESVSSSYNCM-SWLMKYTWHALTISMEXYKEMGSKPAELYHVKNE LTAAVTGDKELPSDLGT (SEQ ID NO:134); NQG-SAEQQWAPLQAXKLERQ (SEQ ID NO:135); YSSAG-FDPISLYXSIEIVKACQVYFINQDMQLYDEE TDSQLQCRALNITEDLGQIQYIFSDKTGTLTENKMV FRRCTVSGVEYSHDANEGLLRDAQWSTR-LAGSISISFSGLLTGPCCFDSAPCLCLKF (SEQ ID NO:137); YSSAGFDPISLYXSIEIVKAC QVYFI (SEQ ID NO:138); NQDMQLYDEETDSQLQCRALNITEDL (SEQ ID NO:139); GQIQYIFSDKTGTLTENKMVFRRCTVSG (SEQ ID NO:140); VEYSHD ANEGLLRDAQWSTRLAG-SISIS (SEQ ID NO:141); FSGLLTGPCCFDSAPCLCL KF (SEQ ID NO:142); and/or IRHETLRNTDAXXGIVIY-AGHETKALLNNSGPRY KRXSWRGR (SEQ ID NO:136). Polynucleotides encoding these polypeptides are also encompassed by the invention.

The gene encoding the disclosed cDNA is believed to reside on chromosome 15. Accordingly, polynucleotides related to this invention are useful as a marker in linkage analysis for chromosome 15.

This gene is expressed primarily in human prostate.

Therefore, polynucleotides and polypeptides of the invention are useful as reagents for differential identification of the tissue(s) or cell type(s) present in a biological sample and for diagnosis of diseases and conditions which include, but are not limited to, reproductive or cellular metabolism disorders. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., immune, reproductive, and cancerous and wounded tissues)

or bodily fluids (e.g., lymph, seminal fluid, serum, plasma, urine, synovial fluid and spinal fluid) or another tissue or cell samples taken from an individual having such a disorder, relative to the standard gene expression level, i.e., the expression level in healthy tissue or bodily fluid from an individual not having the disorder.

The tissue distribution in prostate tissue combined with the homology to members of a conserved subfamily of P-type ATPases suggests that polynucleotides and polypeptides corresponding to this gene are useful for treatment and diagnosis of reproductive, metabolic, or haemopoietic disorders, such as congenital afflictions or proliferative conditions, including cancers. The expression in the prostate tissue may indicate the gene or its products can be used in disorders of the prostate, including inflammatory disorders, such as chronic prostatitis, granulomatous prostatitis and malacoplakia, prostatic hyperplasia and prostate neoplastic disorders, including adenocarcinoma, transitional cell carcinomas, ductal carcinomas, squamous cell carcinomas, or as hormones or factors with systemic or reproductive functions. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 727 of SEQ ID NO:12, b is an integer of 15 to 741, where both a and b correspond to the positions of nucleotide residues shown in SEQ ID NO:12, and where b is greater than or equal to a+14.

Features of Protein Encoded by Gene No: 3

In specific embodiments, polypeptides of the invention comprise the following amino acid sequence: HELGPV-CLHAIMLAELIFLFRSLHGILASAGTIGAVAAWL (SEQ ID NO:143). Polynucleotides encoding these polypeptides are also encompassed by the invention.

This gene is expressed primarily in human testes.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly of the testes. Similarly, polypeptides and antibodies directed to these polypeptides are useful in providing immunological probes for differential identification of the tissue(s) or cell type(s). For a number of disorders of the above tissues or cells, particularly of the male reproductive system, expression of this gene at significantly higher or lower levels may be routinely detected in certain tissues or cell types (e.g., reproductive, testes, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 69 as residues: Glu-32 to Asn-54, His-98 to Arg-106, Ser-126 to Ser-134.

The tissue distribution in testes suggests that polynucleotides and polypeptides corresponding to this gene are useful for the diagnosis and treatment of various reproductive or endocrine disorders, such as male infertility and hormone imbalances. Similarly, the tissue distribution in testes indicates that the protein product of this clone is useful for the treatment and diagnosis of conditions concerning normal testicular function (e.g., endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents.

The secreted protein may also be used as a contraceptive. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 605 of SEQ ID NO:13, b is an integer of 15 to 619, where both a and b correspond to the positions of nucleotide residues shown in SEQ ID NO:13, and where b is greater than or equal to a+14.

Features of Protein Encoded by Gene No: 4

The translation product of this clone has been shown to have homology to the Y isoform of the conserved ubiquitous human TPR motif which is thought to be important in maintaining cellular metabolism in addition to a possible connection in increasing an individual's susceptibility to male infertility (See Genbank Accession No.gi|2580574 (AF000994)). In addition, the translation product of this clone shows homology to the murine male-specific histocompatibility antigen H-YDb (See Genbank Accession No. gnl|PID|e300472) from which is derived an epitope of the complex male-specific transplantation antigen H-Y.

In specific embodiments, polypeptides of the invention comprise the following amino acid sequence: DFGTXSD-PKLFEMIKYCLLKILKQYQTLREALVAAGKEVIWH GRTNDEPAHYCSICEVEVFNLLFVTNESNTQKT YIVHCHDCARKTSKSLENFVVLEQYKMEDLIQVY DQFTLASPWPPMDQSAFTSSLLRPIKALGSGR AEQTSGDQLQKGATHSRASSLLRAAEMTRRPAS REELPDPGLFCHSIKLLFVLL (SEQ ID NO:144); DFGTXSDPKLFEMIKYCLLKILKQYQ (SEQ ID NO:145); TLREALVAAGKEVIWHGRTNDEPAHYCS (SEQ ID NO:146); ICEVEVFNLLFVTNESNTQK-TYIVHC (SEQ ID NO:147); HDCARKTSKSLENFVV-LEQYKMEDLIQVYD (SEQ ID NO:148); QFTLASPW-PPMDQSAFTSSLLRPIKALGSG (SEQ ID NO:149); RAEQTSGDQLQKGATHSRASSLLRAAEMT (SEQ ID NO:150); and/or RRPASREELPDPGLFCHSIKLLFVLL (SEQ ID NO:151). Polynucleotides encoding these polypeptides are also encompassed by the invention.

This gene is expressed primarily in activated human neutrophils and synovium.

Therefore, polynucleotides and polypeptides of the invention are useful as reagents for differential identification of the tissue(s) or cell type(s) present in a biological sample and for diagnosis of diseases and conditions which include, but are not limited to, immune or hematopoieitic disorders, particularly inflammatory conditions, and/or autoimmune disorders, such as arthritis. Similarly, polypeptides and antibodies directed to these polypeptides are useful in providing immunological probes for differential identification of the tissue(s) or cell type(s). For a number of disorders of the above tissues or cells, particularly of the inflammatory and immune systems, expression of this gene at significantly higher or lower levels may be routinely detected in certain tissues or cell types (e.g., immune, skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils and synovium, in addition to the homology of the translated product of this clone to a murine male-specific histocompatibility antigen, suggests that polynucleotides and polypeptides corresponding to this gene are useful for the study, diagnosis, and treatment of inflammatory and immune disorders. Moreover, the protein may be useful for the detection and/or treatment of disorders and conditions afflicting the skeletal system, in particular osteoporosis, bone cancer, connective tissue disorders, (e.g., arthritis, trauma, tendonitis, chrondomalacia and inflammation). The protein is also useful in the diagnosis or treatment of various autoimmune disorders such as rheumatoid arthritis, lupus, scleroderma, and dermatomyositis, dwarfism, spinal deformation, joint abnormalities, and chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 597 of SEQ ID NO:14, b is an integer of 15 to 611, where both a and b correspond to the positions of nucleotide residues shown in SEQ ID NO:14, and where b is greater than or equal to a+14.

Features of Protein Encoded by Gene No: 5

In specific embodiments, polypeptides of the invention comprise the following amino acid sequence: LPGNFRP-PRVILTFQWRFYLSFRKL (SEQ ID NO:152); XIPPXX-LPGNFRPPRVWLTFQWRFYLSFRKL (SEQ ID NO:154); and/or YLLLPCGLLSFWMCGALV-VSPFVQNGQGQRLREARSLCLLKGTTWI-FLMLSLPHFLVQELKFSNNFFSTV-VIFSTSGFLQPTLIFLKLSWKSTHL (SEQ ID NO:153). Polynucleotides encoding these polypeptides are also encompassed by the invention.

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly inflammatory or immunodeficiency conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid, and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 71 as residues: Thr-32 to Leu-43.

The tissue distribution in T-cells suggests that polynucleotides and polypeptides corresponding to this gene are useful for the study and treatment of immune defects. More specifically, the gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 571 of SEQ ID NO:15, b is an integer of 15 to 585, where both a and b correspond to the positions of nucleotide residues shown in SEQ ID NO:15, and where b is greater than or equal to a+14.

Features of Protein Encoded by Gene No: 6

In specific embodiments, polypeptides of the invention comprise the following amino acid sequence: YMMVHCK- YSVYNLLNKWIGFSIFPHWTWIDLEIG-
GLNQVEIKGPNNCRVAGEG RYKCSKGGSR (SEQ ID NO:155). Polynucleotides encoding these polypeptides are also encompassed by the invention.

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune and hemopoietic disorders, particularly inflammatory or immunodeficiency conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells suggests that polynucleotides and polypeptides corresponding to this gene are useful for the study and treatment of inflammation, and other immune and hematopoietic disorders. Specifically, the gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1026 of SEQ ID NO:16, b is an integer of 15 to 1040, where both a and b correspond to the positions of nucleotide residues shown in SEQ ID NO:16, and where b is greater than or equal to a+14.

Features of Protein Encoded by Gene No: 7

When tested against U937 Myeloid cell lines, supernatants removed from cells containing this gene activated the GAS assay. Thus, it is likely that this gene activates myeloid cells through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

In specific embodiments, polypeptides of the invention comprise the following amino acid sequence: MSAALW-TYMRFLACLNHSSGSMYLSVNSTPV-LLLLLVPNSARARAEFLQPGGXTSS-RAAXXAVELQLLFPLXXG (SEQ ID NO:156); FRQARNLMYVHNAADIHSS-LPQHITVISPRELCHTFSLLKPATLDLLCSLSVGN LFRISERQCKH (SEQ ID NO:157); and/or RVNVSSIM-DIHEVPGLSKSQLWFNVPVC-QLHTCVAVAARAEFGTSSCRIPAARGXH (SEQ ID NO:158). Polynucleotides encoding these polypeptides are also encompassed by the invention.

This gene is expressed primarily in prostate cancer.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particular prostate cancer or infertility. Similarly, polypeptides and antibodies directed to these polypeptides are useful in providing immunological probes for differential identification of the tissue(s) or cell type(s). For a number of disorders of the above tissues or cells, particularly of the prostate, especially of the reproductive system, expression of this gene at significantly higher or lower levels may be routinely detected in certain tissues or cell types (e.g., reproductive, prostate, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 73 as residues: Gln-51 to Thr-61, Ser-65 to Thr-71, Pro-85 to Gln-91.

The tissue distribution in prostate cancer, along with activation of the GAS assay when supernatants of cells containing this gene were tested against U937 Myeloid cell lines, suggests that polynucleotides and polypeptides corresponding to this gene are useful for the treatment and diagnosis of disorders of the reproductive system, particular proliferative conditions such as cancer. Similarly, the gene or its products can be used in the disorders of the prostate, including inflammatory disorders, such as chronic prostatitis, granulomatous prostatitis and malacoplakia, prostatic hyperplasia and prostate neoplastic disorders, including adenocarcinoma, transitional cell carcinomas, ductal carcinomas, squamous cell carcinomas, or as hormones or factors with systemic or reproductive functions. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 611 of SEQ ID NO:17, b is an integer of 15 to 625, where both a and b correspond to the positions of nucleotide residues shown in SEQ ID NO:17, and where b is greater than or equal to a+14.

Features of Protein Encoded by Gene No: 8

In specific embodiments, polypeptides of the invention comprise the following amino acid sequence: IRHEGNSCT-NKTAHAVLTASYTECSC (SEQ ID NO:159). Polynucleotides encoding these polypeptides are also encompassed by the invention.

This gene is expressed primarily in prostate.

Therefore, polynucleotides and polypeptides of the invention are useful as reagents for differential identification of the tissue(s) or cell type(s) present in a biological sample and for diagnosis of diseases and conditions which include, but are not limited to, disorders of the reproductive system, particularly cancer. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, prostate, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in prostate suggests that polynucleotides and polypeptides corresponding to this gene are useful for treatment and diagnosis of disorders of the reproductive system, such as proliferative conditions, including, but not limited to, prostate cancer. Similarly, the gene or its products can be used in the treatment of disorders of the prostate, including inflammatory disorders, such as chronic prostatitis, granulomatous prostatitis and malacoplakia, prostatic hyperplasia and prostate neoplastic disorders, including adenocarcinoma, transitional cell carcinomas, ductal carcinomas, squamous cell carcinomas, or as hormones or factors with systemic or reproductive functions. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 805 of SEQ ID NO:18, b is an integer of 15 to 819, where both a and b correspond to the positions of nucleotide residues shown in SEQ ID NO:18, and where b is greater than or equal to a+14.

Features of Protein Encoded by Gene No: 9

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune and blood disorders, particularly inflammatory or immunodeficiency conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoeitic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells suggests that polynucleotides and polypeptides corresponding to this gene are useful for the study and treatment of immune and inflammatory disorders. Moreover, the gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 768 of SEQ ID NO:19, b is an integer of 15 to 782, where both a and b correspond to the positions of nucleotide residues shown in SEQ ID NO:19, and where b is greater than or equal to a+14.

Features of Protein Encoded by Gene No: 10

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells suggests that polynucleotides and polypeptides corresponding to this gene are useful for the study and treatment of immune and blood disorders. Moreover, this gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity, immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues.

In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 641 of SEQ ID NO:20, b is an integer of 15 to 655, where both a and b correspond to the positions of nucleotide residues shown in SEQ ID NO:20, and where b is greater than or equal to a+14.

Features of Protein Encoded by Gene No: 11

When tested against K562 cell lines, supernatants removed from cells containing this gene activated the ISRE (interferon-sensitive responsive element) pathway. Thus, it is likely that this gene activates leukemia cells, and to a lesser extent, in immune and hematopoietic cells and tissues, through the Jak-STAT signal transduction pathway. ISRE is a promoter element found upstream in many genes which are involved in the Jak-STAT pathway. The Jak-STAT pathway is a large, signal transduction pathway involved in the differentiation and proliferation of cells. Therefore, activation of the Jak-STAT pathway, reflected by the binding of the ISRE element, can be used to indicate proteins involved in the proliferation and differentiation of cells.

This gene is expressed primarily in smooth muscle.

Therefore, polynucleotides and polypeptides of the invention are useful as reagents for differential identification of the tissue(s) or cell type(s) present in a biological sample and for diagnosis of diseases and conditions which include, but are not limited to, vascular disorders, particularly microvascular disease, atherosclerosis, aneurysm, and stroke. Similarly, polypeptides and antibodies directed to these polypeptides are useful in providing immunological probes for differential identification of the tissue(s) or cell type(s). For a number of disorders of the above tissues or cells, particularly of the vascular and smooth muscle tissues, expression of this gene at significantly higher or lower levels may be routinely detected in certain tissues or cell types (e.g, vascular tissue, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in smooth muscle, combined with the detected ISRE biological activity, suggests that polynucleotides and polypeptides corresponding to this gene are useful for the study, diagnosis, and treatment of vascular disorders. The protein product of this gene is useful for the diagnosis and treatment of conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 784 of SEQ ID NO:21, b is an integer of 15 to 798, where both a and b correspond to the positions of nucleotide residues shown in SEQ ID NO:21, and where b is greater than or equal to a+14.

Features of Protein Encoded by Gene No: 12

The translation product of this gene shares sequence homology with the human IL-8 receptor (PF4AR), which is thought to be important in inflammatory disorders.

This gene is expressed primarily in synovial sarcoma.

Therefore, polynucleotides and polypeptides of the invention are useful as reagents for differential identification of the tissue(s) or cell type(s) present in a biological sample and for diagnosis of diseases and conditions which include, but are not limited to, inflammatory disorders such as rheumatoid arthritis. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 78 as residues: Thr-17 to Leu-22.

The tissue distribution in synovial sarcoma, combined with the homology to an IL-8 receptor (PF4AR), suggests that polynucleotides and polypeptides corresponding to this gene are useful for the diagnosis and treatment of inflammatory disorders such as rheumatoid arthritis. Similarly, this gene product may also be useful for the detection and treatment of osteoporosis, bone cancer, as well as, disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid).

The secreted protein can also be used to determine biological activity, to raise antibodies, as tissue markers, to isolate cognate ligands or receptors, to identify agents that modulate their interactions, and as nutritional supplements. It may also have a very wide range of biological activities. Typical of these are cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating hemophilia, cardiac infarction etc.); anti-inflammatory activity (e.g. for treating septic shock, Crohn's disease); as antimicrobials; for treating psoriasis or other hyperproliferative diseases; for regulation of metabolism, and behavior. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 632 of SEQ ID NO:22, b is an integer of 15 to 646, where both a and b correspond to the positions of nucleotide residues shown in SEQ ID NO:22, and where b is greater than or equal to a+14.

Features of Protein Encoded by Gene No: 13

When tested against PC12 cell lines, supernatants removed from cells containing this gene activated the EGR1 (early growth response gene 1) promoter element. Thus, it is likely that this gene activates sensory neuron cells, and to a lesser extent, in neural cells and tissues, through the EGR1 signal transduction pathway. EGR1 is a separate signal transduction pathway from Jak-STAT. Genes containing the EGR1 promoter element are induced in various tissues and cell types upon activation, leading the cells to undergo differentiation and proliferation.

This gene is expressed primarily in human testes.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly afflictions of the testes, such as male infertility and testicular cancer. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, testes, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 79 as residues: Glu-33 to Arg-45.

The tissue distribution in testes combined with the detected EGR1 biological activity suggests that polynucleotides and polypeptides corresponding to this gene are useful for various reproductive disorders such as male infertility or associated endocrine disorders. Similarly, the protein product of this clone is useful for the treatment and diagnosis of conditions concerning proper testicular function (e.g., endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 738 of SEQ ID NO:23, b is an integer of 15 to 752, where both a and b correspond to the positions of nucleotide residues shown in SEQ ID NO:23, and where b is greater than or equal to a+14.

Features of Protein Encoded by Gene No: 14

In specific embodiments, polypeptides of the invention comprise the following amino acid sequence: YKVV-LVWREDQSSHKIHLSQTLIQNKALTLFNSMK AERGEEAXGKNVSS(SEQ ID NO:160); YKVV-LVWREDQSSHKIHLSQTLIQ (SEQ ID NO:162); NKALTLFNSMKAERGEEAXGKNVSS (SEQ ID NO:163); DGELSKCCMCSDYTIDCYFPIS-LPLLGRPYYLRHNIEIRPYINHTMAS KGSSKRMGCTSFTLTQKLEIIILSEKGM-WKAEIGQKLGXLHHS (SEQ ID NO:161); DGELSKCC-MCSDYTIDCYFPISLPLLGRPYY (SEQ ID NO:164); LRHNIEIRPYINHTMASKGSSKRMGCTSFTLT (SEQ ID NO:165); and/or QKLEIIILSEKGMWKAEIGQKLGXL-HHS (SEQ ID NO:166). Polynucleotides encoding these polypeptides are also encompassed by the invention.

This gene is expressed primarily in fetal bone and testical tumors.

Therefore, polynucleotides and polypeptides of the invention are useful as reagents for differential identification of the tissue(s) or cell type(s) present in a biological sample and for diagnosis of diseases and conditions which include, but are not limited to, developmental, skeletal, or reproductive disorders, particularly, proliferative conditions such as testicular cancer. Similarly, polypeptides and antibodies directed to these polypeptides are useful in providing immunological probes for differential identification of the tissue(s) or cell type(s). For a number of disorders of the above tissues or cells, particularly of the male reproductive systems, expression of this gene at significantly higher or lower levels may be routinely detected in certain tissues or cell types (e.g., reproductive, skeletal, testes, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in testes suggests that polynucleotides and polypeptides corresponding to this gene are useful for the diagnosis and treatment of testicular cancer. In addition, expression of this gene product in the testis may implicate this gene product in normal testicular function. In addition, this gene product may be useful in the treatment of male infertility, and/or could be used as a male contraceptive.

Moreover, this gene product may be useful in the detection and treatment of disorders and conditions afflicting the skeletal system, in particular osteoporosis, bone cancer, as well as, disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphysial dysplasia congenital familial osteoarthritis, Atelosteogenesis type II, metaphysial chondrodysplasia type Schmid).

Expression within fetal tissue and other cellular sources marked by proliferating cells suggests that this protein may play a role in the regulation of cellular division, and may show utility in the diagnosis and treatment of cancer and other proliferative disorders. Similarly, developmental tissues rely on decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 801 of SEQ ID NO:24, b is an integer of 15 to 815, where both a and b correspond to the positions of nucleotide residues shown in SEQ ID NO:24, and where b is greater than or equal to a+14.

Features of Protein Encoded by Gene No: 15

This gene is expressed primarily in stomach.

Therefore, polynucleotides and polypeptides of the invention are useful as reagents for differential identification of the tissue(s) or cell type(s) present in a biological sample and for diagnosis of diseases and conditions which include, but are not limited to, gastrointestinal and digestive disorders. Similarly, polypeptides and antibodies directed to these polypeptides are useful in providing immunological probes for differential identification of the tissue(s) or cell type(s). For a number of disorders of the above tissues or cells, particularly of the gastrointestinal system, expression of this gene at significantly higher or lower levels may be routinely detected in certain tissues or cell types (e.g., gastrointestinal, stomach, and cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 81 as residues: Ser-14 to Gln-23, Pro-32 to Lys-39.

The tissue distribution in stomach tissue suggests that polynucleotides and polypeptides corresponding to this gene are useful for the study and treatment of gastrointestinal, digestive, and general metabolic disorders. For example, the protein product of this clone may be useful for the diagnosis, prevention, and/or treatment of various metabolic disorders such as Tay-Sach's disease, phenylkenonuria, galactosemia, porphyrias, and Hurler's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 864 of SEQ ID NO:25, b is an integer of 15 to 878, where both a and b correspond to the positions of nucleotide residues shown in SEQ ID NO:25, and where b is greater than or equal to a+14.

Features of Protein Encoded by Gene No: 16

In specific embodiments, polypeptides of the invention comprise the following amino acid sequence: MLCIN-VQTHVYECA (SEQ ID NOP:167). Polynucleotides encoding these polypeptides are also encompassed by the invention.

This gene is expressed primarily in anergic T-cells and CD34 depleted cord blood.

Therefore, polynucleotides and polypeptides of the invention are useful as reagents for differential identification of the tissue(s) or cell type(s) present in a biological sample and for diagnosis of diseases and conditions which include, but are not limited to, hemopoietic, immune, or reproductive conditions. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hemopoietic, immune, or reproductive, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells suggests that polynucleotides and polypeptides corresponding to this gene are useful for the study and treatment of immune, inflammatory and other hematopoietic disorders. In addition, polynucleotides and polypeptides corresponding to this gene are useful for the treatment and diagnosis of hematopoetic related disorders such as anemia, pancytopenia, leukopenia, thrombocytopenia or leukemia since stromal cells are important in the production of cells of hematopoietic lineages.

The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 836 of SEQ ID NO:26, b is an integer of 15 to 850, where both a and b correspond to the positions of nucleotide residues shown in SEQ ID NO:26, and where b is greater than or equal to a+14.

Features of Protein Encoded by Gene No: 17

In specific embodiments, polypeptides of the invention comprise the following amino acid sequence: LCCPG-WSAVVRSWLTATLASWVQAILMDSASQVAGITSVH HQAQLSFVFLVEMGLCHVGQAGLKL-LASSDLPASASQSAGITGMSHHWPERTSFIFKI (SEQ ID NO:168); LCCPGWSAVVRSWLTAT-LASWVQAILMDSASQ (SEQ ID NO:169); VAGITSVHHQAQLSFVFLVEMGLCHVGQAGLKLLA (SEQ ID NO:170); and/or SSDLPASASQSAGITGMSHH-SWPERTSFIFKI (SEQ ID NO:171). Polynucleotides encoding these polypeptides are also encompassed by the invention.

This gene is expressed primarily in human adult small intestine.

Therefore, polynucleotides and polypeptides of the invention are useful as reagents for differential identification of the tissue(s) or cell type(s) present in a biological sample and for diagnosis of diseases and conditions which include, but are not limited to, gastrointestinal disorders. Similarly, polypeptides and antibodies directed to these polypeptides are useful in providing immunological probes for differential identification of the tissue(s) or cell type(s). For a number of disorders of the above tissues or cells, particularly of the gastrointestinal system, expression of this gene at significantly higher or lower levels may be routinely detected in certain tissues or cell types (e.g., gastrointestinal, metabolic, and cancerous and wounded tissues) or bodily fluids (e.g., bile, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in small intestine suggests that polynucleotides and polypeptides corresponding to this gene are useful for the study, diagnosis, and treatment of gastrointestinal disorders, and/or treatment of various metabolic disorders such as Tay-Sachs disease, phenylkenonuria, galactosemia, porphyrias, and Hurler's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 774 of SEQ ID NO:27, b is an integer of 15 to 788, where both a and b correspond to the positions of nucleotide residues shown in SEQ ID NO:27, and where b is greater than or equal to a+14.

Features of Protein Encoded by Gene No: 18

The translation product of this gene was shown to have homology to the F33H2.2 protein from Caenorhabditis elegans (See Genbank Accession No.gnl|PID|e297838). Considering the homology to a *C. elegans* protein, an important and vital function may be attributed to this clone based upon its conservation.

In specific embodiments, polypeptides of the invention comprise the following amino acid sequence: FGRGNTIL-FLRHNKDLVAQTAQPDQPNYGFPLDLL-RCESLLGLDPATCSRVLNKNYTLLVSMA-PLTNEIRPVSSCTPQHIGPAIPEVSSVWFKLYIYHVTGQ GPPSLLLSKGTRLRKLPDIFQSYDRLX-ITSWGHDPGVVPTSNVLTMLNDALTH- SAVLIQGHGLHGIGETVHVPFPFDE-
TELQGEFTRVNMGVHKALQILRNRVXLQHLCGYV
TMLNASSQLADRKLSDASDERGEPDLASGSDVNGST
ESFEMVEEATIDSATKQTSGATTEADWVP LV (SEQ ID
NO:172); FGRGNTILFLRHNKDLVAQTAQPDQP-
NYGFPLDLLRCESLLGLDPATCSRV-
LNKNYTLLVSMAPLTNEIRPVSSCT-
PQHIGPAIPEVSSVWFKLYIYHVTGQGPPSLLLSKGT
RLRKLPDIFQSYDRLXITSWGHDPGV-
VPTSNVLTMLNDALTHSAVLIQGHGLHGIGETVHVP
(SEQ ID NO:173); LRHNKDLVAQTAQPDQPNYGF(SEQ
ID NO: 174); FPLDLLRCESLLGLDPATCSR (SEQ ID
NO: 175); RVLNKNYTLLVSMAPLTNEIR (SEQ ID NO:
176); R PVSSCTPQHIGPAIPEVSS (SEQ ID NO: 177);
SVWFKLYIYHVTGQGPPSLLL (SEQ ID NO: 178);
LSKGTRLRKLPDIFQSYDRLX (SEQ ID NO: 179);
XITSWGHDPGVV PTSNVLTM (SEQ ID NO: 180);
MLNDALTHSAVLIQGHGLHGI(SEQ ID NO: 181); FPF-
DETELQGEFRRVNMGVHKALQILRNRVX-
LQHLCGYVTMLNASSQLADRKLSDAS-
DERGEPDLASGSDVNGSTESEMVIEEATIDSATKQTS
GATTEADWVP LV (SEQ ID NO: 182); GEFRRVN-
MGVHKALQILRNRV (SEQ ID NO: 183); VXLQHL-
CGYVTMLNASSQLA(SEQ ID NO: 184); ADRKLSDAS-
DERGEPDLASGS (SEQ ID NO: 185); LRKLHSQTNPI
(SEQ ID NO: 187); and/or SDVNGSTESFEMVIEEATIDS
(SEQ ID NO: 186). Polynucleotides encoding these
polypeptides are also encompassed by the invention.

This gene is expressed primarily in healing groin wound, and to a lesser extent, in synovium.

Therefore, polynucleotides and polypeptides of the invention are useful as reagents for differential identification of the tissue(s) or cell type(s) present in a biological sample and for diagnosis of diseases and conditions which include, but are not limited to, developmental, wound healing, and synovial disorders. Similarly, polypeptides and antibodies directed to these polypeptides are useful in providing immunological probes for differential identification of the tissue(s) or cell type(s). For a number of disorders of the above tissues or cells, particularly of the synovium and epithelium, expression of this gene at significantly higher or lower levels may be routinely detected in certain tissues or cell types (e.g., developmental, skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 84 as residues: Lys-84 to Lys-90, Phe-151 to Leu-156, Ala-204 to Asp-212, Ala-238 to Ala-245.

The tissue distribution in wounded tissue suggests that polynucleotides and polypeptides corresponding to this gene are useful for the study, diagnosis, and treatment of disorders involving the synovium and epithelium. Specifically, polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. In addition, such disorders may predispose an individual viral and bacterial infections of the skin (i.e. cold sores, warts, chickenpox, molluscum contagiosum, herpes zoster, boils, cellulitis, erysipelas, impetigo, tinea, althletes foot, and ringworm).

Moreover, the protein product of this clone may also be useful for the treatment or diagnosis of various connective tissue disorders such as arthritis, trauma, tendonitis, chrondomalacia and inflammation, autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). The protein is useful in the detection, treatment, and/or prevention of skeletal diseases and disorders, which include, but are not limited to osteoporosis, bone cancer, etc. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 824 of SEQ ID NO:28, b is an integer of 15 to 838, where both a and b correspond to the positions of nucleotide residues shown in SEQ ID NO:28, and where b is greater than or equal to a+14.

Features of Protein Encoded by Gene No: 19

This gene is expressed primarily in ovarian cancer.

Therefore, polynucleotides and polypeptides of the invention are useful as reagents for differential identification of the tissue(s) or cell type(s) present in a biological sample and for diagnosis of diseases and conditions which include, but are not limited to, disorders of the reproductive system, particularly proliferative disorders of the ovary, such as cancer and cysts. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, ovarian tissue, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in ovarian tissue suggests that polynucleotides and polypeptides corresponding to this gene are useful for the treatment and diagnosis of disorders of the reproductive system and cancers. Moreover, the expression within cellular sources marked by proliferating cells (i.e., ovarian cancer tissues) suggests this protein may play a role in the regulation of cellular division, and may show utility in the diagnosis, treatment, and/or prevention of developmental diseases and disorders, cancer, and other proliferative conditions. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 741 of SEQ ID NO:29, b is an integer of 15 to 755, where both a and b correspond to the positions of nucleotide residues shown in SEQ ID NO:29, and where b is greater than or equal to a+14.

Features of Protein Encoded by Gene No: 20

In specific embodiments, polypeptides of the invention comprise the following amino acid sequence: RNFYLYFLPYCVVCVC (SEQ ID NO:188). Polynucleotides encoding these polypeptides are also encompassed by the invention.

This gene is expressed primarily in prostate cancer.

Therefore, polynucleotides and polypeptides of the invention are useful as reagents for differential identification of the tissue(s) or cell type(s) present in a biological sample and for diagnosis of diseases and conditions which include, but are not limited to, reproductive disorders, particularly proliferative conditions of the prostate, such as cancer. Similarly, polypeptides and antibodies directed to these polypeptides are useful in providing immunological probes for differential identification of the tissue(s) or cell type(s). For a number of disorders of the above tissues or cells, particularly of the reproductive disorders and cancer, expression of this gene at significantly higher or lower levels may be routinely detected in certain tissues or cell types (e.g., reproductive, prostate, and cancerous and wounded tissues) or bodily fluids (e.g., lymph, amniotic fluid, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 86 as residues: Lys-16 to Ser-21, Gly-36 to Asp-41.

The tissue distribution in prostate suggests that polynucleotides and polypeptides corresponding to this gene are useful for the treatment and diagnosis of disorders of the reproductive organs and cancers, such as male infertility. Protein may also be useful as a contraceptive. Moreover, the expression within cellular sources marked by proliferating cells (i.e., prostate cancer) suggests this protein may play a role in the regulation of cellular division, and may show utility in the diagnosis, treatment, and/or prevention of developmental diseases and disorders, cancer, and other proliferative conditions. Similarly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Protein, as well as, antibodies directed against the protein may show utility as a tumor marker and/or immunotherapy targets for the above listed tissues. The protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 799 of SEQ ID NO:30, b is an integer of 15 to 813, where both a and b correspond to the positions of nucleotide residues shown in SEQ ID NO:30, and where b is greater than or equal to a+14.

Features of Protein Encoded by Gene No: 21

This gene is expressed primarily in B-cells and rhabdomyosarcoma.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, or muscular disorders, particularly proliferative conditions such as cancer or fibroids. Similarly, polypeptides and antibodies directed to these polypeptides are useful in providing immunological probes for differential identification of the tissue(s) or cell type(s). For a number of disorders of the above tissues or cells, particularly of the haemopoietic and muscular system, expression of this gene at significantly higher or lower levels may be routinely detected in certain tissues or cell types (e.g., immune, hematopoietic, muscular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune and muscle tissues or cells suggests that polynucleotides and polypeptides corresponding to this gene are useful for the treatment and diagnosis of a variety of disorders, such as for the detection, and/or prevention of muscular dystrophy, cardiomyopathy, fibroids, myomas, and rhabdomyosarcomas. This gene product may be involved in the regulation of cytokine production, antigen presentation, or other processes suggesting a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues.

Moreover, the protein may represent a secreted factor that influences the differentiation or behavior of other blood cells, or that recruits hematopoietic cells to sites of injury. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 499 of SEQ ID NO:31, b is an integer of 15 to 513, where both a and b correspond to the positions of nucleotide residues shown in SEQ ID NO:31, and where b is greater than or equal to a+14.

Features of Protein Encoded by Gene No: 22

In specific embodiments, polypeptides of the invention comprise the following amino acid sequence: GTRSINLL-FFRCILEGGKSVEEQLCNSYKFS (SEQ ID NO:189). Polynucleotides encoding these polypeptides are also encompassed by the invention.

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune and blood conditions, particularly inflammatory or immunodeficiency disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells suggests that polynucleotides and polypeptides corresponding to this gene are useful for the study and treatment of inflammation and immune disorders. More specifically, the gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 562 of SEQ ID NO:32, b is an integer of 15 to 576, where both a and b correspond to the positions of nucleotide residues shown in SEQ ID NO:32, and where b is greater than or equal to a+14.

Features of Protein Encoded by Gene No: 23

The translation product of this gene was shown to have homology to the gi|2501808 brain digoxin carrier protein of Rattus norvegicus which is thought to serve the role as a sodium-independent organic anion transporter. This gene may also play a role in hormone transport. When tested against U937 cell lines, supernatants removed from cells containing this gene activated the GAS (gamma activating sequence) promoter element. Thus, it is likely that this gene activates promyelocytic cells, and to a lesser extent in other immune or hematopoietic cells and tissues, through the Jak-STAT signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

In specific embodiments, polypeptides of the invention comprise the following amino acid sequence: LTVPRRC-PAATETNVDGQKVYRDCSCIPQNLSSGF-GHATAGXMHFNLSEKAPPSGFHIRCEFS-LHSXSSIPALTATLRCVRDPQRSFALGIQWIVVRILG GIPGPIAFGWVIDKACLLWQXQCGQXGSCLVYQXRP (SEQ ID NO:190); VSLCHAGALQPRRR (SEQ ID NO:191); ATETNVDGQKVYRDCSCIPQN (SEQ ID NO:192); NLSSGFGHATAGXMHFNLSEK (SEQ ID NO:193); KAPPSGFHIRCEFSLHSXSSI (SEQ ID NO:194); IPALTATLRCVRDPQRSFAL (SEQ ID NO: 195); and/or LGIQWIVVRILGGIPGPIAFG (SEQ ID NO:196). Polynucleotides encoding these polypeptides are also encompassed by the invention.

This gene is expressed primarily in retina.

Therefore, polynucleotides and polypeptides of the invention are useful as reagents for differential identification of the tissue(s) or cell type(s) present in a biological sample and for diagnosis of diseases and conditions which include, but are not limited to, visual disorders. Similarly, polypeptides and antibodies directed to these polypeptides are useful in providing immunological probes for differential identification of the tissue(s) or cell type(s). For a number of disorders of the above tissues or cells, particularly of the eye, expression of this gene at significantly higher or lower levels may be routinely detected in certain tissues or cell types (e.g., opthalmic tissue, retinal tissue, cancerous and wounded tissues) or bodily fluids (e.g., lymph, vitreous humor, aqueous humor, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 89 as residues: Gln-27 to Arg-36.

The tissue distribution in retinal tissue combined with the detected GAS biological activity suggests that polynucleotides and polypeptides corresponding to this gene are useful for the diagnosis and treatment of visual disorders of the eye. The protein is useful in modulating the immune response to aberrant polypeptides, as may exist in proliferating and cancerous cells and tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1005 of SEQ ID NO:33, b is an integer of 15 to 1019, where both a and b correspond to the positions of nucleotide residues shown in SEQ ID NO:33, and where b is greater than or equal to a+14.

Features of Protein Encoded by Gene No: 24

In specific embodiments, polypeptides of the invention comprise the following amino acid sequence: GTAHLPTL-HWKPLLS (SEQ ID NO:197). Polynucleotides encoding these polypeptides are also encompassed by the invention.

This gene is expressed primarily in synovial fluid of a patient with chronic synovitis.

Therefore, polynucleotides and polypeptides of the invention are useful as reagents for differential identification of the tissue(s) or cell type(s) present in a biological sample and for diagnosis of diseases and conditions which include, but are not limited to, immune or skeletal disorders, particularly inflammatory disorders such as arthritis. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in synovial fluid suggests that polynucleotides and polypeptides corresponding to this gene are useful for the diagnosis and treatment of inflammatory disorders such as arthritis. Moreover, the expression of this gene product in synovium would suggest a role in the detection and treatment of disorders and conditions afflicting the skeletal system, in particular osteoporosis, bone cancer, connective tissue disorders (e.g., trauma, tendonitis, chrondomalacia and inflammation). The protein is also useful in the diagnosis or treatment of various autoimmune disorders (i.e., rheumatoid arthritis, lupus, scleroderma, and dermatomyositis), dwarfism, spinal deformation, joint abnormalities, and chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 419 of SEQ ID NO:34, b is an integer of 15 to 433, where both a and b correspond to the positions of nucleotide residues shown in SEQ ID NO:34, and where b is greater than or equal to a+14.

Features of Protein Encoded by Gene No: 25

In specific embodiments, polypeptides of the invention comprise the following amino acid sequence: LVMQ-CLGQVLSPLRTSVCLPIERGRWPGMVPHTTSALGG (SEQ ID NO:198); EPACLSH (SEQ ID NO:200); and/or QNTIHSLLPQGRMTKSLVLEEQKRK-AGRSEMKLELLMRVSLWYSGQALV-LLGLITNLSCSVLGKSFHLSGPLSVSL (SEQ ID NO:199). Polynucleotides encoding these polypeptides are also encompassed by the invention.

This gene is expressed primarily in human synovium.

Therefore, polynucleotides and polypeptides of the invention are useful as reagents for differential identification of the tissue(s) or cell type(s) present in a biological sample and for diagnosis of diseases and conditions which include, but are not limited to, immune and skeletal diseases and/or disorders, particularly inflammatory conditions, such as arthritis. Similarly, polypeptides and antibodies directed to these polypeptides are useful in providing immunological probes for differential identification of the tissue(s) or cell type(s). For a number of disorders of the above tissues or cells, particularly of the immune and inflammatory systems, expression of this gene at significantly higher or lower levels may be routinely detected in certain tissues or cell types (e.g., skeletal, synovium, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in synovium suggests that polynucleotides and polypeptides corresponding to this gene are useful for the study, diagnosis, and treatment of immune and inflammatory disorders. In addition, the gene product may play a role in the detection and treatment of disorders and conditions affecting the skeletal system, in particular osteoporosis, bone cancer, connective tissue disorders (e.g., arthritis, trauma, tendonitis, chrondomalacia and inflammation). The protein is also useful in the diagnosis or treatment of autoimmune disorders which include rheumatoid arthritis, lupus, scleroderma, dermatomyositis, dwarfism, spinal deformation, joint abnormalities, and chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 628 of SEQ ID NO:35, b is an integer of 15 to 642, where both a and b correspond to the positions of nucleotide residues shown in SEQ ID NO:35, and where b is greater than or equal to a+14.

Features of Protein Encoded by Gene No: 26

In specific embodiments, polypeptides of the invention comprise the following amino acid sequence: RDFG-CEPSPGTDTGSLSFLV (SEQ ID NO:201). Polynucleotides encoding these polypeptides are also encompassed by the invention.

This gene is expressed primarily in synovial fluid of a patient with chronic synovitis.

Therefore, polynucleotides and polypeptides of the invention are useful as reagents for differential identification of the tissue(s) or cell type(s) present in a biological sample and for diagnosis of diseases and conditions which include, but are not limited to, immune or skeletal disorders, particularly inflammatory disorders such as arthritis. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 92 as residues: Pro-29 to Ser-35.

The tissue distribution in synovium suggests that polynucleotides and polypeptides corresponding to this gene are useful for the diagnosis and treatment of inflammatory disorders such as arthritis. In addition, the gene product may play a role in the detection and treatment of disorders and conditions afflicting the skeletal system, in particular osteoporosis, bone cancer, as well as, disorders of the connective tissues (e.g., arthritis, trauma, tendonitis, chrondomalacia and inflammation). Moreover, the protein is also useful in the diagnosis or treatment of various autoimmune disorders such as rheumatoid arthritis, lupus, scleroderma, dermatomyositis, dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 653 of SEQ ID NO:36, b is an integer of 15 to 667, where both a and b correspond to the positions of nucleotide residues shown in SEQ ID NO:36, and where b is greater than or equal to a+14.

Features of Protein Encoded by Gene No: 27

When tested against K562 cell lines, supernatants removed from cells containing this gene activated the ISRE (interferon-sensitive responsive element) promoter element. Thus, it is likely that this gene activates leukemia cells through the Jak-STAT signal transduction pathway. ISRE is a promoter element found upstream in many genes which are involved in the Jak-STAT pathway. The Jak-STAT pathway is a large, signal transduction pathway involved in the differentiation and proliferation of cells. Therefore, activation of the Jak-STAT pathway, reflected by the binding of the ISRE element, can be used to indicate proteins involved in the proliferation and differentiation of cells.

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune and blood disorders, particularly inflammatory or immunodeficiency disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 93 as residues: Gly-3 1 to Phe-36.

The tissue distribution in T-cells, combined with the detected ISRE biological activity suggests that polynucleotides and polypeptides corresponding to this gene are useful for the study and treatment of immune and blood diseases. More specifically, the gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 640 of SEQ ID NO:37, b is an integer of 15 to 654, where both a and b correspond to the positions of nucleotide residues shown in SEQ ID NO:37, and where b is greater than or equal to a+14.

Features of Protein Encoded by Gene No: 28

When tested against K562 cell lines, supernatants removed from cells containing this gene activated the ISRE (interferon-sensitive responsive element) promoter element. Thus, it is likely that this gene activates leukemia cells,and to a lesser extent, in immune and hematopoeitic cells and tissues, through the Jak-STAT signal transduction pathway. ISRE is a promoter element found upstream in many genes which are involved in the Jak-STAT pathway. The Jak-STAT pathway is a large, signal transduction pathway involved in the differentiation and proliferation of cells. Therefore, activation of the Jak-STAT pathway, reflected by the binding of the ISRE element, can be used to indicate proteins involved in the proliferation and differentiation of cells.

This gene is expressed primarily in human fibrosarcoma.

Therefore, polynucleotides and polypeptides of the invention are useful as reagents for differential identification of the tissue(s) or cell type(s) present in a biological sample and for diagnosis of diseases and conditions which include, but are not limited to, muscle disorders, particularly proliferative conditions such as cancer or fibroids. Similarly, polypeptides and antibodies directed to these polypeptides are useful in providing immunological probes for differential identification of the tissue(s) or cell type(s). For a number of disorders of the above tissues or cells, particularly of the metabolic system, expression of this gene at significantly higher or lower levels may be routinely detected in certain tissues or cell types (e.g., muscle, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 94 as residues: Asn-12 to Thr-18.

The tissue distribution in fibrosarcoma, combined with the detected ISRE biological activity, suggests that polynucleotides and polypeptides corresponding to this gene are useful for the study, diagnosis, and/or treatment of various cancers. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 717 of SEQ ID NO:38, b is an integer of 15 to 731, where both a and b correspond to the positions of nucleotide residues shown in SEQ ID NO:38, and where b is greater than or equal to a+14.

Features of Protein Encoded by Gene No: 29

In specific embodiments, polypeptides of the invention comprise the following amino acid sequence: SVILLCPFF (SEQ ID NO:202). Polynucleotides encoding these polypeptides are also encompassed by the invention.

This gene is expressed primarily in salivary gland.

Therefore, polynucleotides and polypeptides of the invention are useful as reagents for differential identification of the tissue(s) or cell type(s) present in a biological sample and for diagnosis of diseases and conditions which include, but are not limited to, epithelial, immune, and digestive disorders. Similarly, polypeptides and antibodies directed to these polypeptides are useful in providing immunological probes for differential identification of the tissue(s) or cell type(s). For a number of disorders of the above tissues or cells, particularly of the epithelial, digestive, and immune systems, expression of this gene at significantly higher or lower levels may be routinely detected in certain tissues or cell types (e.g., epithelial, immune, digestive tissues, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in salivary tissue suggests that polynucleotides and polypeptides corresponding to this gene are useful for the study, diagnosis, and treatment of various disorders of the immune, digestive and epithelial systems. The protein is useful in modulating the immune response to aberrant polypeptides, as may be present in the cells and tissues of proliferative organs. The protein may also be useful in enhancing or inhibiting the bodies antibiological and microbial defenses (i.e., by enhancing the secretion of an antibiological agent in saliva, such as nitric oxide, for example). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 364 of SEQ ID NO:39, b is an integer of 15 to 378, where both a and b correspond to the positions of nucleotide residues shown in SEQ ID NO:39, and where b is greater than or equal to a+14.

Features of Protein Encoded by Gene No: 30

This gene is expressed primarily in spongy brain tissue obtained from Alzheimer's patients.

Therefore, polynucleotides and polypeptides of the invention are useful as reagents for differential identification of the tissue(s) or cell type(s) present in a biological sample and for diagnosis of diseases and conditions which include, but are not limited to, Alzheimer's disease; neurodegenerative disorders including, but not restricted to Alzheimer's, such as schizophrenia, ALS, etc. Similarly, polypeptides and antibodies directed to these polypeptides are useful in providing immunological probes for differential identification of the tissue(s) or cell type(s). For a number of disorders of the above tissues or cells, particularly of the brain and nervous system, expression of this gene at significantly higher or lower levels may be routinely detected in certain tissues or cell types (e.g., neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 96 as residues: Leu-69 to Leu-74.

The tissue distribution suggests that polynucleotides and polypeptides corresponding to this gene are useful for the diagnosis and/or treatment of neurodegenerative disorders, particularly Alzheimer's disease. Specific expression of this gene product in the brain tissue of Alzheimer's patients suggests that it may play a deleterious role in the progression of the disease. Alternately, it may represent an attempted response by the body to combat the progression of Alzheimer's. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 628 of SEQ ID NO:40, b is an integer of 15 to 642, where both a and b correspond to the positions of nucleotide residues shown in SEQ ID NO:40, and where b is greater than or equal to a+14.

Features of Protein Encoded by Gene No: 31

In specific embodiments, polypeptides of the invention comprise the following amino acid sequence: ARDRTHCLL (SEQ ID NO:203). Polynucleotides encoding these polypeptides are also encompassed by the invention.

This gene is expressed primarily in epididymus, and to a lesser extent, in colon tissue.

Therefore, polynucleotides and polypeptides of the invention are useful as reagents for differential identification of the tissue(s) or cell type(s) present in a biological sample and for diagnosis of diseases and conditions which include, but are not limited to, infertility; sperm developmental/survival disorders. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types or cell types (e.g., reproductive, cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 97 as residues: Lys-35 to Glu-41, Ala-62 to Asn-67.

The tissue distribution in epididymus suggests that polynucleotides and polypeptides corresponding to this gene are useful for the diagnosis and/or treatment of male infertility. Specific expression of this gene product within the epididymus suggests that it plays key roles in the development and/or survival of sperm. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 428 of SEQ ID NO:41, b is an integer of 15 to 442, where both a and b correspond to the positions of nucleotide residues shown in SEQ ID NO:41, and where b is greater than or equal to a+14.

Features of Protein Encoded by Gene No: 32

In specific embodiments, polypeptides of the invention comprise the following amino acid sequence: THQTLAATKG (SEQ ID NO:204). Polynucleotides encoding these polypeptides are also encompassed by the invention.

The gene encoding the disclosed cDNA is thought to reside on chromosome 4. Accordingly, polynucleotides related to this invention are useful as a marker in linkage analysis for chromosome 4.

This gene is expressed primarily in resting T-cells, and to a lesser extent, in healing groin wound library.

Therefore, polynucleotides and polypeptides of the invention are useful as reagents for differential identification of the tissue(s) or cell type(s) present in a biological sample and for diagnosis of diseases and conditions which include, but are not limited to, immunological and wound healing diseases and/or disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types or cell types (e.g., immune, metabolic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 98 as residues: Lys-29 to Val-34, Cys-94 to Asp-99, Ser-102 to Val-107, Gln-133 to Lys-139.

The tissue distribution in T-cells suggests that polynucleotides and polypeptides corresponding to this gene are useful for modulating the immune response during wound repair. The translation product of this gene may function as a stimulator for the growth of bone, cartilage, tendons, ligaments and/or nerves, which would be useful for the treatment of wounds. Moreover, the protein may be useful in detection, treating, and/or preventing metabolic conditions, particulary conditions related to aberrant fatty-acid metabolism. The protein is useful in modulating the immune response to aberrant polypeptides, as may exist in proliferating and cancerous cells and tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1720 of SEQ ID NO:42, b is an integer of 15 to 1734, where both a and b correspond to the positions of nucleotide residues shown in SEQ ID NO:42, and where b is greater than or equal to a+14.

Features of Protein Encoded by Gene No: 33

In specific embodiments, polypeptides of the invention comprise the following amino acid sequence: MPRPSPLSSPGSPVTSQLCSPMPSLN-PALPWGLLLALPGLSLHTPFQTLTAAS-PHQPSGDSAAHLSAHSFLLDSH (SEQ ID NO:205); VPCGTACSVGAAA (SEQ ID NO:206); and/or TSRSM-FFTSRPRTPWTSCLQIAPLALLQSLGIWQHSIGA (SEQ ID NO:207). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune-related diseases and/or disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 99 as residues: Pro-46 to Pro-53, His-55 to Cys-63.

The tissue distribution in neutrophils suggests that polynucleotides and polypeptides corresponding to this gene are useful for the diagnosis and treatment of immune related diseases. Moreover, the expression of this gene product in neutrophils suggests a role in regulating the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 503 of SEQ ID NO:43, b is an integer of 15 to 517, where both a and b correspond to the positions of nucleotide residues shown in SEQ ID NO:43, and where b is greater than or equal to a+14.

Features of Protein Encoded by Gene No: 34

This gene is expressed primarily in 12 week-old human embryos.

Therefore, polynucleotides and polypeptides of the invention are useful as reagents for differential identification of the tissue(s) or cell type(s) present in a biological sample and for diagnosis of diseases and conditions which include, but are not limited to, developmental abnormalities; cancer. Similarly, polypeptides and antibodies directed to these polypeptides are useful in providing immunological probes for differential identification of the tissue(s) or cell type(s). For a number of disorders of the above tissues or cells, particularly of the embryo, expression of this gene at significantly higher or lower levels may be routinely detected in certain tissues or cell types or cell types (e.g., embryonic, cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 100 as residues: Ser-37 to Tyr-43.

The tissue distribution in embryonic tissue suggests that polynucleotides and polypeptides corresponding to this gene are useful for the diagnosis, detection, and/or treatment of developmental disorders. The relatively specific expression of this gene product during embryogenesis suggests that it may be a key player in the proliferation, maintenance, and/or differentiation of various cell types during development. It may also act as a morphogen to control cell and tissue type specification. Expression within embryonic tissue and other cellular sources marked by proliferating cells suggests that this protein may play a role in the regulation of cellular division. Because of potential roles in proliferation and differentiation, this gene product may have applications in the adult for tissue regeneration and the treatment of cancers.

Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Protein, as well as,, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 472 of SEQ ID NO:44, b is an integer of 15 to 486, where both a and b correspond to the positions of nucleotide residues shown in SEQ ID NO:44, and where b is greater than or equal to a+14.

Features of Protein Encoded by Gene No: 35

In specific embodiments, polypeptides of the invention comprise the following amino acid sequence: GTAGFS-DLLLVNVMCQTRRSITFKNKLQKESRIYP (SEQ ID NO:208). Polynucleotides encoding these polypeptides are also encompassed by the invention.

This gene is expressed primarily in CD34 depleted buffy coat (cord blood).

Therefore, polynucleotides and polypeptides of the invention are useful as reagents for differential identification of the tissue(s) or cell type(s) present in a biological sample and for diagnosis of diseases and conditions which include, but are not limited to, blood and immune diseases and/or disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types or cell types (e.g., immune, cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 101 as residues: Pro-26 to Arg-40, Pro-43 to Lys-49.

The tissue distribution in CD34 depleted buffy coat cells suggests that polynucleotides and polypeptides corresponding to this gene are useful for the treatment of haemopoietic and immune disorders. Expression of this gene product in CD34 depleted buffy coat (cord blood) suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the natural gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 812 of SEQ ID NO:45, b is an integer of 15 to 826, where both a and b correspond to the positions of nucleotide residues shown in SEQ ID NO:45, and where b is greater than or equal to a+14.
Features of Protein Encoded by Gene No: 36

This gene is expressed primarily in adipose tissue, and to a lesser extent, in placental tissue.

Therefore, polynucleotides and polypeptides of the invention are useful as reagents for differential identification of the tissue(s) or cell type(s) present in a biological sample and for diagnosis of diseases and conditions which include, but are not limited to, metabolic or reproductive disorders, particularly obesity. Similarly, polypeptides and antibodies directed to these polypeptides are useful in providing immunological probes for differential identification of the tissue(s) or cell type(s). For a number of disorders of the above tissues or cells, particularly of the metabolic system, expression of this gene at significantly higher or lower levels may be routinely detected in certain tissues or cell types or cell types (e.g., adipose, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in adipose tissue suggests that polynucleotides and polypeptides corresponding to this gene are useful for the treatment of obesity by targeting adipose cells. Furthermore, the protein product of this clone may show utility in ameliorating conditions which occur secondary to aberrant fatty-acid metabolism (e.g., aberrant myelin sheath development), either directly or indirectly. Protein, as well as, antibodies directed against the protein may show utility as a tissue-specific marker and/or immunotherapy target for the above listed tissues.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 680 of SEQ ID NO:46, b is an integer of 15 to 694, where both a and b correspond to the positions of nucleotide residues shown in SEQ ID NO:46, and where b is greater than or equal to a+14.
Features of Protein Encoded by Gene No: 37

This gene is expressed primarily in adult pulmonary tissue.

Therefore, polynucleotides and polypeptides of the invention are useful as reagents for differential identification of the tissue(s) or cell type(s) present in a biological sample and for diagnosis of diseases and conditions which include, but are not limited to, pulmonary disorders. Similarly, polypeptides and antibodies directed to these polypeptides are useful in providing immunological probes for differential identification of the tissue(s) or cell type(s). For a number of disorders of the above tissues or cells, particularly of the pulmonary system, expression of this gene at significantly higher or lower levels may be routinely detected in certain tissues or cell types or cell types (e.g., lung, cancerous and wounded tissues) or bodily fluids (e.g., lymph, pulmonary surfactant or sputum, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in pulmonary tissue suggests that polynucleotides and polypeptides corresponding to this gene are useful for the diagnosis and/or treatment of certain pulmonary disorders, such as lung cancer, ARDS, and emphysema. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 842 of SEQ ID NO:47, b is an integer of 15 to 856, where both a and b correspond to the positions of nucleotide residues shown in SEQ ID NO:47, and where b is greater than or equal to a+14.
Features of Protein Encoded by Gene No: 38

This gene is expressed primarily in amygdala tissue of the brain, and to a lesser extent, in infant brain tissues.

Therefore, polynucleotides and polypeptides of the invention are useful as reagents for differential identification of the tissue(s) or cell type(s) present in a biological sample and for diagnosis of diseases and conditions which include, but are not limited to, developmental and neurodegenerative diseases of the brain and nervous system. Similarly, polypeptides and antibodies directed to these polypeptides are useful in providing immunological probes for differential identification of the tissue(s) or cell type(s). For a number of disorders of the above tissues or cells, particularly of the central nervous system (CNS), expression of this gene at significantly higher or lower levels may be routinely detected in certain tissues or cell types or cell types (e.g., brain, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 104 as residues: Pro-30 to Gln-35, Pro-44 to Leu-50.

The tissue distribution in neural tissues suggests that polynucleotides and polypeptides corresponding to this gene are useful for the treatment and/or diagnosis of behavioral or nervous system disorders, such as depression, schizophrenia, Alzheimer's disease, dementia, paranoia, autism, and addictive behavior. The amygdala processes sensory information and relays this to other areas of the brain including the endocrine and autonomic domains of the hypothalamus and the brain stem. Thus, the translation product of this gene may also be useful for the detection and/or treatment of neural disorders that impact processes mediated by the amygdala. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1629 of SEQ ID NO:48, b is an integer of 15 to 1643, where both a and b correspond to the positions of nucleotide residues shown in SEQ ID NO:48, and where b is greater than or equal to a+14.

Features of Protein Encoded by Gene No: 39

This gene is expressed primarily in synovial hypoxia tissue.

Therefore, polynucleotides and polypeptides of the invention are useful as reagents for differential identification of the tissue(s) or cell type(s) present in a biological sample and for diagnosis of diseases and conditions which include, but are not limited to, connective tissue disorders. Similarly, polypeptides and antibodies directed to these polypeptides are useful in providing immunological probes for differential identification of the tissue(s) or cell type(s). For a number of disorders of the above tissues or cells, particularly of the connective tissue system, expression of this gene at significantly higher or lower levels may be routinely detected in certain tissues or cell types (e.g., skeletal, connective, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 105 as residues: Asn-30 to Gly-37.

The tissue distribution in synovial hypoxia tissue suggests that polynucleotides and polypeptides corresponding to this gene are useful for the treatment and/or diagnosis of diseases of connective tissue, particularly synovia, including but not limited to inflammation, rheumatoid arthritis, osteoarthritis, and cartilage tears and physical injury, as well as osteoporosis, tendonitis, chrondomalacia and inflammation. Furthermore, the translation product of this gene may be useful in the diagnosis and/or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 695 of SEQ ID NO:49, b is an integer of 15 to 709, where both a and b correspond to the positions of nucleotide residues shown in SEQ ID NO:49, and where b is greater than or equal to a+14.

Features of Protein Encoded by Gene No: 40

In specific embodiments, polypeptides of the invention comprise the following amino acid sequence: PFRNSRVR-PKGSRDALSWSSCTGPQPGTSATVGSLL CGGVP-CIAGHPAASPASCSVPVAPHPAVVTAQVSR CAECPLVMLRGTGVLPPGFE0RCLTPTSGVSLPCV (SEQ ID NO:209). Polynucleotides encoding these polypeptides are also encompassed by the invention.

This gene is expressed primarily in synovial cells stimulated with IL-1 and TNF.

Therefore, polynucleotides and polypeptides of the invention are useful as reagents for differential identification of the tissue(s) or cell type(s) present in a biological sample and for diagnosis of diseases and conditions which include, but are not limited to, inflammation of connective tissue. Similarly, polypeptides and antibodies directed to these polypeptides are useful in providing immunological probes for differential identification of the tissue(s) or cell type(s). For a number of disorders of the above tissues or cells, particularly of connective tissue, expression of this gene at significantly higher or lower levels may be routinely detected in certain tissues or cell types or cell types (e.g., connective, skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 106 as residues: Gln-31 to Pro-39.

The tissue distribution in synovial cells suggests that polynucleotides and polypeptides corresponding to this gene are useful for the treatment and/or diagnosis of inflammation of connective tissues, particularly the synovium, in diseases such as rheumatoid arthritis, sepsis, infection of the joint, and tissue damage from physical injury. Furthermore, the expression of this gene product may be useful in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 527 of SEQ ID NO:50, b is an integer of 15 to 541, where both a and b correspond to the positions of nucleotide residues shown in SEQ ID NO:50, and where b is greater than or equal to a+14.

Features of Protein Encoded by Gene No: 41

When tested against U937 myeloid cell lines as well as Jurkat T-cell cell lines, supernatants removed from cells containing this gene activated the GAS assay. Therefore, it is likely that this gene activates myeloid cells, and to a lesser extent, in immune and hematopoietic cells through the Jak-STAT signal transduction pathway. Gamma activating sequence (GAS) is a promoter element found upstream of many genes involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in melanocytes, and to a lesser extent, in the synovium, testes, and CD34 cells.

Therefore, polynucleotides and polypeptides of the invention are useful as reagents for differential identification of the tissue(s) or cell type(s) present in a biological sample and for diagnosis of diseases and conditions which include, but are not limited to, musculo-skeletal diseases and disorders, such as skin discoloration or arthritis, as well as male reproductive disorders. Similarly, polypeptides and antibodies directed to these polypeptides are useful in providing immunological probes for differential identification of the tissue(s) or cell type(s). For a number of disorders of the above tissues or cells, particularly of the musculo-skeletal and reproductive systems, expression of this gene at significantly higher or lower levels may be routinely detected in certain tissues or cell types or cell types (e.g., musculo-skeletal, reproductive, bone, cartilage, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 107 as residues: Arg-35 to Ala-41.

The tissue distribution in synovium suggests that polynucleotides and polypeptides corresponding to this gene are useful for the treatment and/or diagnosis of diseases affecting the skeletal system, in particular osteoporosis, as well as disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid).

Alternatively, the tissue distribution in testes tissue indicates that the protein product of this clone is useful for the treatment and diagnosis of conditions concerning proper testicular function (e.g., endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 706 of SEQ ID NO:51, b is an integer of 15 to 720, where both a and b correspond to the positions of nucleotide residues shown in SEQ ID NO:51, and where b is greater than or equal to a+14.

Features of Protein Encoded by Gene No: 42

In specific embodiments, polypeptides of the invention comprise the following amino acid sequence: MDTYTF-LIKICKIFCSFLKCHIQVCGHLLFL-WTSIKWARKQHHCSRCKAIGLSS (SEQ ID NO:210). Polynucleotides encoding these polypeptides are also encompassed by the invention.

This gene is expressed primarily in synovial tissue and neutrophils.

Therefore, polynucleotides and polypeptides of the invention are useful as reagents for differential identification of the tissue(s) or cell type(s) present in a biological sample and for diagnosis of diseases and conditions which include, but are not limited to, musculo-skeletal and immune diseases. Similarly, polypeptides and antibodies directed to these polypeptides are useful in providing immunological probes for differential identification of the tissue(s) or cell type(s). For a number of disorders of the above tissues or cells, particularly of the immune and musculo- skeletal systems, expression of this gene at significantly higher or lower levels may be routinely detected in certain tissues or cell types or cell types (e.g., immune, skeletal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in synovium and neutrophils suggests that polynucleotides and polypeptides corresponding to this gene are useful for the treatment and/or diagnosis of immune diseases, particularly inflammatory conditions such as arthritis. Expression of this gene product in neutrophils suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. Furthermore, this gene product may have commercial utility in the expansion of stem cells and committed progenitors of various blood lineages, and in the differentiation and/or proliferation of various cell types.

In addition, the expression of this gene product in synovium suggests a role in the detection and treatment of disorders and conditions affecting the skeletal system, in particular osteoporosis as well as disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial arthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 965 of SEQ ID NO:52, b is an integer of 15 to 979, where both a and b correspond to the positions of nucleotide residues shown in SEQ ID NO:52, and where b is greater than or equal to a+14.

Features of Protein Encoded by Gene No: 43

This gene is expressed primarily in CD34 depleted buffy coat (cord blood).

Therefore, polynucleotides and polypeptides of the invention are useful as reagents for differential identification of the tissue(s) or cell type(s) present in a biological sample and for diagnosis of diseases and conditions which include, but are not limited to, blood, developmental, and immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 109 as residues: Ser-41 to Lys-49.

The tissue distribution in CD34 depleted buffy coat suggests that polynucleotides and polypeptides corresponding to this gene are useful for the diagnosis and/or treatment of haemopoietic and immune disorders. Furthermore, expression of this gene product in CD34 depleted buffy coat (cord blood) suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 366 of SEQ ID NO:53, b is an integer of 15 to 380, where both a and b correspond to the positions of nucleotide residues shown in SEQ ID NO:53, and where b is greater than or equal to a+14.

Features of Protein Encoded by Gene No: 44

The translation product of this gene shares sequence homology with the conserved NADH-isocitrate dehydrogenase which is thought to be important in the proliferation of lymphocytes. When tested against Jurkat T-cell cell lines, supernatants removed from cells containing this gene activated the GAS assay. Therefore, it is likely that this gene activates T-cells, and to a lesser extent in immune and hematopoietic cells and tissues, through the Jak-STAT signal transduction pathway. Gamma activating sequence (GAS) is a promoter element found upstream of many genes involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

In specific embodiments, polypeptides of the invention comprise the following amino acid sequences: DPRLAVLLLGVQILVERWRLQWDHYYL-CPHRVQAEEDVEKSQWNYPEHPGGDCLP-GAHHLQKHPTPSPWLDQAHHHWQARPWXPVQGH RLCGRPGRHFQNGLHPKRWQWCQGVGS-VQLPRSGVGMGMYNTDESISGFAH-SCFQYAIQKKWPLYMSTKNTILKAYDGR-FKDIFQEIFDKHYKTDFDKNKIWYEHRLIDDMVAQ VLKSSGGFVWACKNYDGDVQSDILAQG-FGSLGLMTSVLVCPDGKTIEAEAAH-GTVTRHYREHQKGRPTSTNPIASIFAW-TRGLEHRGKLDGNQDLIRFAQMLEKVCVETVESGA MTKDLAGCIHGLSNVKLNEHFLNTTD-FLDTIKSNLDRALGRQ (SEQ ID NO:21 1); DPRLAVLLLGVQILVERWRLQWDHYYL-CPHRVQAEEDVEKSQWNYPEH (SEQ ID NO:212); PGGDCLPGAHHLQKHPTPSPWLDQAHHH-WQARPWXPVQGHRLCGRPGRHFQNGL (SEQ ID NO:213); HPKRWQWCQGVGSVQLPRSGVGMGMY-NTDESISGFAHSCFQYAIQKKWPLYMST-KNTILKAYDGRFKDIF (SEQ ID NO:214); QEIFD-KHYKTDFDKNKIWYEHRLIDDMVAQVLKSSGGFV WACKNYDGDVQSDILAQGFGSLGLMTSVLVC (SEQ ID NO:215); PDGKTIEAEAAHGTVTRHYRE-HQKGRPTSTNPIASIFAWTRGLE-HRGKLDGNQDLIRFAQMLEKVCVETV (SEQ ID NO:216); and/or ESGAMTKDLAGCIHGLSNVKLNEH-FLNTTDFLDTIKSNLDRALGRQ (SEQ ID NO:217). Polynucleotides encoding these polypeptides are also encompassed by the invention.

This gene is expressed primarily in T-cells and B-cells, and to a lesser extent in breast cancer tissue.

Therefore, polynucleotides and polypeptides of the invention are useful as reagents for differential identification of the tissue(s) or cell type(s) present in a biological sample and for diagnosis of diseases and conditions which include, but are not limited to, breast cancer, leukemia, HIV, and tonsillitis. Similarly, polypeptides and antibodies directed to these polypeptides are useful in providing immunological probes for differential identification of the tissue(s) or cell type(s). For a number of disorders of the above tissues or cells, particularly of the immune/lymphoid system, and breast cancers, expression of this gene at significantly higher or lower levels may be routinely detected in certain tissues or cell types (e.g., immune, reproductive, breast, cancerous and wounded tissues) or bodily fluids (e.g., lymph, breast milk, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 110 as residues: Cys-31 to Trp-36.

The tissue distribution in immune cells, combined with the detected gas biological activity, and its homology to the NADH-isocitrate dehydrogenase, suggests that polynucleotides and polypeptides corresponding to this gene are useful for the treatment and/or diagnosis of diseases related to the proliferation of lymphoid cells. Furthermore, it could be especially useful in helping the body to produce mature lymphocytes to enhance the immune system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2009 of SEQ ID NO:54, b is an integer of 15 to 2023, where both a and b correspond to the positions of nucleotide residues shown in SEQ ID NO:54, and where b is greater than or equal to a+14.

Features of Protein Encoded by Gene No: 45

This gene is expressed primarily in PHA treated T-cells.

Therefore, polynucleotides and polypeptides of the invention are useful as reagents for differential identification of the tissue(s) or cell type(s) present in a biological sample and for diagnosis of diseases and conditions which include, but are not limited to, T-cell disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells suggests that polynucleotides and polypeptides corresponding to this gene are useful for the diagnosis and/or treatment of immune disorders involving T-cells. Furthermore, the gene product may play a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Expression of this gene product in T cells also strongly suggests a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 871 of SEQ ID NO:55, b is an integer of 15 to 885, where both a and b correspond to the positions of nucleotide residues shown in SEQ ID NO:55, and where b is greater than or equal to a+14.

Features of Protein Encoded by Gene No: 46

This gene is expressed primarily in fetal heart tissue.

Therefore, polynucleotides and polypeptides of the invention are useful as reagents for differential identification of the tissue(s) or cell type(s) present in a biological sample and for diagnosis of diseases and conditions which include, but are not limited to, mitrovalve prolapse, congenital heart diseases or arythmic heartbeats. Similarly, polypeptides and antibodies directed to these polypeptides are useful in providing immunological probes for differential identification of the tissue(s) or cell type(s). For a number of disorders of the above tissues or cells, particularly of the cardiovascular system, expression of this gene at significantly higher or lower levels may be routinely detected in certain tissues or cell types or cell types (e.g., cardiac, developmental, cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal heart suggests that polynucleotides and polypeptides corresponding to this gene are useful for the treatment and/or diagnosis of heart diseases especially in the developing fetus. Furthermore, the tissue distribution in fetal heart tissue indicates that the protein product of this gene is useful for the diagnosis and treatment of conditions and pathologies of the cardiovascular system, such as heart disease, restenosis, atherosclerosis, stoke, angina, thrombosis, and wound healing. The sequence itself could be used in genetic therapy, in utero, to correct defects in the developing fetus. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1092 of SEQ ID NO:56, b is an integer of 15 to 1106, where both a and b correspond to the positions of nucleotide residues shown in SEQ ID NO:56, and where b is greater than or equal to a+14.

Features of Protein Encoded by Gene No: 47

This gene is expressed primarily in spleen tissue of chronic lymphocytic leukemia patient.

Therefore, polynucleotides and polypeptides of the invention are useful as reagents for differential identification of the tissue(s) or cell type(s) present in a biological sample and for diagnosis of diseases and conditions which include, but are not limited to, leukemia. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 113 as residues: Pro-42 to Lys-49.

The tissue distribution in spleen tissue suggests that polynucleotides and polypeptides corresponding to this gene are useful for the treatment and/or diagnosis of patients with leukemia. Expression of this gene product in spleen tissue suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 750 of SEQ ID NO:57, b is an integer of 15 to 764, where both a and b correspond to the positions of nucleotide residues shown in SEQ ID NO:57, and where b is greater than or equal to a+14.

Features of Protein Encoded by Gene No: 48

This gene is expressed primarily in liver cancer tissue, and to a lesser extent in bone marrow, neutrophils, and CD34 cells.

Therefore, polynucleotides and polypeptides of the invention are useful as reagents for differential identification of the tissue(s) or cell type(s) present in a biological sample and for diagnosis of diseases and conditions which include, but are not limited to, liver cancer and scerosis of the liver. Similarly, polypeptides and antibodies directed to these polypeptides are useful in providing immunological probes for differential identification of the tissue(s) or cell type(s). For a number of disorders of the above tissues or cells, particularly of the hepatic and lymphatic systems, expression of this gene at significantly higher or lower levels may be routinely detected in certain tissues or cell types (e.g., liver, immune, hematopoiectic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in cancerous liver tissue suggests that polynucleotides and polypeptides corresponding to this gene are useful for the treatment and/or diagnosis of liver cancer, possibly before the onset of symptoms. Similarly, this gene would be useful for the detection and treatment of liver disorders and cancers (e.g., hepatoblastoma, jaundice, hepatitis, liver metabolic diseases and conditions that are attributable to the differentiation of hepatocyte progenitor cells). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 724 of SEQ ID NO:58, b is an integer of 15 to 738, where both a and b correspond to the positions of nucleotide residues shown in SEQ ID NO:58, and where b is greater than or equal to a+14.

Features of Protein Encoded by Gene No: 49

This gene is expressed primarily in synovial hypoxia tissue.

Therefore, polynucleotides and polypeptides of the invention are useful as reagents for differential identification of the tissue(s) or cell type(s) present in a biological sample and for diagnosis of diseases and conditions which include, but are not limited to, connective tissue and joint disorders. Similarly, polypeptides and antibodies directed to these polypeptides are useful in providing immunological probes for differential identification of the tissue(s) or cell type(s). For a number of disorders of the above tissues or cells, particularly of connective tissue, expression of this gene at significantly higher or lower levels may be routinely detected in certain tissues or cell types (e.g., connective, skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in synovial hypoxia tissue suggests that polynucleotides and polypeptides corresponding to this gene are useful for the treatment and/or diagnosis of diseases of connective tissue, particularly synovia, including but not limited to inflammation, rheumatoid arthritis, osteoarthritis, and cartilage tears and physical injury. Furthermore, polynucleotides and polypeptides corresponding to this gene are useful in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 427 of SEQ ID NO:59, b is an integer of 15 to 441, where both a and b correspond to the positions of nucleotide residues shown in SEQ ID NO:59, and where b is greater than or equal to a+14.

Features of Protein Encoded by Gene No: 50

In specific embodiments, polypeptides of the invention comprise the following amino acid sequence: MIMGYK-SQKTFGLFDLXXVKGKTSVLEFDFWV-QIPVASLLALWLNRLLNSVKWALKXCVIHSVAVNX (SEQ ID NO: 218). Polynucleotides encoding these polypeptides are also encompassed by the invention.

This gene is expressed primarily in B-cell lymphoma tissue.

Therefore, polynucleotides and polypeptides of the invention are useful as reagents for differential identification of the tissue(s) or cell type(s) present in a biological sample and for diagnosis of diseases and conditions which include, but are not limited to, B-cell lymphoma. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 116 as residues: Arg-32 to Gly40.

The tissue distribution in B-cell lymphoma suggests that polynucleotides and polypeptides corresponding to this gene are useful for the diagnosis and/or treatment of immune or hematopoietic disorders, particularly those involving proliferative cells or tissues such as in cancers. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:60 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 770 of SEQ ID NO:60, b is an integer of 15 to 784, where both a and b correspond to the positions of nucleotide residues shown in SEQ ID NO:60, and where b is greater than or equal to a+14.

Features of Protein Encoded by Gene No: 51

This gene is expressed primarily in synovial hypoxia tissue.

Therefore, polynucleotides and polypeptides of the invention are useful as reagents for differential identification of the tissue(s) or cell type(s) present in a biological sample and for diagnosis of diseases and conditions which include, but are not limited to, connective tissue disorders. Similarly, polypeptides and antibodies directed to these polypeptides are useful in providing immunological probes for differential identification of the tissue(s) or cell type(s). For a number of disorders of the above tissues or cells, particularly of connective tissue, expression of this gene at significantly higher or lower levels may be routinely detected in certain tissues or cell types (e.g., connective, skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in synovial hypoxia tissue suggests that polynucleotides and polypeptides corresponding to this gene are useful for the treatment and/or diagnosis of diseases of connective tissue, particularly synovia, including but not limited to inflammation, rheumatoid arthritis, osteoarthritis, and cartilage tears and physical injury. Furthermore, polynucleotides and polypeptides corresponding to this gene are useful in the diagnosis or treatment of various autoimmune disorders such as rheumatoid arthritis, lupus, scleroderma, and dermatomyositis as well as dwarfism, spinal deformation, joint abnormalities, and chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:61 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 526 of SEQ ID NO:61, b is an integer of 15 to 540, where both a and b correspond to the positions of nucleotide residues shown in SEQ ID NO:61, and where b is greater than or equal to a+14.

Features of Protein Encoded by Gene No: 52

This gene is expressed primarily in synovial cells stimulated with IL-1 and TNF, and also in neutrophils.

Therefore, polynucleotides and polypeptides of the invention are useful as reagents for differential identification of the tissue(s) or cell type(s) present in a biological sample and for diagnosis of diseases and conditions which include, but are not limited to, inflammation of connective tissue and joints. Similarly, polypeptides and antibodies directed to these polypeptides are useful in providing immunological probes for differential identification of the tissue(s) or cell type(s). For a number of disorders of the above tissues or cells, particularly of connective tissue, expression of this gene at significantly higher or lower levels may be routinely detected in certain tissues or cell types (e.g., connective, skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 118 as residues: Val-4 to Glu-9, Lys-42 to Lys-47.

The tissue distribution in synovial cells suggests that polynucleotides and polypeptides corresponding to this gene are useful for the treatment and/or diagnosis of inflammation of connective tissues, particularly the synovium, in diseases such as rheumatoid arthritis, sepsis, infection of the joint, and tissue damage from physical injury. Furthermore, polynucleotides and polypeptides corresponding to this gene are useful in the diagnosis or treatment of various autoimmune disorders such as rheumatoid arthritis, lupus, scleroderma, and dermatomyositis as well as dwarfism, spinal deformation, joint abnormalities, and chondrodysplasias (ie. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:62 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 590 of SEQ ID NO:62, b is an integer of 15 to 604, where both a and b correspond to the positions of nucleotide residues shown in SEQ ID NO:62, and where b is greater than or equal to a+14.

Features of Protein Encoded by Gene No: 53

In specific embodiments, polypeptides of the invention comprise the following amino acid sequence: MKSFPSTYFKSSSFQNTKYQTGVISVLISYEIEYAAFYHLSCKITLPSSVSRNCFISEXLVASQCLDT (SEQ ID NO:219). Polynucleotides encoding these polypeptides are also encompassed by the invention.

This gene is expressed primarily in frontal cortex tissue sampled from an epileptic patient.

Therefore, polynucleotides and polypeptides of the invention are useful as reagents for differential identification of the tissue(s) or cell type(s) present in a biological sample and for diagnosis of diseases and conditions which include, but are not limited to, neural disorders, such as epilepsy. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues or cell types (e.g., brain, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in frontal cortex tissue suggests that polynucleotides and polypeptides corresponding to this gene are useful for the treatment and/or diagnosis of epilepsy and related brain disorders. Elevated expression of this gene product within the frontal cortex tissue of the brain suggests that it may be involved in neuronal survival; synapse formation; conductance; neural differentiation, etc. Such involvement may impact many processes, such as learning and cognition. It may also be useful in the treatment of such neurodegenerative disorders as schizophrenia; ALS; or Alzheimer's. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:63 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 738 of SEQ ID NO:63, b is an integer of 15 to 752, where both a and b correspond to the positions of nucleotide residues shown in SEQ ID NO:63, and where b is greater than or equal to a+14.

TABLE 1

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HSIDU19 | 209277 09/18/97 | Uni-ZAP XR | 11 | 680 | 1 | 680 | 352 | 352 | 67 | 1 | 21 | 22 | 73 |
| 2 | HPRSB76 | 209277 09/18/97 | pBluescript | 12 | 741 | 1 | 741 | 127 | 127 | 68 | 1 | 22 | 23 | 59 |
| 3 | HTEIL66 | 209277 09/18/97 | Uni-ZAP XR | 13 | 619 | 1 | 619 | 123 | 123 | 69 | 1 | 24 | 25 | 134 |
| 4 | HSNAY92 | 209277 09/18/97 | Uni-ZAP XR | 14 | 611 | 1 | 611 | 127 | 127 | 70 | 1 | 29 | 30 | 35 |
| 5 | HSABG21 | 209277 09/18/97 | pBluescript SK- | 15 | 585 | 1 | 585 | 96 | 96 | 71 | 1 | 24 | 25 | 125 |
| 6 | HSAXB32 | 209277 09/18/97 | Uni-ZAP XR | 16 | 1040 | 1 | 1040 | 97 | 97 | 72 | 1 | 36 | 37 | 51 |
| 7 | HPEAD48 | 209277 09/18/97 | Uni-ZAP XR | 17 | 625 | 1 | 625 | 203 | 203 | 73 | 1 | 18 | 19 | 98 |
| 8 | HPVAB94 | 209277 09/18/97 | Uni-ZAP XR | 18 | 819 | 1 | 819 | 80 | 80 | 74 | 1 | 25 | 26 | 44 |
| 9 | HSAXB81 | 209277 09/18/97 | Uni-ZAP XR | 19 | 782 | 1 | 782 | 143 | 143 | 75 | 1 | 20 | 21 | 47 |
| 10 | HSAYC21 | 209277 09/18/97 | Uni-ZAP XR | 20 | 655 | 1 | 655 | 155 | 155 | 76 | 1 |  |  | 26 |
| 11 | HSLCU73 | 209277 09/18/97 | Uni-ZAP XR | 21 | 798 | 1 | 798 | 7 | 7 | 77 | 1 | 22 | 23 | 41 |
| 12 | HSSFZ70 | 209277 09/18/97 | Uni-ZAP XR | 22 | 646 | 1 | 646 | 212 | 212 | 78 | 1 | 22 | 23 | 22 |
| 13 | HTEIP36 | 209277 09/18/97 | Uni-ZAP XR | 23 | 752 | 1 | 752 | 22 | 22 | 79 | 1 | 19 | 20 | 58 |
| 14 | HYBAY77 | 209277 09/18/97 | Uni-ZAP XR | 24 | 815 | 60 | 815 | 157 | 157 | 80 | 1 | 44 | 45 | 47 |
| 15 | HROAE78 | 209277 09/18/97 | Uni-ZAP XR | 25 | 878 | 1 | 878 | 132 | 132 | 81 | 1 | 16 | 17 | 52 |
| 16 | HSAVP17 | 209277 09/18/97 | Uni-ZAP XR | 26 | 850 | 1 | 850 | 69 | 69 | 82 | 1 | 18 | 19 | 44 |
| 17 | HSIEA14 | 209277 09/18/97 | Uni-ZAP XR | 27 | 788 | 1 | 788 | 141 | 141 | 83 | 1 | 22 | 23 | 60 |
| 18 | HSNAQ47 | 209277 09/18/97 | Uni-ZAP XR | 28 | 838 | 1 | 838 | 80 | 80 | 84 | 1 | 21 | 22 | 253 |
| 18 | HSNAQ47 | 209277 09/18/97 | Uni-ZAP XR | 64 | 848 | 1 | 848 | 85 | 85 | 120 | 1 | 21 | 22 | 24 |
| 19 | HODDN65 | 209277 09/18/97 | Uni-ZAP XR | 29 | 755 | 1 | 755 | 251 | 251 | 85 | 1 | 14 | 15 | 20 |
| 20 | HPEAD79 | 209277 09/18/97 | Uni-ZAP XR | 30 | 813 | 1 | 813 | 51 | 51 | 86 | 1 | 15 | 16 | 41 |
| 21 | HRDED19 | 209277 09/18/97 | Uni-ZAP XR | 31 | 513 | 1 | 513 | 75 | 75 | 87 | 1 | 20 | 21 | 47 |
| 22 | HSAYS89 | 209277 09/18/97 | Uni-ZAP XR | 32 | 576 | 1 | 576 | 94 | 94 | 88 | 1 | 15 | 16 | 43 |
| 23 | HTODK73 | 209277 09/18/97 | Uni-ZAP XR | 33 | 1019 | 4 | 1019 | 43 | 43 | 89 | 1 | 23 | 24 | 59 |
| 24 | HSVAM10 | 209277 09/18/97 | Uni-ZAP XR | 34 | 433 | 1 | 433 | 46 | 46 | 90 | 1 | 27 | 28 | 51 |
| 25 | HSNBN57 | 209277 09/18/97 | Uni-ZAP XR | 35 | 642 | 1 | 642 | 198 | 198 | 91 | 1 | 20 | 21 | 31 |
| 26 | HSVBD22 | 209277 09/18/97 | Uni-ZAP XR | 36 | 667 | 1 | 667 | 61 | 61 | 92 | 1 | 24 | 25 | 35 |
| 27 | HSAWA27 | 209277 09/18/97 | Uni-ZAP XR | 37 | 654 | 1 | 654 | 319 | 319 | 93 | 1 | 29 | 30 | 49 |
| 28 | HSFAH43 | 209277 09/18/97 | Uni-ZAP XR | 38 | 731 | 1 | 731 | 191 | 191 | 94 | 1 | 22 | 23 | 24 |
| 29 | HSPAA60 | 209277 09/18/97 | pSport1 | 39 | 378 | 1 | 378 | 198 | 198 | 95 | 1 | 45 | 46 | 46 |
| 30 | HFAEF57 | 209277 09/18/97 | Uni-ZAP XR | 40 | 642 | 1 | 642 | 232 | 232 | 96 | 1 | 42 | 43 | 86 |
| 31 | HEGAH43 | 209277 09/18/97 | Uni-ZAP XR | 41 | 442 | 1 | 442 | 29 | 29 | 97 | 1 | 20 | 21 | 111 |
| 32 | HAGDG59 | 209277 09/18/97 | Uni-ZAP XR | 42 | 1734 | 44 | 1717 | 124 | 124 | 98 | 1 | 18 | 19 | 300 |
| 33 | HNGBX63 | 209277 09/18/97 | Uni-ZAP XR | 43 | 517 | 1 | 517 | 120 | 120 | 99 | 1 | 15 | 16 | 104 |
| 34 | HE2AG50 | 209277 09/18/97 | Uni-ZAP XR | 44 | 486 | 1 | 486 | 19 | 19 | 100 | 1 | 32 | 33 | 43 |
| 35 | HCUIN80 | 209277 09/18/97 | ZAP Express | 45 | 826 | 1 | 826 | 106 | 106 | 101 | 1 | 16 | 17 | 49 |

TABLE 1-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 36 | HADCL29 | 209277 09/18/97 | pSport1 | 46 | 694 | 1 | 694 | 248 | 248 | 102 | 1 | 16 | 17 | 47 |
| 37 | HAPPS89 | 209277 09/18/97 | Uni-ZAP XR | 47 | 856 | 1 | 856 | 54 | 54 | 103 | 1 | 29 | 30 | 99 |
| 38 | HFGAH44 | 209277 09/18/97 | Uni-ZAP XR | 48 | 1643 | 1 | 164334 | 34 | 104 | 1 | 20 | 21 | 58 | |
| 39 | HFIHZ96 | 209277 09/18/97 | pSport1 | 49 | 709 | 1 | 709 | 39 | 39 | 105 | 1 | 24 | 25 | 64 |
| 40 | HFJUR10 | 209277 09/18/97 | pSport1 | 50 | 541 | 1 | 541 | 50 | 50 | 106 | 1 | 22 | 23 | 44 |
| 41 | HLDNA86 | 209277 09/18/97 | pCMVSport 3.0 | 51 | 720 | 1 | 717 | 45 | 45 | 107 | 1 | 31 | 32 | 92 |
| 42 | HNGAN75 | 209277 09/18/97 | Uni-ZAP XR | 52 | 979 | 1 | 979 | 41 | 41 | 108 | 1 | 25 | 26 | 25 |
| 43 | HCUIO20 | 209277 09/18/97 | ZAPExpress | 53 | 380 | 1 | 380 | 43 | 43 | 109 | 1 | 19 | 20 | 67 |
| 44 | HLTEF12 | 209277 09/18/97 | Uni-ZAP XR | 54 | 2023 | 624 | 1498 | 686 | 686 | 110 | 1 | 21 | 22 | 44 |
| 45 | HCFBJ91 | 209277 09/18/97 | pSport1 | 55 | 885 | 1 | 885 | 61 | 61 | 111 | 1 | 20 | 21 | 52 |
| 46 | HHFHP90 | 209277 09/18/97 | Uni-ZAP XR | 56 | 1106 | 1 | 1106 | 42 | 42 | 112 | 1 | 14 | 15 | 43 |
| 47 | HLYCQ48 | 209277 09/18/97 | pSport1 | 57 | 764 | 1 | 764 | 58 | 58 | 113 | 1 | 40 | 41 | 64 |
| 48 | HHLAB07 | 209277 09/18/97 | pBluescript SK- | 58 | 738 | 1 | 738 | 108 | 108 | 114 | 1 | 34 | 35 | 69 |
| 49 | HFOXE30 | 209277 09/18/97 | pSport1 | 59 | 441 | 1 | 441 | 38 | 38 | 115 | 1 | 18 | 19 | 53 |
| 50 | HBJEL68 | 209277 09/18/97 | Uni-ZAP XR | 60 | 784 | 1 | 784 | 109 | 109 | 116 | 1 | 33 | 34 | 41 |
| 50 | HBJEL68 | 209277 09/18/97 | Uni-ZAP XR | 65 | 769 | 1 | 769 | 111 | 111 | 121 | 1 | | | 26 |
| 51 | HFOXA73 | 209277 09/18/97 | pSport1 | 61 | 540 | 1 | 540 | 25 | 25 | 117 | 1 | 17 | 18 | 52 |
| 51 | HFOXA73 | 209277 09/18/97 | pSport1 | 66 | 539 | 1 | 539 | 15 | 15 | 122 | 1 | | | 17 |
| 52 | HFJUR35 | 209277 09/18/97 | pSport1 | 62 | 604 | 1 | 604 | 42 | 42 | 118 | 1 | 31 | 32 | 70 |
| 53 | HFPDE86 | 209277 09/18/97 | Uni-ZAP XR | 63 | 752 | 1 | 752 | 300 | 300 | 119 | 1 | | | 16 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep." The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragment specified as described herein.

As a practical matter, whether any particular nucleic acid molecule or polypeptide is at least 90%, 95%, 96%, 97%, 99% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251– 1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn- forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37–767–778 (1984); Sutcliffe, J. G. et al., Science 219:660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host- mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641, 670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library) .) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity , and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological ample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method.. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table I and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library Plasmid | Corresponding Deposited |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ®2.1 | pCR ®2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 µl of reaction mixture with 0.5 ug of the above cDNA template. A convenient reaction mixture is 1.5–5 mM MgCl$_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7) :1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C.. Human, mouse, and hamster DNA is used as template in addition to a somatic cell hybrid panel containing individual chromosomes or chromosome fragments (Bios, Inc). The reactions is analyzed on either 8% polyacrylamide gels or 3.5 % agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The ON culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-I Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five μg of a plasmid containing the polynucleotide is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One μg of BaculoGold™ virus DNA and 5 μg of the plasmid are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μl Ci of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991) .) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 mM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)
Human IgG Fc Region:
GGGATCCGGAGCCCAAATCTTCTGA-
  CAAAACTCACACATGCCCACCGTGC-
  CCAGCACCTGAATTCGAGGGTGCACCGT-
  CAGTCTTCCTCTTCCCCCCAAAACCCAAGGACA
  CCCTCATGATCTCCCGGACTCCTGAGGT-
  CACATGCGTGGTGGTGGACGTAAGCCAC-
  GAAGACCCTGAGGTCAAGTTCAACTGG-
  TACGTGGACGGCGTGGAGGTGCATAATGCCAAG
  ACAAAGCCGCGGGAGGAGCAGTACAA-
  CAGCACGTACCGTGTGGTCAGCGTCCT-
  CACCGTCCTGCACCAGGACTGGCTGAATGG
  CAAGGAGTACAAGTGCAAGGTCTCCAACAAAG
  CCCTCCCAACCCCCATCGAGAAAACCATCTC
  CAAAGCCAAAGGGCAGCCCCGAGAACCA-
  CAGGTGTACACCCTGCCCCCATCCCGG-
  GATGAGCTGACCAAGAACCAGGTCAGC-
  CTGACCTGCCTGGTCAAAGGCTTCTATCCAAGC
  GACATCGCCGTGGAGTGGGAGAGCAATGGG
  CAGCCGGAGAACAACTACAAGACCACGCCTC
  CCGTGCTGGACTCCGACGGCTCCTTCT-
  TCCTCTACAGCAAGCTCACCGTGGACAA-
  GAGCAGGTGGCAGCAGGGGAACGTCTTCTCATG
  CTCCGTGATGCATGAGGCTCTGCACAAC-
  CACTACACGCAGAAGAGCCTCTCCCT-
  GTCTCCGGGTAAATGAGTGCGACGGC-
  CGCGACTCTAGAGGAT (SEQ ID NO:1)

Example 10

Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17–516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5 ml DMEM(Dulbecco's Modified Eagle Medium)(with 4.5 G/L glucose and L-glutamine (12-604F Biowhittaker))/10% heat inactivated FBS(14–503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either I %BSA in DMEM with 1×penstrep, or CHO-5 media (116.6 mg/L of CaC12 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L- Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/mi of L-Leucine; 163.75 mg/ml of L-Lysine HCL; 32.34 mg/ml of L-Methionine; 68.48 mg/ml of L-Phenylalanine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2$H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1×penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 m appropriate media to each well. Incubate at 37° C. for 45 or 72 hours depending on the media used: 1%BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995) .) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs | | | | STATS | GAS (elements) or ISRE |
| --- | --- | --- | --- | --- | --- | --- |
| | tyk2 | Jak1 | Jak2 | Jak3 | | |
| IFN family | | | | | | |
| IFN-a/B | + | + | − | − | 1,2,3 | ISRE |
| IFN-g | | + | + | − | 1 | GAS (IRF1 > Lys6 > IFP) |
| Il-10 | + | ? | ? | − | 1,3 | |
| gp130 family | | | | | | |
| IL-6 (Pleiotrophic) | + | + | + | ? | 1,3 | GAS (IRF1 > Lys6 > IFP) |
| Il-11 (Pleiotrophic) | ? | + | ? | ? | 1,3 | |
| OnM (Pleiotrophic) | ? | + | + | ? | 1,3 | |
| LIF (Pleiotrophic) | ? | + | + | ? | 1,3 | |
| CNTF (Pleiotrophic) | −/+ | + | + | ? | 1,3 | |
| G-CSF (Pleiotrophic) | ? | + | ? | ? | 1,3 | |
| IL-12 (Pleiotrophic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |

-continued

| Ligand | JAKs | | | | STATS | GAS (elements) or ISRE |
| --- | --- | --- | --- | --- | --- | --- |
| | tyk2 | Jak1 | Jak2 | Jak3 | | |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS(B-CAS > IRF1 = IFP >> Ly6) |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used 0instead. The 5' primer also contains 18bp of sequence complementary to the SV40 early promoter sequence and is flanked with an XhoI site. The sequence of the 5' primer is:

5':GCGCCTCGAGATTTCCCCGAAATCTA-GATTTCCCCGAAATGATTTCCCCGAAAT-GATTTCCCCGAAATATCTGCCATCTCAATTAG:3' (SEQ ID NO:3)

The downstream primer is complementary to the SV40 promoter and is flanked with a Hind III site: 5':GCG-GCAAGCTTTTTGCAAAGCCTAGGC:3' (SEQ ID NO:4).

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

5':CTCGAGATTTCCCCGAAATCTAGATTTC-CCCGAAATGATTTCCCCGAAATGATTTC-CCCGAAATATCTGCCATCTCAATTAGT-CAGCAACCATAGTCCCGCCCCTAACTCCGCCCAT CCCGCCCCTAACTCCGCCCAGTTCCGC-CCATTCTCCGCCCCATGGCTGACTAATTTTTTT TATTTATGCAGAGGCCGAGGCCGCCTCG-GCCTCTGAGCTATTCCAGAAGTAGTGAGGAGGC TTTTTTGGAGGCCTAGGCTTTTGCAAAAAGCTT:3' (SEQ ID NO:5)

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, II-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-Throughput Screening Assay for T-cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+Th 1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-Throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2\times10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871

(1991)) can be PCR amplified from human genomic DNA using the following primers:
5' GCGCTCGAGGGATGACAGCGATAGAACCCCGG-3' (SEQ ID NO:6)
5' GCGAAGCTTCGCGACTCCCCGGATCCGCCTC-3' (SEQ ID NO:7)

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (InhibitorκB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-κB would be useful in treating diseases. For example, inhibitors of NF-κB could be used to treat those diseases related to the acute or chronic activation of NF-κB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:
5': G C G G C C T C G A G G G G A C T T T C C C G G G-GACTTTCCGGGGACTTTCCGGGACTTTC-CATCCTGCCATCTCAATTAG:3' (SEQ ID NO:9)

The downstream primer is complementary to the 3' end of the SV40 promoter and is flanked with a Hind III site:
5':GCGGCAAGCTTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:
5': C T C G A G G G G A C T T T C C C G G G G A C T T T C-CGGGGACTTTCCGGGACTTTCCATCTGC-CATCTCAATTAGTCAGCAACCATAGTC-CCGCCCCTAACTCCGCCCATCCCGCCCCTAACTC CGCCCAGTTCCGCCCATTCTCCGCCCCATGGCT GACTAATTTTTTTATTTATGCAGAGGC-CGAGGCCGCCTCGGCCTCTGAGCTATTC-CAGAAGTAGTGAGGAGGCTTTTTTGGAG-GCCTAGGCTTTTGCAAAAAGCTT:3' (SEQ ID NO:10)

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κB/SV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1,1, 10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP 400) according to the following general procedure. The Tropix Phospho-light Kit supplies the Dilution, Assay, and Reaction Buffers used below.

Prime a dispenser with the 2.5×Dilution Buffer and dispense 15 µl of 2.5×dilution buffer into Optiplates containing 35 μl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul. of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/mi with HBSS in a 50-ml conical tube. 4 ul of 1 mg/ml fluo-4 solution in 10% pluronic acid DMSO is added to each ml of cell suspension. The tube is then placed in a 37° C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo4 . The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca^{++}$ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with FBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 MM Na4P207 and a cocktail of protease inhibitors (#1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 mM ATP/50 mM $MgCl_2$), then 10 ul of 5×Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (100 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–59° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–41 1, Tsurumi Y. et al. (1996) Circulation 94(12):3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Feigner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that nonreplicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 28

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 29

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated protein comprising amino acid residues 19 to 98 of SEQ ID NO:73.

2. The isolated protein of claim 1 which comprises amino acid residues 2 to 98 of SEQ ID NO:73.

3. The isolated protein of claim 1 which comprises amino acid residues 1 to 98 of SEQ ID NO:73.

4. The protein of claim 1 which comprises a heterologous polypeptide sequence.

5. A composition comprising the protein of claim 1 and a pharmaceutically acceptable carrier.

6. An isolated protein produced by the method comprising:
   (a) expressing the protein of claim 1 by a cell; and
   (b) recovering said protein.

7. The isolated protein of claim 6, wherein sad cell is isolated from recombinant cell culture.

8. The isolated protein of claim 6, wherein said cell is isolated from a biological sample.

9. An isolated protein comprising the amino acid sequence of the secreted portion of the polypeptide encoded by the HPEAD48 cDNA contained in American Type Culture Collection ("ATCC") Deposit No. 209277.

10. The isolated protein of claim 9 which comprises the amino acid sequence of the complete polypeptide encoded by the HPEAD48 cDNA contained in ATCC Deposit No. 209277, excepting the N-terminal methionine.

11. The isolated protein of claim 9 which comprises the amino acid sequence of the complete polypeptide encoded by the HPEAD48 cDNA contained in ATCC Deposit No. 209277.

12. The protein of claim 9 which comprises a heterologous polypeptide sequence.

13. A composition comprising the protein of claim 9 and a pharmaceutically acceptable carrier.

14. An isolated protein produced by the method comprising:
   (a) expressing the protein of claim 9 by a cell; and
   (b) recovering said protein.

15. The isolated protein of claim 14, wherein said cell is isolated from recombinant cell culture.

16. The isolated protein of claim 14, wherein said cell is isolated from a biological sample.

17. An isolated protein comprising a fragment of SEQ ID NO:73, wherein said fragment generates an antibody that specifically binds to a polypeptide having an amino acid sequence consisting of amino acid residues 19 to 98 of SEQ ID NO:73.

18. The isolated protein of claim 17, wherein said fragment comprises at least 30 contiguous amino acid residues of amino acid residues 19 to 98 of SEQ ID NO:73.

19. The isolated protein of claim 17, wherein said fragment comprises at least 50 contiguous amino acid residues of amino acid residues 19 to 98 of SEQ ID NO.73.

20. The protein of claim 17 which further comprises a heterologous polypeptide sequence.

21. A composition comprising the protein of claim 17 and a pharmaceutically acceptable carrier.

22. An isolated protein produced by the method comprising:
   (a) expressing the protein of claim 17 by a cell; and
   (b) recovering said protein.

23. The isolated protein of claim 22, wherein said cell is isolated from recombinant cell culture.

24. The isolated protein of claim 22, wherein said cell is isolated from a biological sample.

25. An isolated protein comprising a fragment of the secreted portion of the polypeptide encoded by the HPEAD48 cDNA contained in ATCC Deposit No. 209277, wherein said fragment generates an antibody that specifically binds to the secreted portion of the polypeptide encoded by the HPEAD48 cDNA contained in ATCC Deposit No. 209277.

26. The isolated protein of claim 25, wherein said fragment comprises at least 30 contiguous amino acid residues of the secreted portion of the polypeptide encoded by the HPEAD48 cDNA contained in ATCC Deposit No. 209277.

27. The isolated protein of claim 25, wherein said fragment comprises at least 50 contiguous amino acid residues of the secreted portion of the polypeptide encoded by the HPEAD48 cDNA contained in ATCC Deposit No. 209277.

28. The protein of claim 25 which further comprises a heterologous polypeptide sequence.

29. A composition comprising the protein of claim 25 and a pharmaceutically acceptable carrier.

30. An isolated protein produced by the method comprising:
   (a) expressing the protein of claim 25 by a cell; and
   (b) recovering said protein.

31. The isolated protein of claim 30, wherein said cell it isolated from recombinant cell culture.

32. The isolated protein of claim 30, wherein said cell is isolated from a biological sample.

33. An isolated protein comprising a fragment of SEQ ID NO:73, wherein said fragment generates an antibody that specifically binds to a polypeptide having an amino acid sequence consisting of amino acid residues 1 to 98 of SEQ ID NO:73.

34. The isolated protein of claim 33, wherein said fragment comprises at least 30 contiguous amino acid residues of amino acid residues 1 to 98 of SEQ ID NO:73.

35. The isolated protein of claim 33, wherein said fragment comprises at least 50 contiguous amino acid residues of amino acid residues 1 to 98 of SEQ ID NO:73.

36. The protein of claim 33 which further comprises a heterologous polypeptide sequence.

37. A composition comprising the protein of claim 33 and a pharmaceutically acceptable carrier.

38. An isolated protein produced by the method comprising:
   (a) expressing the protein of claim 33 by a cell; and
   (b) recovering said protein.

39. The isolated protein of claim 38, wherein said cell is isolated from recombinant cell culture.

40. The isolated protein of claim 38, wherein said cell is isolated from a biological sample.

41. An isolated protein comprising a fragment of the complete polypeptide encoded by the HPEAD48 cDNA contained in ATCC Deposit No. 209277, wherein said fragment generates an antibody that specifically binds to the complete polypeptide encoded by the HPEAD48 cDNA contained in ATCC Deposit No. 209277.

42. The isolated protein of claim 41, wherein said fragment comprises at least 30 contiguous amino acid residues of the complete polypeptide encoded by the HPEAD48 cDNA contained in ATCC Deposit No 209277.

43. The isolated protein of claim 41, wherein said fragment comprises at least 50 contiguous amino acid residues of the complete polypeptide encoded by the HPEAD48 cDNA contained in ATCC Deposit No. 209277.

44. The protein of claim 41 which further comprises a heterologous polypeptide sequence.

45. A composition comprising the protein of claim 41 and pharmaceutically acceptable carrier.

46. An isolated protein produced by the method comprising:

(a) expressing the protein of claim 41 by a cell; and
(b) recovering said protein.

47. The isolated protein of claim 46, wherein said cell is isolated from recombinant cell culture.

48. The isolated protein of claim 46, wherein said cell is isolated from a biological sample.

* * * * *

UNITED STATES PATENT AND TRADEMARK OFFICE
CERTIFICATE OF CORRECTION

PATENT NO. : 6,433,139 B1 Page 1 of 1
APPLICATION NO. : 09/288143
DATED : August 13, 2002
INVENTOR(S) : Brewer et al.

It is certified that error appears in the above-identified patent and that said Letters Patent is hereby corrected as shown below:

In Claim 31, delete "wherein said cell it isolated" and insert -- wherein said cell is isolated".

Signed and Sealed this

Eighteenth Day of July, 2006

JON W. DUDAS
*Director of the United States Patent and Trademark Office*

SEQUENCE LISTING

<160> NUMBER OF SEQ ID NOS: 219

<210> SEQ ID NO 1
<211> LENGTH: 733
<212> TYPE: DNA
<213> ORGANISM: Homo sapiens

<400> SEQUENCE: 1

| | | | | | |
|---|---|---|---|---|---|
| gggatccgga | gcccaaatct | tctgacaaaa | ctcacacatg | cccaccgtgc | ccagcacctg | 60 |
| aattcgaggg | tgcaccgtca | gtcttcctct | tcccccaaa | acccaaggac | accctcatga | 120 |
| tctcccggac | tcctgaggtc | acatgcgtgg | tggtggacgt | aagccacgaa | gaccctgagg | 180 |
| tcaagttcaa | ctggtacgtg | gacggcgtgg | aggtgcataa | tgccaagaca | aagccgcggg | 240 |
| aggagcagta | caacagcacg | taccgtgtgg | tcagcgtcct | caccgtcctg | caccaggact | 300 |
| ggctgaatgg | caaggagtac | aagtgcaagg | tctccaacaa | agccctccca | accccatcg | 360 |
| agaaaaccat | ctccaaagcc | aaagggcagc | cccgagaacc | acaggtgtac | accctgcccc | 420 |
| catcccggga | tgagctgacc | aagaaccagg | tcagcctgac | ctgcctggtc | aaaggcttct | 480 |
| atccaagcga | catcgccgtg | gagtgggaga | gcaatgggca | gccggagaac | aactacaaga | 540 |
| ccacgcctcc | cgtgctggac | tccgacggct | ccttcttcct | ctacagcaag | ctcaccgtgg | 600 |
| acaagagcag | gtggcagcag | gggaacgtct | tctcatgctc | cgtgatgcat | gaggctctgc | 660 |
| acaaccacta | cacgcagaag | agcctctccc | tgtctccggg | taaatgagtg | cgacggccgc | 720 |
| gactctagag | gat | | | | | 733 |

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3

| | | | | | |
|---|---|---|---|---|---|
| gcgcctcgag | atttccccga | aatctagatt | tccccgaaat | gatttccccg | aaatgatttc | 60 |
| cccgaaatat | ctgccatctc | aattag | | | | 86 |

<210> SEQ ID NO 4
<211> LENGTH: 27
<212> TYPE: DNA
<213> ORGANISM: Homo sapiens

<400> SEQUENCE: 4

| | | |
|---|---|---|
| gcggcaagct | ttttgcaaag | cctaggc | 27 |

<210> SEQ ID NO 5
<211> LENGTH: 271

<212> TYPE: DNA
<213> ORGANISM: Homo sapiens

<400> SEQUENCE: 5
ctcgagattt ccccgaaatc tagatttccc cgaaatgatt tccccgaaat gatttccccg    60
aaatatctgc catctcaatt agtcagcaac catagtcccg ccctaactc cgcccatccc   120 gcccctaact ccgcccagtt ccgcccattc tccgccccat ggctgactaa ttttttttat   180
ttatgcagag gccgaggccg cctcggcctc tgagctattc cagaagtagt gaggaggctt   240
ttttggaggc ctaggctttt gcaaaaagct t                                  271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaacccc gg                                  32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c                                   31

<210> SEQ ID NO 8
<211> LENGTH: 12
<212> TYPE: DNA
<213> ORGANISM: Homo sapiens

<400> SEQUENCE: 8
ggggactttc cc                                                        12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt ccggggact ttcgggact ttccatcctg     60 ccatctcaat tag                                                       73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg gactttccg ggactttcca tctgccatct    60
caattagtca gcaaccatag tcccgccct aactccgccc atcccgcccc taactccgcc    20
cagttccgcc cattctccgc cccatggctg actaattttt tttatttatg cagaggccga    80
ggccgcctcg gcctctgagc tattccagaa gtagtgagga ggctttttg gaggcctagg    40 cttttgcaaa aagctt                                                    56

<210> SEQ ID NO 11
<211> LENGTH: 680
<212> TYPE: DNA

<213> ORGANISM: Homo sapiens

<400> SEQUENCE: 11

```
ggcacgagct tggaggtcta ctggcagact tccttctctc cagaaaaatc ctcagactca      60
tcaccatcag gaaactcttc actgccattg gggttctctt cccatccgtg atcctcgtgt     120
ccctgccctg ggtcagatcc agccacagca tgaccatgac cttcttggtg ctgtcttctg     180
ccatcagcag cttctgtgaa tcaggagccc ttgttaactt cttggatatt gctcctcggt     240
acactggctt tctcaaagga ctattgcaag tctttgcaca catagctgga gccatctctc     300
ctactgctgc tggatttttc atcagtcagg attcagagtt tggttggaga aatgtcttct     360
tgcttcagc tgctgttaac atatcgggcc tggttttcta cctcatcttt ggccgagcag     420
atgtgcagga ctgggctaaa gagcagacat tcacccacct ctgagcaaac cgagagatgt     480
gctagatcct ggtgcttagt tcatcattgt tttccctcac agacatttct ctttcatgcc     540
tgcttgactg ataagccatt agctagaccc tgactatgta acgctaaaga ttttaccatg     600
cctggaaatt ttacagggga agaaaacacg ctagttattt aactgcaaaa aaaaaaaaa     660
aaaaaaaaaa aaaactcgta                                                680
```

<210> SEQ ID NO 12
<211> LENGTH: 741
<212> TYPE: DNA
<213> ORGANISM: Homo sapiens
<220> FEATURE:
<221> NAME/KEY: SITE
<222> LOCATION: (35)
<223> OTHER INFORMATION: n equals a,t,g, or c
<220> FEATURE:
<221> NAME/KEY: SITE
<222> LOCATION: (39)
<223> OTHER INFORMATION: n equals a,t,g, or c

<400> SEQUENCE: 12

```
aattcggcac gagacccttta ggaacacgga cgcancgtnc ggcattgtca tctacgcagg      60
acatgaaacc aaggctctgc tgaacaacag tgggccccgc tacaagcgca saagctggag     120
aggcagatga actgcgacgt gctctggtgt gtcctgctcc ttgtttgcak gtctctgttt     180
tcagcagtcg gacatggact gtggatatgg cggtatcaag agaagaagtc attatttat     240
gtccccaagt ctgatggaag ctccttatcc ccagtcacag ctgcagttaa ctcatttta     300
acatgatata gttckgcagg ttttgatccc atttccttat acgkttccat tgaaattgtt     360
aaagcatgcc aagtgtactt cattaaccag gacatgcagt tgtatgacga agaaacagac     420
tcgcagctgc agtgccgagc tctgaacatc acggaagact taggacagat acagtacatt     480
ttctcagata aaactggcac tttgacagag aataagatgg ttttccgaag atgcactgtg     540
tctggtgtag aatattctca tgatgcaaat gagggtctat taagagatgc gcagtggtcc     600
acgcggctgg ccggctccat aagtatctcc ttctccggcc tcttgacagg cccctgctgc     660
tttgactcag caccatgcct gtgcttgaag ttctgattaa acggttgttc tgataagtaa     720
aaaaaaaaaa aaaaactcgt a                                              741
```

<210> SEQ ID NO 13
<211> LENGTH: 619
<212> TYPE: DNA
<213> ORGANISM: Homo sapiens

<400> SEQUENCE: 13

```
ggcacgagct ggggcctgtg tgcctccacg ccataatgct ggcagaactg atatttctct      60
```

```
ttaggagtct ccatgggata cttgcctccg caggcaccat aggagcagtg gcagcttggc      120
tgatgagcta taagccagcc ttgtttgggt tcctattcct tctgctgttg cttagcaact      180
ggttggtcaa gtatgaacac aagctcaccc tcccagagcc ccagcaggag gaagagaaac      240
caaagacttc tgaaaacgac tccaagaaca gcaaggccgt gaacacaaaa gaagtcaata      300
gaacgcatgc ctgctttgcc ctccaggacg agatcctcca acggctgttg ttcagtgaaa      360
tgaagatgaa ggtcctagaa aatcagatgt tcatcatatg gaataaaatg aatcaccacg      420
ggcggtcaag cagacatcgg aatttttccca tgaaaaaaca cagaatgagg aggcatgagt      480
caatttgccc caccctgtct gactgtactt cgagttcccc cagctaatga ggycgaggcg      540
ggctggcctc tgccgatgtt accttttacc tcagtaaaac ccagtcacag cctaaaaaaa      600
aaaaaaaaaa aaactcgta                                                  619

<210> SEQ ID NO 14
<211> LENGTH: 611
<212> TYPE: DNA
<213> ORGANISM: Homo sapiens
<220> FEATURE:
<221> NAME/KEY: SITE
<222> LOCATION: (17)
<223> OTHER INFORMATION: n equals a,t,g, or c

<400> SEQUENCE: 14
aggatttcgg cacgagntca gatccaaagc tttttgaaat gattaagtat tgtcttttga       60
aaattctgaa gcaatatcag acattgagag aagctcttgt tgcagcagga aaagaggtta      120
tatggcatgg gcggacaaat gatgaaccag ctcattactg tagcatttgt gaggtggagg      180
tttttaatct gcttttttgtc actaatgaaa gcaatactca aaaaacctac atagtacatt      240
gccatgattg tgcacgaaaa acaagcaaaa gtttggaaaa ttttgtggtg ctcgaacagt      300
acaaaatgga ggacctaatc caagtttatg atcaatttac actagcctcc ccatggccac      360
ccatggacca gtcggcattc acttcctccc ttctgcggcc cataaaagcc ctgggttcag      420
gcagagctga gcagacatca ggtgaccagc tgcagaaagg agctacccac tccagggcct      480
catctctgct gagagctgca gagatgacca gaagacctgc atccagagag gagcttcctg      540
atccagggct attctgtcac tcaataaagc ttctctttgt cttgttaaaa aaaaaaaaaa      600
aaaaactcgt a                                                          611

<210> SEQ ID NO 15
<211> LENGTH: 585
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<220> FEATURE:
<221> NAME/KEY: SITE
<222> LOCATION: (15)
<223> OTHER INFORMATION: n equals a,t,g, or c
<220> FEATURE:
<221> NAME/KEY: SITE
<222> LOCATION: (19)
<223> OTHER INFORMATION: n equals a,t,g, or c
<220> FEATURE:
<221> NAME/KEY: SITE
<222> LOCATION: (29)
<223> OTHER INFORMATION: n equals a,t,g, or c

<400> SEQUENCE: 15
```

-continued

| | |
|---|---|
| gttgnatccc ccccngggnc ttgccaggna atttccggcc accgagggtg attttaactt | 60 |
| tccaatggcg ttttttacctt tcttttagaa aactaatgcg atggatatta atacttgtta | 120 |
| ttgccttgtg gtttattgag cttttggatg tgtggagcac ttgtagtcag cccatttgtg | 180 |
| caaaatggac aaggacagag gctgagggaa gcaagaagtc tttgtcttct gaagggcacc | 240 |
| acatggatct tcctgatgtt gtcattacct cacttcctgg ttcaggagct gaaattctca | 300 |
| aacaactttt tttcaacagt agtgattttc tctacatcag ggttcctaca gcctacattg | 360 |
| atattcctga aactgagttg gaaatcgact catttgtaga tgcttgtgaa tggaagtgtc | 420 |
| agatatccgc agtgggcatt ttcgtttact ccgaggctgg ttgcagtctt tagtccagga | 480 |
| cacaaaatta catttgcaaa acatccatct gcatgaaccc aatagggta aactggccca | 540 |
| atattttgca atgaataagg acaaaaaaaa aaaaaaaaa ctcga | 585 |

<210> SEQ ID NO 16
<211> LENGTH: 1040
<212> TYPE: DNA
<213> ORGANISM: Homo sapiens

<400> SEQUENCE: 16

| | |
|---|---|
| ggcacgaggt gaatcccag cctgaggtcg tgcttaagtg ccacctgctc aagagagaag | 60 |
| gcttcctgcc cgcgcccatg atgtaagtcc ccccagatgc tttccaccat cctgtccttt | 120 |
| gtctgtaatt gcgcttgtcg cttgaacaga atcctaattg tgctgattac atgtttaatt | 180 |
| ttggtctccc ctgtaagaca ggcatgcttt ttggaggcag ggactgaatg tcattcacat | 240 |
| ctgtgctcct agggtctaat acatgatggt gcattgtaag tattcagtat ataacttgtt | 300 |
| gaataaatgg atcgggttta gcattttccc ccattggacc tggattgacc tggaaattgg | 360 |
| tggactgaac ctgcaagtag agattaaagg acctaacaac tgtagagtgg ctggtgaagg | 420 |
| tagatataag tgcagtaagg gagggagtcg ttgatgtkgt tttggttcgt agtgcagaat | 480 |
| aaagctactt atgaaatat acgactccta ctcttagttt ctgctttgat gtggtwackg | 540 |
| ctgttgttta gcgtaagcat ataaacaaat cactggctta gtgggttaat ttttcttctc | 600 |
| ttttgttaaa cagctgagtt tttgctgttt tcaaagttag ccaaaaattc catttttcatg | 660 |
| tttaaatgat ttagaaaaat cattttttctt taaaaaataa cagtacataa aaagaaaaca | 720 |
| ttctcggctg ggcgcggtgg ctcacgcctg taacccagca ctttgggagg ctgagacagg | 780 |
| cagttcacct gaggtcagga gtttgagacc agcctgacca acatggagaa actccgtctc | 840 |
| tactaaaaac acaaaaattt tagccgggcg ttgtgccacg ttcctgtaat cccagctact | 900 |
| cgggaggctg aggcaggaga atcgcttgaa cccgggaggc agaggttgca gtgagccgag | 960 |
| atcgtgtcat tgcactccag cctgggcaac aagagcgaaa ctccatctca aaaataaaa | 1020 |
| aaaaaaaaaa aaaactcgta | 1040 |

<210> SEQ ID NO 17
<211> LENGTH: 625
<212> TYPE: DNA
<213> ORGANISM: Homo sapiens
<220> FEATURE:
<221> NAME/KEY: SITE
<222> LOCATION: (6)
<223> OTHER INFORMATION: n equals a,t,g, or c
<220> FEATURE:
<221> NAME/KEY: SITE
<222> LOCATION: (11)
<223> OTHER INFORMATION: n equals a,t,g, or c
<220> FEATURE:
<221> NAME/KEY: SITE

```
<222> LOCATION: (43)
<223> OTHER INFORMATION: n equals a,t,g, or c
<220> FEATURE:
<221> NAME/KEY: SITE
<222> LOCATION: (46)
<223> OTHER INFORMATION: n equals a,t,g, or c
<220> FEATURE:
<221> NAME/KEY: SITE
<222> LOCATION: (68)
<223> OTHER INFORMATION: n equals a,t,g, or c

<400> SEQUENCE: 17
ttaccntcac ntaaggggaa caaaagctgg agctccaccg cgntgncggc cgctctagaa      60
ctagtggntc ccccgggctg caggaattcg gcacgagctc gtgccgaatt cggcacgagc    120
agcaacagca acacaggtgt ggagttgaca gacaggtaca ttgaaccaga gctgtgattt    180
agacaagcca ggaacctcat gtatgtccat aatgctgctg acattcactc ttcacttccc    240
cagcacatta ctgtcatatc tcccagagaa ttatgtcata ccttctctct tctcaaacct    300
gcaacactgg atctgctgtg ttcactctca gttggtaacc tgtttcgtat ttcagagaga    360
caatgtaagc actgagaaga gaactcttgc acactccaac acctcatctg ccacctctca    420
ccatctgtct ccttgtacta ctggagatgg tctgccctcc tcctggggag gccaaactca    480
tccacttctg cactagattc cgtcctcttt tatcttccct acatcatgtg ttttccttct    540
atactcatca ttccttttag caataaatat ctttaaaaaa aaaactcgag gggggcccg    600
gtacccaatt cgccctatag tggag                                          625

<210> SEQ ID NO 18
<211> LENGTH: 819
<212> TYPE: DNA
<213> ORGANISM: Homo sapiens

<400> SEQUENCE: 18
aattcggcac gagggaaact catgcacaaa caaaacagca catgctgtac tcacagccag      60
ttacacagaa tgctcatgca tgcatctgtt gcttattaat tttcttcctg ctgtttgtat    120
cattcttttg aagaatctcc agcaagcttt gtgctttgcc caattgttta taatgtctat    180
aaatcagggg cttggaccaa atgaaatgtc ttagtagtgt ttgcaaaata tttggatatt    240
ctgattgcgt tttattttcc cagctttaga aaacatatag atagcctctg ttgggaactt    300
atattctcgt tactccttgt ctcttttctt ttttcaggaa ttggtcactc tttcagccaa    360
ctcgtaggtt caaacaatgt ttacatgtag tgctcagttt gttttaactt cckgctgtag    420
acattgacag tttttycttc cyaagagtct tatgaatagg caacaaacca aaaccaaaac    480
aggcaagtcc catctattac tacgtactta caaatccagg tgaaagtgct tggtgaacag    540
tctatgtttt agcaactgtt ttttaacgtt tggttgtgac attttttaac aacagccatt    600
gttcaattgt taaactatgt ttggatttga ggtctgaatg agctgaattc aaaatatggg    660
acttttatt agaaccctg gtaaagtgga cactggggaa aaagcccaag atttcatgtg      720
tttgatttat tgactatgtg cgtcaacagc ctgcttttaa ttctcagagt aaaataaaaa    780
tactcagaat ctaaaaaaaa aaaaaaaaaa aaaactcga                            819

<210> SEQ ID NO 19
<211> LENGTH: 782
<212> TYPE: DNA
<213> ORGANISM: Homo sapiens

<400> SEQUENCE: 19
```

-continued

```
ggcacgaggt ttattccctg tcacccacct tatcccactg tcttattctt agagttgtct    60
ttcagaaacc caaatacaga tcatgtcaca gatactgaga agttccttat tgccttgata   120
aggtgataca taaaaccttta gaatggcttt cagggttctt tactattccg tctggttat   180
cttttacac gtgtcatttg ccactccaaa agttacagga ctaattgcct caacatacca   240
tttcttat gtcttcatgt ttctgctcat gatccttct gcctaatgct tttccacatc   300
ttccatttcc gctttgagga actcctttt ctttcttcaa gatacaatgc ttgcagtctt   360
aatcttccat gacagtgctc tcatagttta gtttaacctc tgcaatagga tatacctcat   420
gattactaca atttatatgt gtttcctttt accaaactct taggaaaaag gagagcctgg   480
gccgggtggg gtggctcacg cctgtagtcc cagcacttgg ggaggccgag gcggaggatc   540
acaaggtcag gagattgaga ccagcctggc caacatagtg aaaccccgtc tctcctaaaa   600
acacaaaaat cagctgggtg tggtggcgcg cgcagctgta atcccagcta ctcaggaggc   660
tgaagycagg agaatcgctt gaaccccgga ggcggggatt gcagtgagcc aggatggcgc   720
cactgcactc cagcttggtg acagcgagat ccgtcttaaa aaaaaaaaaa aaaaactcgt   780
ag                                                                 782
```

<210> SEQ ID NO 20
<211> LENGTH: 655
<212> TYPE: DNA
<213> ORGANISM: Homo sapiens

<400> SEQUENCE: 20

```
gtctgttgtt tactaaaatg aaaattcagt tgaaatgcc actaattcag aaattagtaa    60
atcctattta ttatgtattt taccaattaa tagaatacaa aggtatcata tacaactacc   120
atggaggtgg caggaagaag attgactttt tcaaatggtc ttcatactgg aacagattaa   180
aaaccaagtc ttctttcttt tcctcctgtt aaaactcact tgtgtctcac attaagctcc   240
taaatgtgcc ctctgtttcc ctaggccaga gccagtgtct aacaagtaat gcatttggag   300
ggtcatggcc caacagtcta cattcagcca ggatttagga acttcattcc aatgatcttt   360
gaaggacttg tacaactcta gccagccttt gaagggagta ttttgggaac tgggaagaga   420
tctttctagt cctcccatgg agacagcaag gttatggtga agtttggaat cagataaaac   480
taatggaggc attacatctc taatctaaaa tgaggattat agtctaggtg tggtggcaca   540
cacctgtaat cccatcactt tgggaggcca aggccgagg attgcttgtc caaggagttg   600
gggaccagcc tgggcaacat acagatgcaa aaaaaaaaaa aaaaaaaac tcgta        655
```

<210> SEQ ID NO 21
<211> LENGTH: 798
<212> TYPE: DNA
<213> ORGANISM: Homo sapiens

<400> SEQUENCE: 21

```
ggaaaaatgc agctaattca gctcataact ttaacaatta cacaagtgct tttcctggat    60
accatcatgt ctacatatgt agcagatacg gattatgtgg ttcttcctgt ttcatcccat   120
aaaawattct aaagacattc aaagttgag atttaataaa ataattttta gtactttatc   180
aagggcattc taagtgaatt cgtgctcttt tttttaaacc ataagtacat agcagtaaag   240
aagacaataa ccacatttt tgtgtctctgc ctttatctgt ggtaagctga cagcagtttt   300
acccaccatt gcttctgcac catcagtgca aatgtcaaaa tagtgaaaag gccaggtgca   360
ktggctcaca cctgtggtcc tagcaatttg ggatgctgag gcgggtggtt tacctggtca   420
```

```
ggagtttgag gccagcctgg ccaacatggt gaaaccccat ctctgctgaa aatacaaaga      480
ttagccgggt gtggtgggcg cctgtagtcc cagctactcg ggaggtagac gcaggagaat      540
cgctggaatc cgggaggcgg aggttgcagt gagccgagac cgcgccaaca tggtgaaacc      600
gtgtctctac taaaaataaa aaattagccg agacctggtg gtgggcgcct gtaatcccag      660
ctactcggga agttgaggca ggagaattgc ttaaacccag gagaccgagg ttgcagtgag      720
ctgaaaccac gtcattgcaa tccagcctgg gcaacagagc gagactctgt ctcaaaaaaa      780
aaaaaaaaaa aactcgaa                                                    798

<210> SEQ ID NO 22
<211> LENGTH: 646
<212> TYPE: DNA
<213> ORGANISM: Homo sapiens

<400> SEQUENCE: 22
aggtctttgt ttcaaattgg ttagatggaa ggagaaaagt ggtcaccatt ttaattctca       60
gaagaggaag ttaatcggtg ttctgcatct gactttcacc tccctccttc ctttcctttg      120
tcagttagga taggtgacac ttcttttctt ttacggctat tatcagagat tttgtgttta      180
atagttgctg ggtcacattt tacaagtgca atgactttg atgacctcca tttactttttt      240 cttagctatc ttcatgtcta caaggagtga aaggctataa agcattcagg caggctcctg      300
ttttgatcag cctctccagg tgatcattat acccaagtca aaagtcaat gcactcccca       360 aatgagaaac atatatatat atatatagga aatctccctt ttacaagatc gtagtgcatc      420
tcctgggttt tttcccatcc ttgtgagtca gttagtttgt aattgactct ctaaccagcc      480
ttccaccttc tgttaacctt tattacctat agtcaaaggg acctcaggaa tgcgagagac      540
cccccccsaa actccctgcg gcttttaagt ctcatcttac agcattcccc ctcaaaccta      600
aaaaaaaaaa aaaaaaaaa aaaaaaaaa aaaaaaaaa ctcgta                        646

<210> SEQ ID NO 23
<211> LENGTH: 752
<212> TYPE: DNA
<213> ORGANISM: Homo sapiens

<400> SEQUENCE: 23
gatcaaatcc tgaagtggta catgtcacta ctgttcatag tctctttgct ggaacttggt       60
cctatggccc tactggcaga gaggaaggct atgaaaccca gtctaggcct gcgcctagaa      120
gaagaagaag aagaaacacc ttttgaagaa cagagagcag tctctgtcat accaggrgta      180
cctgtcacat acttgtagaa caaaaataag taacatttta attattgaaa caatgtaaca      240
actttaaaca cagtttcata actaggagtg aatcacccat aatctcatac ccggaacaaa      300
atatctgtta gtatgatgca cctttacata gctgtaatct taagggcat gtacttcctt       360 ctttgctttc ctttttttt tcttcatcc tttccctctc tccctctctc cctctctccc        420
tttctccctt ccttctttct tttcttcctt tctttctgat tttctaactt ccttcttttaa     480 acattccttg atcgtctgtg ggtctggaca gcaacatgga gatcaattag gcgcagcatt      540
ttaaatttgc cctcaagaag ttccactagt gtaagagtag gcaagtaacc aattattaca      600
atagtgggac aagcgctgtg atagaaataa atacagagta ctgtggcagt ccttacccag      660
aaaaagatat ctagggtaga tggtatctga actgagaatt aaagaataaa tagaagatag      720
catggcaaaa aaaaaaaaaa aaaaactcgt ag                                    752
```

```
<210> SEQ ID NO 24
<211> LENGTH: 815
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c

<400> SEQUENCE: 24
ngcttcaccg tgcactttca tgttagagag atcttaaact tcaagaacca acctctgcta      60
gcttgagaca ttttttcctr cagcttcctc acctctctca gccttcatgg aattgaagag     120
agttagggcc ttgttctgga ttaggtttg gcttaaatga attttgtggc tgctctgatc      180
ttctctccag accaatacaa ctttatatta aggataaggc tgttttggtt tcttatcatt     240
tgtgtgttga gtggaatatt acttttattt ccttcgagaa ccttttcttt gcatccataa     300
cttgggctaa ctatggtgca agasgcctag cttttggcct atctctgctt tccacatgcc     360
tttctcacta agtataataa tttctagctt ttgagttaaa gtgaaagacg tgcaacccat     420
ccttttactt gaacccttag aggccattgt atggttaata tatggcctaa tttcaatatt     480
gtgtctcaga aatagggac gcccgagtag agggagagag atgggaaaat agcagtcaat     540
ggtgtagtca gaacacatac agcatttact aagttcacca tcttatatgg gtgcggttag     600
tggtgctcca aaacaattac aatacaaaca tcaaagatta ctgagcacag atcaccaagt     660
agaaacaatt ataatgaaaa aatagggaat attgcaagaa ttaccaaaat gtgacacaga     720
gacatgctgt aaaaatgatc ccaataaact tgcttaatgc acagttgcca caagctttca     780
atttgttaac aaaaaaaaaa aaaaaaaaac tcgta                                815

<210> SEQ ID NO 25
<211> LENGTH: 878
<212> TYPE: DNA
<213> ORGANISM: Homo sapiens

<400> SEQUENCE: 25
gcaacagatg aattttgggt gacacaaaca ttcagaccat agcagtcact atctaacaac      60
aggtggatgg gacgtttgtc taaaccgaat tgtacttcgg taacaggatc atataaggac     120
aaatttaacc aatgtctttt ttagttttta gtttcttttg ttttggtttt agcaactcta     180
gattttctag agactatcaa cattacctt ctttgctctc cagcccccat gcccagaaaa     240
gaaataagat tattagggag tcaagcatct cggctcttct tacctcttag ggtagtaaat     300
tgcttttgt atgcgagtgg ttttgcgtat gtgaagataa ttttgagata ggagtagaat     360
gccctgaaga taatgcttat gttttaaaga taataagcca acacagtgaa cggaataagc     420
tgcactggac ctgaggagtg aggttaaata gggaagtaag acaccacctg gagacagtat     480
tgctcaagac tgaaagtgga tgagggttgc aaagctgttt gcacagtgct tctgaagcat     540
catggcagcc tggggaattt cccatgctga gcttgcctgg agtatgtgtg tgtatgcatg     600
catgtgtatg tgcattcgtt tgtgtgtgaa ggaagggag cagagctgct ggcttagtca     660
gctacctttg aatgcttctc cctcaacaga ggctgagaac cagacccctt gcctttgtcc     720
ctgaattata ttagctcagg ggttcttatg ccatccaaag ataaggacat aagaagaata     780
gggaaagtgc tgggattgca ggtgtgagcc actgtgtctg gtccattatt ttagagggta     840
ctcctactca ttaaaaaaaa aaaaaaaaaa actcgtag                             878
```

```
<210> SEQ ID NO 26
<211> LENGTH: 850
<212> TYPE: DNA
<213> ORGANISM: Homo sapiens

<400> SEQUENCE: 26
gggcaaacat tgtctacaag taataaatgc tttgcataaa tgtgcagaca cacgtgtatg      60
aatgtgctat gcaaataccc ttccttttag aagtatttgt tattcataca ggtgttttag    120
gaagtaaatt gcttaaatct ggtggtcttt ttgatttaac atccttttca ccaatgataa    180
tttgctttag taataaaagt tagtctcttg ttgttactgg aatattgtta attcatcaaa    240
aaaatcaaaa gcctatcatg acaggaatta ttctaataac tctctaaaag gataatcata    300
ataataaatt aactagcaaa gtgacaatcc ctttccttaa ggtgtttatg gcctggtagt    360
gaaaagagaa acctgaagca attacccccat aattacgagg aatacagaat aatcactata    420
atggatgaat ggatggatga tgcagagaag caatgcaatg attaggctta aggaaatcag    480
ggacaacttc acaaggaag gactgtttaa ggagaggctt aaagaatgga ggccaggtgc    540
agtstctcac gcctgtaatc ctagcacttt gggaggctga ggcaggtgaa tcacctgagg    600
ttaggagttc aagaccagcc tagccaacat ggtgaaaccc tgtctctatt aaaaatacaa    660
aaattagccg ggcatggtgg caggcatctg tagaatccca gctacctggg aggctgaggc    720
aggagaatcc cttgaacccg ggagacagaa gttgcagcga gccacgtttg caccactgca    780
ctccagcctg ggcaacagag tgagactctg tcttaaaaaa agaaaaaaa aaaaaaaaa    840 aaaactcgta                                                          850

<210> SEQ ID NO 27
<211> LENGTH: 788
<212> TYPE: DNA
<213> ORGANISM: Homo sapiens

<400> SEQUENCE: 27 gttttttgttg agtataggag ttctttatat actctggata ttaacctctt attagataca      60
tggtttgcaa atattttctc ccattctgta ggttaccttt tcactcttgt ttcctttaat    120
gggcagaagt taagtttgat atggtctcat ttgcctgctt ttgctttcat tgtctgtttt    180
tggtgtcata tccaagaaat cattgccaaa ttcagtgtcg tgatgctttt tcccgaagtt    240
ttcttctagg agttttttcag gtcttatatt taggttttat caactacatt acgtttatg    300 ttgaagaaaa aacackggaa tagaattaat gtttaaactg ataataaatt ttcttccccc    360
acaaaacaaa ccaccctgaa tataaatact gtaaggccac tctgtgtgct tgggaaagtt    420
gactcagagg tgtcagatcc tagtgaaacg attagatttt aaagataaaa gaagtcctct    480
cgggccagga gtggtggctc atgcctgtga tcccagcact tgggaggct gaggcaggca    540 gatcacttga ggccaggagt ttgagaccag cctggccaac atggcaaagc cccatctcta    600
ctaaaaatac aaaacttagc tgggcttggt ggtgcacact tgtaatccca gctacttggg    660
aggctgagtc catgagaatt gcttgaaccc aagaggccag ggttgcagtg agccaagatc    720
gcaccactgc actccagcct gggcaacaga gtcaagactg tctcaaaaaa aaaaaaaaa    780 aactcgta                                                            788

<210> SEQ ID NO 28
<211> LENGTH: 838
<212> TYPE: DNA
<213> ORGANISM: Homo sapiens
```

```
<400> SEQUENCE: 28
ggcacgagaa acacaatact gtttctgcgt cataacaaag atctagttgc gcaaactgca        60
cagccagacc aacccaatta tggttttcct ctgggatctc ttacgctgtg aaagccttct       120
tggtttggac cctgcaactt gcagcagagt tctaaacaaa aattacacgc tgcttgtttc       180
catggctccc ctcaccaatg aaatccggcc tgtcagcagc tgcacccctc agcatattgg       240
accagctatc ccagaagtca gctctgtctg gtttaaactg tacatttatc atgtcactgg       300
acaaggacca ccatcccttt tattgtccaa aggtacaaga cttcgaaaac tgccagatat       360
atttcagagt tatgatcgat tgctaataac atcttggggt catgatcctg gagtagttcc       420
tacctcaaat gtgctcacga tgttgaatga tgctttaaca cattctgcag ttttaattca       480
ggggcatggt ctgcatggga taggagaaac tgtccatgtc ccatttccat ttgatgaaac       540
agaactacaa ggagagttca ctcgtgtcaa tatgggtgtt cataaagcat tgcagatact       600
aaggaacaga gtggacttac agcatctctg tggatatgtc accatgttga atgcttccag       660
ccaacttgca gatagaaaac tcagtgatgc ttctgatgag agaggagaac ctgatttggc       720
ttctggctca gatgtaaatg ggagtacaga gtcatttgaa atggtcattg aggaagcaac       780
tatagattca gcaacaaagc aaacctctgg tgccacaaca gaagcagatt gggttcct         838

<210> SEQ ID NO 29
<211> LENGTH: 755
<212> TYPE: DNA
<213> ORGANISM: Homo sapiens
<220> FEATURE:
<221> NAME/KEY: SITE
<222> LOCATION: (640)
<223> OTHER INFORMATION: n equals a,t,g, or c

<400> SEQUENCE: 29
ggcagaggga aatgcatagg cttgtaatga taattaagat tcaatctcac tctcaatgag        60
atcttgggat tcctgcaagt ttgaccttca cttatgcaat ctgtaaaatg aaggcattgg       120
gcttagatga cttagatggt ttcttcagtg tcttacaggc ttacatgtta tatttttgaa       180
ttgctataaa gcatgttttg caaattctga caccaaacaa tgttttgcat tcctatagca       240
cagataaacc atgtttatag tagccttact cattctccat tgggccttag gtggtacagt       300
gatgtccaag tgactcgtga cctctcactt cttccacttt tccaggtaga agatcagcct       360
tgctcagcct cctgggatta ggagatgttt taagaaaagg agaatttgca tcaaagttct       420
gacattgttt gaggaaaaga ggtagatttc ctaaaaattc ccctgaagcc cataggatat       480
attctcttca aaataatgag tgggccgggt gcagtggctc acacctgtta tcccagcact       540
ttggaaggcc atggtgggca gatcacttga ggtcaggagt ttgagaccag cctggccagc       600
atggtgaaac cctgtctcta ctaaaaatac aaaaattagn ccggatgtgg tggtgcatgc       660
ctgaggttgc agacagccga gatggtgcca ctgcactcca gcctgggcaa cagagcgaga       720
ccctgtctca gaaaaaaaaa aaaaaaaaac tcgaa                                  755

<210> SEQ ID NO 30
<211> LENGTH: 813
<212> TYPE: DNA
<213> ORGANISM: Homo sapiens
<220> FEATURE:
<221> NAME/KEY: SITE
<222> LOCATION: (283)
<223> OTHER INFORMATION: n equals a,t,g, or c
<220> FEATURE:
<221> NAME/KEY: SITE
```

<222> LOCATION: (691)
<223> OTHER INFORMATION: n equals a,t,g, or c

<400> SEQUENCE: 30

| | | | | | |
|---|---|---|---|---|---|
| gcaggaattt | ctacctatat | ttccttcctt | actgtgttgt | gtgtgtttgt | atgtgtgtgt | 60 |
| gtttaatttg | tagcatttgc | cagtttctgt | ggtgtaaata | ctcccactac | agctgttttc | 120 |
| aagctaacat | tgtgatacca | caaaaaatgg | aattgggaag | gcacaatcaa | gattaacaag | 180 |
| ccagtttaga | ccaagacaat | ttttctgccc | tattagttgg | gcacaagtta | gaaaggctga | 240 |
| tagtatctca | tgttggaaag | gtgagagaga | aggccctcat | gcnttattaa | tggcatatgc | 300 |
| attgaagtgc | cctgtttgag | ggcatgctgt | tagtaacttt | taaaatatga | gatgtcatac | 360 |
| tttttgactg | aaaatacaac | tcttgtagga | ttctatttta | tagaactact | taggtgcata | 420 |
| aatatacaaa | ataactgtc | attgcagcat | tatttgtaat | agtggaaaca | gaagactttt | 480 |
| cattaataag | agaatggtta | ggccagatcc | agtggctcac | acctgtaatc | ccaacatttt | 540 |
| gggaatccaa | ggcaggagga | tcgctttagc | ctaggagttg | gagaccagca | tgggcaacat | 600 |
| aacaagacct | tgtctctact | aaaaaaaaat | aataataatt | agtctggcat | ggtggcacac | 660 |
| ctgtactccc | agctacttgg | gaggctgggg | ncaaggagga | ttgcttgagc | ccaggagatt | 720 |
| gaggctgcag | tgaactgtga | tcacaccact | gcacaccagc | ctgggtgaca | cagcaaaact | 780 |
| ctgtctcaaa | aaaaaaaaa | aaaaaaactc | gta | | | 813 |

<210> SEQ ID NO 31
<211> LENGTH: 513
<212> TYPE: DNA
<213> ORGANISM: Homo sapiens

<400> SEQUENCE: 31

| | | | | | |
|---|---|---|---|---|---|
| ggcacgagat | tttttaaaaa | atcttaattt | ttttctctgt | tttagggatt | atcttaatta | 60 |
| aaacttagaa | aataatgact | tttggtttag | gccagggcct | ttgttttctt | ttttgctacc | 120 |
| aggtacttgt | tgcctttaga | ctgaccaacc | agatccctgc | actggggtat | atatcccatc | 180 |
| tatcttccca | cataccatac | ttggctctct | ttggatagac | tctgatatta | agtacttgtt | 240 |
| tctcttctac | ttgaaagtat | ctatatttca | tggaggatgg | tgcttcttaa | cgttctggtt | 300 |
| gcagggctct | aggcctgaag | ggcttttttg | gctagtgaag | atgggtttca | tcatgttttt | 360 |
| caagtcacac | tttcttcggt | ggtggtcttg | ttgccatacc | cagctgagct | tatatctaac | 420 |
| cagccctact | ttcagagagt | tggcattcag | gtgtcttcat | ataaagttca | gttatgctgg | 480 |
| agtaacagag | aacaaaaaaa | aaaaaaaaaa | aaa | | | 513 |

<210> SEQ ID NO 32
<211> LENGTH: 576
<212> TYPE: DNA
<213> ORGANISM: Homo sapiens

<400> SEQUENCE: 32

| | | | | | |
|---|---|---|---|---|---|
| ggcacgaggt | ctattaattt | gcttttcttt | agatgtattc | tagagggggg | aaaatcagta | 60 |
| gaagaacagt | tatgtaattc | ttacaagttc | tccatgtgtc | ttgccatctt | gcttttctc | 120 |
| atcctatcag | tactgatga | gaatgtttat | ttcactgaac | tttgccaaag | agtttcaaca | 180 |
| ttttttttgtt | taatcatagg | agaaaaggt | ttatcttatt | tttaaaaatt | tttatttaat | 240 |
| tctttcatta | caaatgaagt | cccagaagtt | gtatttgttt | ctttaggctg | ttcttaattg | 300 |
| ttcatkggaa | caggcagggt | ttgaaggagt | ggggatactg | ggaaagccag | ggtgatgaga | 360 |

| | |
|---|---|
| aaataggaaa gggtcttgt cattgggagg ccactatacc agtggccctt gtaccaggac | 420 |
| taatatggta ctttgaagct ttaaattcat ttctttattc accagataat tattgagtgc | 480 |
| ttactggttc tggacaagta agcattcaat aattttaggc atcccaggat acatcagtga | 540 |
| acaaacaaac ataaaaaaaa aaaaaaaaaa ctcgta | 576 |

<210> SEQ ID NO 33
<211> LENGTH: 1019
<212> TYPE: DNA
<213> ORGANISM: Homo sapiens
<220> FEATURE:
<221> NAME/KEY: SITE
<222> LOCATION: (126)
<223> OTHER INFORMATION: n equals a,t,g, or c
<220> FEATURE:
<221> NAME/KEY: SITE
<222> LOCATION: (202)
<223> OTHER INFORMATION: n equals a,t,g, or c
<220> FEATURE:
<221> NAME/KEY: SITE
<222> LOCATION: (380)
<223> OTHER INFORMATION: n equals a,t,g, or c
<220> FEATURE:
<221> NAME/KEY: SITE
<222> LOCATION: (476)
<223> OTHER INFORMATION: n equals a,t,g, or c
<220> FEATURE:
<221> NAME/KEY: SITE
<222> LOCATION: (511)
<223> OTHER INFORMATION: n equals a,t,g, or c

<400> SEQUENCE: 33

| | |
|---|---|
| gtctcactgt gccacgcagg tgccctgcag ccacggagac gaatgtggac ggccagaagg | 60 |
| tgtaccgaga ctgtagctgt atccctcaga atctttcctc tggttttggc catgccactg | 120 |
| cagggnaaat gcacttcaac ttgtcagaga agccccctcc ttctggtttt catattcgtt | 180 |
| gtgaattttc tttacattcc tncagcagca ttcctgcact aacggcaact ctacgatgtg | 240 |
| tccgtgaccc tcagagatcc tttgccctgg gaatccagtg gattgtagtt agaatactag | 300 |
| ggggcatccc ggggcccatc gccttcggct gggtgatcga caaggcctgt ctgctgtggc | 360 |
| agraccagtg tggccagcan ggctcctgct tggtgtacca gawtcggcca tgagccgcta | 420 |
| cataytcatc atggggctcc tgtacaagtg ctgggcgtcc tcttctttgc catagnctgc | 480 |
| ttcttawama agccctgtc ggagtcttca natggcytgg raamttgtyt gcccagccag | 540 |
| tcctcagccc ctgacagtgc ccacagatag ccagctccag agcagcgtct gaccaccgcc | 600 |
| cgcgcccacc cggccacggc gggcactcag catttcctga tgacagaaca gtgccgttgg | 660 |
| gtgatgcaat cacacgggaa cttctatttg acctgcaacc ttctacttaa cctgtggttt | 720 |
| aaagtcggct gtgacctcct gtccccagag ctgtacggcc ctgcagtggg tgggaggaac | 780 |
| ttgcataaat atatatttat ggacacacag tttgcatcag aacgtgttta tagaatgtgt | 840 |
| tttatacccg atcgtgtgtg gtgtgcgtga ggacaaactc cgcagggct gtgaatccca | 900 |
| ctggagggc ggtggcctgc agcccgagga aggcttgtgt gtcctcagtt aaaactgtgc | 960 |
| atatcgaaat atattttgtt atttaagcct gaaaaaaaaa aaaaaaaaa aaaaaaaa | 1019 |

<210> SEQ ID NO 34
<211> LENGTH: 433
<212> TYPE: DNA
<213> ORGANISM: Homo sapiens
<220> FEATURE:
<221> NAME/KEY: SITE
<222> LOCATION: (309)
<223> OTHER INFORMATION: n equals a,t,g, or c

```
<220> FEATURE:
<221> NAME/KEY: SITE
<222> LOCATION: (408)
<223> OTHER INFORMATION: n equals a,t,g, or c
<220> FEATURE:
<221> NAME/KEY: SITE
<222> LOCATION: (418)
<223> OTHER INFORMATION: n equals a,t,g, or c
<220> FEATURE:
<221> NAME/KEY: SITE
<222> LOCATION: (419)
<223> OTHER INFORMATION: n equals a,t,g, or c

<400> SEQUENCE: 34
ggcacagctc accttcctac cctccactgg aaaccactcc tctccatgtt gacctcctgg      60
attgcctcca tccctcccg ctgtggggtt ctgtgtatct gcttgtgttt tggattggtt     120
cactgtctgg atctgtcaag gaagataacc atttttcag gagctgtgta catggtgaaa     180
aatatacagt tctggttgta aggaactctc acttgggaat attattattt aaaaacttat    240
acgttgagct cagtgctgtc acagaggtaa gaatactgtg gaaaggctat aaatattttt    300
ccccaaagnc aggggttgga aacatttttc tttcctaggc tgttgagact cacagggaaa    360
aaaaaaaaaa aaaatccggg ggggggcccc gtacccattg gcccctangg gggggttnna    420
aaaagggccc gtt                                                       433

<210> SEQ ID NO 35
<211> LENGTH: 642
<212> TYPE: DNA
<213> ORGANISM: Homo sapiens

<400> SEQUENCE: 35
aggaatgcca ggtcgcactc caccttgctg gccggcaagt cctcttaacc tgttggtctg     60
ctttctttgt tacaaagttg gtctggctta tactgctgaa ggtcatggga ttttgctag    120
catattattg aaatgagaca tttgtggcac tggcgttgta ttgtttctgc taataggagc   180
ccgcgtgtct ttcacatatg gttagtctga ttgcttttc tagcctggga ctttgccttg    240
gagagagtcc tagcaaaata ccattcacag ccttcttcca cagggaagga tgactaagag   300
tttagtgctg gaagagcaga agaggaaagc tggaagatca gaaatgaaat tggagctgtt   360
gatgcgtgtg tctctatggt acagtgggca agccctagtc cttcttgggt tgatcactaa   420
cttgtcatgc agtgtcttgg gcaagtcctt tcacctctca ggacctctgt ctgtctccct   480
atagaacggg gaaggtggcc gggcatggta cctcacacca ccagtgcttt gggaggatga   540
ggcaaggga tcactggagg ctaggagttt gagaccagcc tcagcaacag agcaaattcg    600
tctcaattta aaaaaattaa aaaaaaaaa aaaaactcg ta                        642

<210> SEQ ID NO 36
<211> LENGTH: 667
<212> TYPE: DNA
<213> ORGANISM: Homo sapiens
<220> FEATURE:
<221> NAME/KEY: SITE
<222> LOCATION: (656)
<223> OTHER INFORMATION: n equals a,t,g, or c
<220> FEATURE:
<221> NAME/KEY: SITE
<222> LOCATION: (660)
<223> OTHER INFORMATION: n equals a,t,g, or c
<220> FEATURE:
<221> NAME/KEY: SITE
<222> LOCATION: (661)
<223> OTHER INFORMATION: n equals a,t,g, or c
<220> FEATURE:
```

```
<221> NAME/KEY: SITE
<222> LOCATION: (662)
<223> OTHER INFORMATION: n equals a,t,g, or c

<400> SEQUENCE: 36
agagactttg gctgtgagcc ctcacctggg actgatactg gctctttgag cttttagtc      60
atgtgcttgt ctcttctctt acttagcttg tcatgccttg ctgtgccatg gtggcctcat   120
tcagtgactg ctcttcaact ctcaccagaa agtgaccacc attcctgact tccaagatcc   180
ttcttcaagg atatgatgga gagctcgag cttccagct tcttagagta gctcagcatt    240
tccctcaaat ggggtcttcc cttttcccgt agtgaaactc atcagccact gttctgcacc   300
cttgcatggc ctctggagat cttttaacaa gtattgttga gcgtcaccct tctgccaagg   360
atatggatgt aatggtatga gcaaaaacaa aaatactcgc cagtggaggg tatgatccag   420
tgagggagaa agatgtcaat caaatgatta taccaataaa aagtagcaac catgactagt   480
gctatgaaga ggagaaatac aatgcagtga atgagaacct agaatagggt gattctakcc   540
agttagggaa agatggaaga tttttataag gaagtgactc ttgggctgag gtwcacggta   600
aaaaaaaaaa aaaaaaactc gagggggggc ccgtacccaa tcgaccctga tgatgnatgn   660
nncatac                                                              667

<210> SEQ ID NO 37
<211> LENGTH: 654
<212> TYPE: DNA
<213> ORGANISM: Homo sapiens

<400> SEQUENCE: 37
gccaacataa gcacacttaa cctagacttc aatatgcagt agacgcataa ataaacaaat   60
caatgggtga atgcttatta cttttttcct taagcaactc tcctcatatt ttgtttgctt   120
gttcttcatt ktctaggaga atgtggatta tattattcag gagctccgaa gacccaaata   180
cactatatat ttcatttgta agtatgttag ttcttttttt caaacatgta acaacatccc   240
agttagtgtg tttcattgag cccttcatat catcaataac ttcatkgaat ctgtcactat   300
aaaagtctag tttatttaat gtccttccaa agtattaaaa atcttttgac ctgccgggcg   360
cggtggctca cacctgtaat cccagcactt tgggggggcca gggcgggcgg atcatctgag   420
gagtttgaga ccagcctgac caacatggtg aaaccccatc tctactaaaa atacaagatt   480
agctgggcat ggtggcacat gcctgtaatc ccagctactt gggaggctga ggtcaggaga   540
atcgcttgaa ccggagaggc ggagattgca gtgagccgag attcgtcca ttgcactcca   600
gcctgggcaa caaagcgaaa ctccatctca aaaaaaaaa aaaaaaact cgta           654

<210> SEQ ID NO 38
<211> LENGTH: 731
<212> TYPE: DNA
<213> ORGANISM: Homo sapiens

<400> SEQUENCE: 38
ggagagagag agaatgtgga gaaataggaa tgcttttaca ccattggagg gagtgtaaat   60
tagttcgacc attgtggaag acagtatggc aattcctcaa ggatctagaa ccagaaatac   120
catttgaccc agcaatccca ttactgggta tatcccaaa ggattgtaaa tcattctact   180
acaaagacac atgcacacgt gtgtttattg cagcattatt cacaaatagca aagacttggg   240
aaccaaccca aatgtccaac aatgatagac tggattaaga aaatgtggca catatacacc   300
atggaatact atgcagccat aaaaaatgat gagttcacgt ctttggaggg acatggatga   360
```

```
aactgcaaat catccttctc agtaaactat cgcaaggaca aaaaaccaaa caccgcatat      420
tctcactcat aggtgggaat tgaacaatga aacacatgg acacaggaag gggaacatca       480
cactctgggg actgttgtgg agtgagggga gggggagtg atagctttag gatatataac      540
taatgctaaa tgacgagtta atgggtgcag cacaccagca tggcacatgt atacatatgt      600
aactaacctg cacattgtgc acatgtacgc taawayttww wgtwtaataa taataaaata      660
aaataaaata aaaaagaaa agatgtggct ccaggtttct ttgcttctaa aaaaaaaaa        720 aaaaaactcg a                                                          731

<210> SEQ ID NO 39
<211> LENGTH: 378
<212> TYPE: DNA
<213> ORGANISM: Homo sapiens

<400> SEQUENCE: 39
tcgacccacg cgtccgtaag attaaatcag ataatgcaca cggaaatacg ttacaaatgg       60
aagtgttgtt gttcttccaa gtttgcaagg agaggcagcg gcagtgttct tgcagtgtgt      120
ctgagttcca cgtgacttat attggattat tatataaatc ctgtaattga tctgtcatac      180
ttttatgtcc attctttatg tcatatttct ctctcacata tacatacaca gttgtataca      240
tacttaaatc tctatgtatt agcagtctgc acaacatata ccttttaata tttatatttc      300
tgttcagttc tgttcatacc acagaatatg tgttataaac tcttttatta agcttaaaaa      360
aaaaaaaaaa gggcggcc                                                   378

<210> SEQ ID NO 40
<211> LENGTH: 642
<212> TYPE: DNA
<213> ORGANISM: Homo sapiens
<220> FEATURE:
<221> NAME/KEY: SITE
<222> LOCATION: (41)
<223> OTHER INFORMATION: n equals a,t,g, or c
<220> FEATURE:
<221> NAME/KEY: SITE
<222> LOCATION: (49)
<223> OTHER INFORMATION: n equals a,t,g, or c
<220> FEATURE:
<221> NAME/KEY: SITE
<222> LOCATION: (64)
<223> OTHER INFORMATION: n equals a,t,g, or c
<220> FEATURE:
<221> NAME/KEY: SITE
<222> LOCATION: (607)
<223> OTHER INFORMATION: n equals a,t,g, or c
<220> FEATURE:
<221> NAME/KEY: SITE
<222> LOCATION: (621)
<223> OTHER INFORMATION: n equals a,t,g, or c

<400> SEQUENCE: 40
taaaggggaa acaaaaaggc tgggaaggct tccaaccgcg ntttgcggnc cggcttctag       60
gaantagtgg aatcccccgg gctggcagga attcggcacg agaaaatgac ttcagacaaa     120
tatgatcaat ctctacagtc ccctgatgaa tttcacaggt tcccaccacc atcagttcta     180
cctattcatc tcatccatgc tcattgttct gcctctttcc tgttcctatg gatgccctgg     240
catgtttgtt tctttctttc tggcctccta tttccctccc ctcagacatc acttcagcat     300
ctgtgccttc tcacttccct tatcctgggt gttaccattt cagcctatga gcatgccatt     360
aatttgccat ctttacaaaa ttctctcttg acttcacatc cctctgtagc tgccctctcc      420
```

-continued

```
cttctctcct cttctttaca acaaaactcc ttaaaagaac tgttggctgg gcacagtggt      480
tcactcctat aatcccagca ctttcagaag ccaaggtggg aacatcactt gaggccaaga      540
ggtcgagacc agcccaggca acacagtgag acctcatcac tacaaaaaaa aaaaaaaaaa      600
actcganggg ggggccggta nccaattggc ctaaagtgag tc                         642
```

<210> SEQ ID NO 41
<211> LENGTH: 442
<212> TYPE: DNA
<213> ORGANISM: Homo sapiens

<400> SEQUENCE: 41

```
ggcacgagat agaacccact gcctcctgat gaagtcccta ctgttcaccc ttgcagtttt       60
tatgctcctg gcccaattgg tctcaggtaa ttggtatgtg aaaaagtgtc taaacgacgt      120
tggaatttgc aagaagaagt gcaaacctga agagatgcat gtaaagaatg gttgggcaat      180
gtgcggcaaa caagggact gctgtgttcc agctgacaga cgtgctaatt atcctgtttt       240
ctgtgtccag acaaagacta caagaatttc aacagtaaca gcaacaacag caacaacaac      300
tttgatgatg actactgctt cgatgtcttc gatggctcct accccgtttt ctcccactgg      360
ttgaacattc cagcctctgt ctcctgctct aggatccccg actcattaaa gcaaagaggc      420
ttaaaaaaaa aaaaaaaaaa aa                                               442
```

<210> SEQ ID NO 42
<211> LENGTH: 1734
<212> TYPE: DNA
<213> ORGANISM: Homo sapiens
<220> FEATURE:
<221> NAME/KEY: SITE
<222> LOCATION: (1714)
<223> OTHER INFORMATION: n equals a,t,g, or c
<220> FEATURE:
<221> NAME/KEY: SITE
<222> LOCATION: (1719)
<223> OTHER INFORMATION: n equals a,t,g, or c
<220> FEATURE:
<221> NAME/KEY: SITE
<222> LOCATION: (1723)
<223> OTHER INFORMATION: n equals a,t,g, or c

<400> SEQUENCE: 42

```
gcgggagttc ctccttgctc tcgcccctac tctttctggt gttagatcga gcwaccctct       60
aaaagcagtt tagagtggta aaaaaaaaaa aaaacacacc aaacgctcgc agccacaaaa      120
gggatgaaat ttcttctgga catcctcctg cttctcccgt tactgatcgt ctgctcccta      180
gagtccttcg tgaagctttt tattcctaag aggagaaaat cagtcaccgg cgaaatcgtg      240
ctgattacag gagctgggca tggaattggg agactgactg cctatgaatt tgctaaactt      300
aaaagcaagc tggttctctg ggatataaat aagcatggac tggaggaaac agctgccaaa      360
tgcaagggac tgggtgccaa ggttcatacc tttgtggtag actgcagcaa ccgagaagat      420
atttacagct ctgcaaagaa ggtgaaggca gaaattggag atgttagtat tttagtaaat      480
aatgctggtg tagtctatac atcagatttg tttgctacac aagatcctca gattgaaaag      540
acttttgaag ttaatgtact tgcacatttc tggactacaa aggcatttct tcctgcaatg      600
acgaagaata accatggcca tattgtcact gtggcttcgg cagctggaca tgtctcggtc      660 ccctcttac tggcttactg ttcaagcaag tttgctgctg ttggatttca taaaactttg      720
acagatgaac tggctgcctt acaaataact ggagtcaaaa caacatgtct gtgtcctaat      780
ttcgtaaaca ctggcttcat caaaaatcca agtacaagtt tgggacccac tctggaacct      840
```

```
gaggaagtgg taaacaggct gatgcatggg attctgactg agcagaagat gattttatt      900 ccatcttcta tagcttttt aacaacattg gaaaggatcc ttcctgagcg tttcctggca      960
gttttaaaac gaaaaatcag tgttaagttt gatgcagtta ttggatataa aatgaaagcg     1020
caataagcac ctagttttct gaaaactgat ttaccaggtt taggttgatg tcatctaata    1080
gtgccagaat tttaatgttt gaacttctgt tttttctaat tatccccatt tcttcaatat    1140 cattttgag ctttggcag tcttcattta ctaccacttg ttctttagcc aaaagctgat      1200
tacatatgat ataaacagag aaatacctt agaggtgact ttaaggaaaa tgaagaaaaa    1260
gaaccaaaat gactttatta aaataatttc caagattatt tgtggctcac ctgaaggctt    1320
tgcaaaattt gtaccataac cgtttattta acatatattt ttattttga ttgcacttaa     1380 attttgtata atttgtgttt cttttctgt tctacataaa atcagaaact tcaagctctc     1440
taaataaaat gaaggactat atctagtggt atttcacaat gaatatcatg aactctcaat    1500
gggtaggttt catcctaccc attgccactc tgtttcctga gatatacctc acattccaat    1560
gccaaacatt tctgcacagg gaagctagag gtggatacac gtgttgcaag tataaaagca    1620
tcactgggat ttaaggagaa ttgagagaat gtacccacaa atggcagcaa taataaatgg    1680
atcacactta aaaaaaaaaa aaggggggc cgcnctggng ggnccaagct ttcg           1734

<210> SEQ ID NO 43
<211> LENGTH: 517
<212> TYPE: DNA
<213> ORGANISM: Homo sapiens

<400> SEQUENCE: 43
gcacgagtag aagcatgttc ttcacttcaa gacccaggac cccatggaca tcctgcctac      60
agatcgcccc actagccctg cttcagtcac tgggcatctg gcagcactcg ataggtgcca    120
tgtggtactg cctgctctgt gggtgcagct gccatgccaa ggccgtcccc tctgtcctct    180
ccaggctctc ctgtaacctc ccagctctgc tctcccatgc cctccctcaa cccagcctt    240 ccgtggggc tcctcctggc tctccccggc ctgtccctcc acccccctt tcagaccctc    300 acagctgcct ccccacacca gcttcaggg gactctgcag cccacctctc tgccactcc    360 ttcctcctag attctcactg aagcttcccc cgctctccct agacccgcag ctcataccc    420 cggctactta ttagaatgcc tggcaagctt ggataaaacc ccatactcag ccacacccag    480
gcccattaaa ccagacacct agagttggcc tggaagc                             517

<210> SEQ ID NO 44
<211> LENGTH: 486
<212> TYPE: DNA
<213> ORGANISM: Homo sapiens

<400> SEQUENCE: 44
gcacgagagg aaatataaat gtgcatgttc tctacatgtg gcttaagtaa ttacttaata      60
attaccacat tcttgctcct cagtatctct tcccttgttc ccctacacc tagcaaatta    120 tttgactcat ccagtcattg gaaatactga gttcgaatca aaatgctgga gtgagaagga    180
atgttacacg tagtgcagcc ctccatgta gacatgaaaa aactgaggtc cagaatttgt    240
gccttatcca aagtcacagg tttatgtggt gatactcttc ctctcctaga gcctttaatt    300
ataattatta ctattattat catcaacagt ttagcttttc tctgccatct gagaagatga    360
actaacgaat ggctaaagtt agaagtttag aatggaaata aggtctgact cttgaaatcc    420
```

| | |
|---|---|
| ttccagcatc tttttctttta gcaactctgt tccacaggca gtgggagaaa aaaaaaaaaa | 480 |
| aaaaaa | 486 |

<210> SEQ ID NO 45
<211> LENGTH: 826
<212> TYPE: DNA
<213> ORGANISM: Homo sapiens

<400> SEQUENCE: 45

| | |
|---|---|
| ggcacagctg gatttagtga cttgctttta gtgaatgtaa tgtgtcagac aagacggagt | 60 |
| attactttca agaataagtt acaaaaggag tcacgcattt atcctatgca tctcctgttg | 120 |
| ctttcttgct tgctggctgg caaagcaagc tgtcatgttg tgagaagccc tgtggataat | 180 |
| cccttgtggc aaggaggtaa tgcctatggc aacagccag taaggactgg gccttgccaa | 240 |
| caaccacata agtgagcttg aaagtgaatt gtccccattc aagccttgag atgactgcag | 300 |
| cccgggccag caacttgatt gcagcgtttt gagagaccct acaccagaca cacctggcta | 360 |
| atttctactt agacttttta ctccacaaaa actaagagat aataaatctg ttactttaaa | 420 |
| ctgctgagta ttgtttactt tgccgtacgt aagcagtata gacagacttt tacataaatc | 480 |
| ctgattccaa tgcttatcca ttgtgcatta tgattaagtt atagcacaat ctcagtttcc | 540 |
| tcatctctat aaaaagtgaa aggaggcaga ggccagcaga tcacttgagg tcaggggtgc | 600 |
| aagaccagcc tggccaacat ggtgaaaccc cgtctctact aaaaatacaa aaattagcca | 660 |
| ggcgtggtgg ctcatgcccg taatcccagc tactggggag gctgaggcag gggaattgct | 720 |
| tgaatccagg aggcggaggt tgcagtgagc tgagatcatk ccactgtact tcagcctggc | 780 |
| cgacagagtg agactccatc tcaaaaaaaa aaaaaaaaaa ctcgag | 826 |

<210> SEQ ID NO 46
<211> LENGTH: 694
<212> TYPE: DNA
<213> ORGANISM: Homo sapiens

<400> SEQUENCE: 46

| | |
|---|---|
| gcttagattt tttaagtcct ctcaaatttg tacactcaga actaagtata ttcaaatgta | 60 |
| gtctgatttg catagagaat gacattttct tcattcagac tttgttttta atgaaacctg | 120 |
| ataccagtga ttttggcagc tgtaacaggc tgtatgtctc tttgaaatag acttttttaa | 180 |
| aagcctagtt gtttctcact gtcctgtgcc attttgttgt tattgttgat ttttttgttc | 240 |
| taagcttatg actttatatt tatccttatt aaatatgatc cccttaaatt tagcctcctg | 300 |
| ttccagccac ttagaattac ttaaaaagtt gattatgtca tacagggtat ttacttttcc | 360 |
| catcccagat acctgtcatt tgcacatttg atcgtcctcc tttccatatt ctcatccaag | 420 |
| tcatttataa aaaatgttta caaaggacag gttgctctgg gcccctgttg catactactg | 480 |
| agccttcttc cagatttatc tgcactcttt aggtacagtt gtatagttgt ctgtgaagcc | 540 |
| acttaacttt taagttaaaa aattcatatt ttttcacctt gcacagtgat atcaagagag | 600 |
| actttatttt atgccttgct gaaatccaga tactatattt atgcctctag catttgctgg | 660 |
| cctaaccata taaaaaaaaa aaaaagggc ggcc | 694 |

<210> SEQ ID NO 47
<211> LENGTH: 856
<212> TYPE: DNA
<213> ORGANISM: Homo sapiens

<400> SEQUENCE: 47

```
gaattattga aaataactga aagaaagcct agtggattgt tactaatgat ttaatgtatt      60
ttcttttaac ctgtaggttc tctcttcatc tcttgccttg ccctctttt ctttgttttc     120 ttcctccttg cagtttattt gttgaagaaa ccagttatct ctgttttgtt tcccatggta     180
tgaattttgc tgagtgcatc tttacatgta gtttaatgtg ttgtttggtc cttcacattt     240
cctgtaaatt gacagttgaa tctacaagct tgatcacatt cacattttt ttagggtggt     300 ggggctggcg gtacacacag ttatttccat ttcatgatgt tagcagtcgt tgataatcat     360
gctgcgatct attcattata tgttacaaaa tggtgatata attttatcat ttattaactg     420
ttcctttaaa agtttatatc atatatctct gtgtgtatat ataagatta atgtgcagga     480 gttttgcttt cagtgaatgt ttgcattcca atcattgctt agaaagtttt tttgcccttg     540
ccgggcgcgg tggctcacgc ctgtaatccc agcactttgg gaggccgagg cgggcggatc     600
acgaggtcag gagatcgaga ccatcccggc taaaacggtg aaaccccgtc tctactaaaa     660
atacaaaaaa ttagccgggc gtagtggcgg gcgcctgtag tcccagctac ttgggaggct     720
gaggcaggag aatggcgtga acccgggagg cggagcttgc agtgagccga ggtcccgcca     780
ctgcactcca gcctgggcga cagagtcgag atccgtctca aaaaaaaaa aaaaaaaaa     840 aaaaatgacc ctcgta                                                   856

<210> SEQ ID NO 48
<211> LENGTH: 1643
<212> TYPE: DNA
<213> ORGANISM: Homo sapiens

<400> SEQUENCE: 48
gaattcggca cgaggaaact gttagccctt aatatgcatc acatttgtgg ttccatagtg      60
cttctccttt gcttgtttga tctctgcatg gcagcagtgg ggcagctcca catttggagc     120
ccatactcca aaatgcagag cactcttctc acagcacaca ttcccagccc caaacaaaac     180
ctgaattttc aactctgccc attaaagtga atgtatccct gtaatttagt atgtacttat     240
tatggaaaat gtaacaaaag cagagaagtg tgatttcatt ctgtatcaca aattgaagca     300
aatcaacagc aaatacagca ggattcaggg aggcttagtt tacaacgtac tttgtacctc     360
ctgccattta aattattttg ccactctggg cttctgaaaa cacaagggga gatacagccc     420
tccaactatg agccttgcag agagagacaa aagggccaga ggtcctggga tggaatacta     480
gagcccccac cttctcatgc tttggaaacc tgccagagcr cttaccctgc tggaagatta     540
atgaagactc cattctgtgt ttcataacag tagcgttgtt ttctccatca aaaacagagg     600
gtcacagaaa tgtgctgaaa agatgtggtc cagcaaggtt ctgtagtccc acctcagtgc     660
ctgtgggctg tgttttttcac tgtaacaagc actttggtaa actagaaaga agaaaggatt     720
ctcaggatgt gttcaaagct aagagagttt tcattttaaa aagaaacata catactcact     780
ccatggcttt cctcatcctc ctctcttttt tcttcttggt gggaagctgg atgcggggca     840
tgcatcattc tgtatggaca aatgtgttat gtccacccat actcttgtga caactcccca     900
gcactgtcct gcaataccat gctggccttg gtagtaaaac tccttggtat ctgtgagagt     960 cctcttttc tatgccctag actacttta accactttc tctggaatga ctcccacatt    1020
tgattgggta ttgaaagggt aacagcaaaa tgatgattgt ggagatggat ctattaggtc    1080
tcatgttggt cccctggttg aaactatwtt caaaaaagcc ccaacaatgg gcctgtcmcc    1140
ttgctagtca tccattctta atgcctattt atcagccctc tgaggtcata taaaagttgc    1200
```

```
cacctttga  accaagtatt  tgtatttact  atgggaaagg  tgtggactac  agattcgtat    1260
tatattattt  taatggattt  taagtaattt  ataagtatgc  tgagtgtaaa  ttttttttaa    1320
aaactgtatt  ataaaaggac  atatcctgtg  aaatataaca  ttttactgtt  taatagaata    1380
attctataag  aagaatgatt  tatctcaccc  acggaactga  ttacattccg  gatgcaatca    1440
ataggcactt  tgtaatttcc  tttttgtttt  tttttctttg  ctgggggggtt  gagggggtaac   1500 aagataccat  ctgtataaag  tgcagtttgt  gtcactcaaa  atatgcactg  tatggctaca    1560
caaaagcagc  ttgatgaaca  aatcacccca  tggctcatta  agaacaaag  cttccagaaa    1620 aaaaaaaaaa  aaaaaaactc  gta                                                1643

<210> SEQ ID NO 49
<211> LENGTH: 709
<212> TYPE: DNA
<213> ORGANISM: Homo sapiens

<400> SEQUENCE: 49
gaagaaaagg  aagcagtaac  tacgaatagt  gcttatacat  gctggggtct  gtttgcaggg    60
cccttcatgt  attaacctgt  ttactgctct  ccagtaaccc  tgtggtgcag  gcaccatgtt   120
ccctcaatga  ggaaagtaaa  tcacaagggg  tgacatgtgc  tgtgctccca  gctggggatt   180
tgaacccagg  tagtctagta  tcagcatgtg  tgcccttaac  cgtaaccctta  taacggttag  240 aagagcttca  gggaccttcg  tcaggacata  catcttgtaa  ataattggtt  tgggagtaaa   300
atgcatgctg  agtcaccagt  gaatcttctg  tgttctcatg  ttactttggg  catatcttca   360
tcaaaacatt  gcagcagtct  cttacaagtt  ttgtttgttt  cctagtcatg  aggactggga   420
ttctgctttt  catgtttgat  tactcagagt  acatagtttg  gcatatttta  ggcacggtaa   480
atattgatcc  aatctgattc  ctagttcagt  ggtttatgc  tgtaacagct  ttttcctcct    540
cctttacgtt  gtcaagccac  tttctcatgg  tttcatcttt  tccttcttgc  tttgtttctg    600
gagcacacat  tttttacttt  tttttgattg  ccttctattt  ggttttcttt  aaggtggtgc    660
atttaaaaag  cagcccctc  ttcttcaaaa  aaaaaaaaaa  agggcggcc                  709

<210> SEQ ID NO 50
<211> LENGTH: 541
<212> TYPE: DNA
<213> ORGANISM: Homo sapiens

<400> SEQUENCE: 50
tgcaggtaac  cgttccggaa  ttcccgggtt  cgacccaagg  ggtcccgtga  tgccttgtca    60
tggtcttctt  gcacagggcc  tcagcctggc  acctctgcca  ccgtgggctc  tctgttgtgt   120
gggggtgtcc  cgtgcattgc  aggacatcca  gcagcatccc  cggcctcctg  ctccgtgcca   180
gtagcgccgc  acccgccgt  cgtgacagcc  caggtctccc  ggtgtgcaga  atgcccgctg    240
gtcatgctga  gaggtacagg  ggtgctgccc  ccagggtttg  aacgctgtct  aactcccacc   300
tctggtgtgt  ctctccctg  tgtgtagcgt  ggagtcactg  gatgagtgtg  gtgacctccc    360
tgtgtccagc  tgccctgggc  tgcaagcagg  tccctcctgc  agccctccag  gccaccctta    420
agcagagctg  gaccagcctg  gccaacatgg  tgaaacccca  tctctactaa  aaatacaaaa    480
attagccaag  cgtggtggaa  ctctgtctca  aaaaaaaaaa  aaaaaaaaa  aaagggcggc    540 c                                                                         541

<210> SEQ ID NO 51
<211> LENGTH: 720
```

```
<212> TYPE: DNA
<213> ORGANISM: Homo sapiens
<220> FEATURE:
<221> NAME/KEY: SITE
<222> LOCATION: (20)
<223> OTHER INFORMATION: n equals a,t,g, or c

<400> SEQUENCE: 51
ccacgcgtcc gctccgcggn cgcctcgggc ggaacctgga gataatgggc agcacctggg      60
ggagccctgg ctgggtgcgg ctcgctcttt gcctgacggg cttagtgctc tcgctctacg     120
cgctgcacgt gaaggcggcg cgcgcccggg accgggatta ccgcgcgctc tgcgacgtgg     180
gcaccgccat cagctgttcg cgcgtcttct cctccaggtt gcctgsggac acgctgggcc     240
tctgtmctga tgctgctgag ctccctggtg tctctcgctg gttctgtcta cctggsctgg     300
atcctgttct tcgtgctcta tgawtttctg cattgtttgt aatcaccacc tatgctatca     360
acgtgacctg atgtggctca gtttccggaa ggtccaagaa cccagggca aggctaagag      420
gcactgagcc ctcaacccaa gccaggctga cctcatctgc tttgctttgg catgtgagcc     480
ttgcctaagg gggcatatct gggtcccta g aaggccctag atgtggggct tctagattac     540
cccctcctcc tgccatacccc gcacatgaca atggaccaaa tgtgccacac gctcgctctt    600
ttttacaccc agtgcctctg actctgtccc catgggctgg tctccaaagc tctttccatt    660
gcccagggag ggaaggttct gagcaataaa gtttcttaga tcaaaaaaaa aaaaaaaaa      720

<210> SEQ ID NO 52
<211> LENGTH: 979
<212> TYPE: DNA
<213> ORGANISM: Homo sapiens

<400> SEQUENCE: 52
ggcacgagta caaagccaaa atgtgatgga acatcccatg atgcagacaa ttcatttac       60
tccagctgta ctccactttc ttttcctgtg gtcttccacg tggagtgtct ctatctgagt    120
cccctgtcca gcccttttta agggtatcct gttgagcagg atttgaaatg tttcacattt    180
tgcttaatcc tccacctcca ccctgatgtc ctgcagtaaa tattcacgca catttcagct    240
tgacacactc taggcaagca gctcaccca gtgtgggcaa cagttctttt tttgcttcac     300
tagctaacca gctggatgac tcatctctgc ctttagattt tccaggtgga tgttggacat    360
ggcacattct gctcaccaaa ctcctgcgta agcatagcaa gacccagagt ttccttgaca    420
ccctctctca catgcacaag gggagaggca gctcctctct gctcctttct gagaggcatg    480
aatcggtgaa acaacagca tagcccatcc cagcaatgtc ctcacaaaat tccaactgcc     540
cattctttac ggtgagtttt ctaaacaggt ttcctccatg acaattttct ctacttgctg    600
tcttaatagg agattttgt ttcccccac ctgtatttt aatggacaca tataccttc       660
tgataaaaat atgtaaaata ttctgttcgt ttttaaaatg tcatattcaa gtctgtggcc    720
atcttttgtt cttaatattc acgtctataa aatgggctag aaaacagcat cattgctcaa    780
ggtgtaaagc tattggttta tctagctgaa aaggtgtgca aggactattg aaaaaagaaa    840
tgttcattca gaaacatggg ctctttttatt ttgtacatat cttacagcat aggatttttt   900
ccctggtgt atatgccaaa gatcagcctc agctgaaaaa aaaaaacaca tatgcccta     960
acttactgct tgcttccaa                                                 979

<210> SEQ ID NO 53
<211> LENGTH: 380
<212> TYPE: DNA
```

```
<213> ORGANISM: Homo sapiens
<220> FEATURE:
<221> NAME/KEY: SITE
<222> LOCATION: (6)
<223> OTHER INFORMATION: n equals a,t,g, or c
<220> FEATURE:
<221> NAME/KEY: SITE
<222> LOCATION: (7)
<223> OTHER INFORMATION: n equals a,t,g, or c
<220> FEATURE:
<221> NAME/KEY: SITE
<222> LOCATION: (11)
<223> OTHER INFORMATION: n equals a,t,g, or c
<220> FEATURE:
<221> NAME/KEY: SITE
<222> LOCATION: (376)
<223> OTHER INFORMATION: n equals a,t,g, or c

<400> SEQUENCE: 53
ggttcnnacc ntagtggttc caaagaattc ggcacgaggt gtatgtgcat actccactca      60
cattgtcttt tattttaaaa tttaaaccag gtagtctgct ttcatgggaa tttttctctc     120
tcctgttttt gccaaaccca ataagttat attaacatat tttctgggaa aaatgggtgt     180
gattcaaagt tagaacattt gttatttac ttcagaaagt ctttattgaa catctttctt     240
gtgtaggacc ctgtgtagaa aatgcaaaga gaaatcatac ttgtcctaca ggaaattata     300
atcttgtcgg gaagataaga tgcagactga tataattcaa ggtaaaaaaa aaaaaaaaaa     360
actcgagagt tcttcnagag                                                 380

<210> SEQ ID NO 54
<211> LENGTH: 2023
<212> TYPE: DNA
<213> ORGANISM: Homo sapiens

<400> SEQUENCE: 54
cccacgcgtc cgcccacgcg tccgaaaaaa aaaaaaaaa aaaaaaattg gcagactcca      60
gagcccacac atttgcactc tagactctac tgccttcctc atgaagaatt ttaggacccc    120
cgtctggctg tgttgttgct tggggttcaa attctggttg aaagatggcg gctgcagtgg    180
gaccactatt atctctgtcc tcacagagtt caagctgaag aagatgtgga aaagtcccaa    240
tggaactatc cggaacatcc tgggggggac tgtcttccgg gagcccatca tctgcaaaaa    300
catcccacgc ctagtccctg gctggaccaa gcccatcacc attggcaggc acgcccatgg    360
csaccagtac aaggccacag actttgtggc agaccgggcc ggcactttca aaatggtctt    420
caccccaaaa gatggcagtg gtgtcaagga gtgggaagtg tacaacttcc ccgcagcggc    480
gtgggcatgg gcatgtacaa caccgacgag tccatctcag gttttgcgca cagctgcttc    540
cagtatgcca tccagaagaa atggccgctg tacatgagca ccaagaacac catactgaaa    600
gcctacgatg ggcgtttcaa ggacatcttc caggagatct ttgacaagca ctataagacc    660
gacttcgaca agaataagat ctggtatgag caccggctca ttgatgacat ggtggctcag    720
gtcctcaagt cttcgggtgg cttttgtgtgg gcctgcaaga actatgacgg agatgtgcag    780
tcagacatcc tggcccaggg cttttggctcc cttggcctga tgacgtccgt cctggtctgc    840
cctgatggga gacgattga ggctgaggcc gctcatggga ccgtcacccg ccactatcgg    900
gagcaccaga agggccggcc caccagcacc aaccccatcg ccagcatctt tgcctggaca    960
cgtggcctgg agcaccgggg gaagctggat gggaaccaag acctcatcag gtttgcccag   1020
atgctggaga aggtgtgcgt ggagacggtg gagagtggag ccatgaccaa ggacctggcg   1080
ggctgcattc acggcctcag caatgtgaag ctgaacgagc acttcctgaa caccacggac   1140
```

-continued

```
ttcctcgaca ccatcaagag caacctggac agagccctgg gcaggcagta gggggaggcg    1200
ccacccatgg ctgcagtgga ggggccaggg ctgagccggc gggtcctcct gagcgcggca    1260
gagggtgagc ctcacagccc ctctctggag gcctttctag gggatgtttt tttataagcc    1320
agatgttttt aaaagcatat gtgtgtttcc cctcatggtg acgtgaggca ggagcagtgc    1380
gttttacctc agccagtcag tatgttttgc atactgtaat ttatattgcc cttgaacac    1440 atggtgccat atttagctac taaaaagctc ttcacaaaat tgtctgctgt gtttgtccct    1500
gaggggagga ggtagtggga ccctgaggca gaggccctgc tagagctggc aggttccct    1560 ggggcagacc agagcacctc aggaaggggc tgccacggca gggaagggac caggcagccc    1620
tgggagcccg cattccacag gggcccactg cggagttctc ggacactcag gcacargcc    1680 tgtgggttcc ctggaatttt ctagcatgat ccagtttctg tgtccagttc tccattctga    1740
gagtcaatca gttcctgata ggttgtcatt gattttttc ttcgttggtt ttaaccttct    1800
aaacatctcc aggccacttt cttagccttt ttctaggtac taaaaagagg tcctacccac    1860
acctgcctca cacttctcct ttccaaggct gcctgagttt ggaggggctt gggtgtgtgt    1920
gaacaagggc cctgcattgt ctaggcctgc agttcccagg cttgggttca ctttcaccat    1980
gcattggcaa aactagaaaa gtaagcttgt gacaaattgt tct                      2023
```

<210> SEQ ID NO 55
<211> LENGTH: 885
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c

<400> SEQUENCE: 55

```
gggtcgnacc cacgcgtccg aatttacttt gctactttaa tgattaattg gcaatgatca     60
atgcacaacc ttttactctc atgtgttatt ttcaattttc cccttgtgtt tattgtagca    120
agaactccct accttccttc cttattatct atttgtaatt tggaagcccc agtataccttt   180 agaattgatc caggatggcc tcatttatgt atggcttgag agttttttt aacgaaaaa     240 acattgattc tctaaaaaat aagagtttat atcatagttt ctcaatattt tcctatctac    300
aaggacaaaa ttttttttca gaagcaaaac aactagcata ctaactttct gtttatgcag    360
tagtaaatat tggttgatta ctgcacaatt tccaggaawt atgcagagat aactacagag    420
atgagtagaa taaaactcat tttagagctt caaactctag tcagagatgt agttacaaac    480
aaataatcca gtgtagttag ttaggtactc tggcagaagt gtaatgaaag tagtatgaaa    540
aaacagagaa agaaatcgaa ggaacacatg gacaaagtga tattaaaaag aatgaggccg    600
ggtgcagtgg ctcacgcctg tgatcccagc actttgggag gacctgaggt caggagttca    660
agtccagctt ggccaacatg gtgaaagctc atctttacta aaaatacaaa aattagccag    720
atgtggtggc aagtgcctgt aaccccagct actcctgagg ctgagggca gcagaattgc    780 ttgaacccag gaggtggagg ttgcagtgag ccgagattgc gccactgcac tccagcctgg    840
ctgacaagag caaacactg tcaaaaaaaa aaaaaaggg cggcc                      885
```

<210> SEQ ID NO 56
<211> LENGTH: 1106
<212> TYPE: DNA
<213> ORGANISM: Homo sapiens

```
<400> SEQUENCE: 56
ggcacgagct gagaggtgtg ccctgacatg gtccagaaa catggttgac ttgatattgc      60
ttctcttcca cagtgcagtt ggctgtaacc tgaaaagtag aggggccctt cagacccttc     120
atgactctat gactttgtcc tctttctatt cctcgaaaac ttctctcatt tgagccattc     180
ctgtcctggt gagagatatg caagttgctg cttctcctct ttgtaccaag tacggtggcc     240
ccatttgggt taaagccatg agccctgcc aagtctgacc atccacgcct acatttaccc     300
caagctcctc ctttgtggcc aagaaccatc actttcttgg accccaccct ttctcttccc     360
ttccagctgc attggtaggt atcttttgga gtctttgctt tgggagtggc tgcacttgcc     420
acagtgtgat gtgggcacta ggggccttgt ggtcctgctg ggcttctttt ctcaccaagg     480
cttccctctt gctccccatc taagggggg ttctgattca cgctcctgcc ttcaacaaaa      540
tgcaggagac tcacagatct ctcttgaaat caaagccata atgtccagac tgccacccttt   600 gccagttttg cttcagtgta atattaggga aaagctagaa cactggtttc agagccacac    660
agaccaggtt gtaatctctg ctgtatttgt tgtatgacct ctgccaagtc atttccctgc    720
ttggtttcct catctgtgaa acatgaaaaa tattatttag ctcataaatg gttttgagtg    780
ctggggttga gtgtgaaatg tttggcctcg gccaggtgca gtggcctgta atcccagcac    840
tttgggaggc cgaggcgggc agatcacctg aggttgggag ttcgagacca gcctgaccaa    900
catggagaaa ccctgtctct actaaaaatg caaaattagt cgggcgtggt ggcacatgcc    960
cataatccca ctactcggga ggctggggca ggacaatcgc ttgaacccag gaggtggagg   1020
ttgcagtgag ccaagatcac gccattgcac tccagcctgg gcaacaagag caaaactcta   1080
tcttaagaaa aaaaaaaaa aaaaaa                                          1106

<210> SEQ ID NO 57
<211> LENGTH: 764
<212> TYPE: DNA
<213> ORGANISM: Homo sapiens

<400> SEQUENCE: 57
ggagctgcag gatcttcaca gttcccccag ccccttcctg atgttcacac atgtcacatg     60
ttctgcccat ctcagatgga tctggagcct ttctggttct gtttaatggc agccctattt    120 atctttatt gcctccttct ctatttttg cacatattca aagatggggt gagtaggtta      180
ccctccactg aatacaaata caaaagcttg agtgtactgg tgttctgcaa gaagcatgac    240
tgttctttct gaactgagct tacttccctg aacaccacgc aggggcatc tgcacctgaa     300 actgcagggc attcttggga tcccacgttt ggattgacag tgccaacctg ggaggccagt    360
cccttttcca tcatcacctt ttccttcttg tcagatatgt cataacccca acaggcccc     420 catgatttga taaattgcta ataatgttca tgccaggtat ttggtgactt aaaagtgttc    480
acgggctggg cgcagtgtct catgcctata atcccagcac tttgagaggc tgagacgggt    540
ggatcatctg aggccaggag tatgagacca gcctggccaa caaggcaaaa ccccatctct    600
actaaaaata caaaaattag ccgggcatgg tggcgggcgc ctgtaattca gctactcggg    660
aggcagaggc ggaggttgca gtgagccgag atagcgycgc tgcactccag cctgggcaac    720
agagagactc tgcctaaaaa aaaaaaaaa aaaaagggc ggcc                        764

<210> SEQ ID NO 58
<211> LENGTH: 738
<212> TYPE: DNA
<213> ORGANISM: Homo sapiens
```

<400> SEQUENCE: 58

```
ggcacgaggt aagaattaca tcttgcagca attagccttt gccacaatgg tgtattacaa      60
acaacttcaa aattcagtga ctgaaaaaaa ttattttgtt tctccagatg tttgagtcag     120
ctgggcaggt tttgcttcac attgcaggtc tgcaggtctg ggtcttcctc acatgtcttt     180
catccttttt ggtcccattg agttattcag ggtacattcc tctcatggtg atggcagagg     240
cacaccaaat ggcaagccca accacgcaag cacttttcaa actgctttt gcatcacatc      300
tgctaacatt ctattagcca aagcaaaaca catagtccac cccaaaatta agaggctgag     360
aaggacattc catctttagt tgcagaaaat gcaaaactac caggcataga atgtagacac     420
aggaaataat aaagagtcag ataaaataat tcaacctctc agaccccata aagatattga     480
ttgaaatgtg tttgaaactg agggaaggat ttggggtttg cagttattct cagtggacca     540
gagaaagaag agatttgaga gttctctgag cagcaggcta tgagacagag cacattaaac     600
agggagggct cttgaaatca atacctgtga aaggagtga aggaagcaa aactgggcaa       660
agggaaaagt tgagctttga tgtggtctca gcaaagggtt caggcaactc catgggaagt    720
gttggaactt gtggccct                                                   738
```

<210> SEQ ID NO 59
<211> LENGTH: 441
<212> TYPE: DNA
<213> ORGANISM: Homo sapiens

<400> SEQUENCE: 59

```
gggggcatgt gatttttagt atggacttaa gagctccatg gcttgggttc aaattccact      60
tctgccgttc actagctgtg tgaccttggg caagtacctt aacctctctg tgccacattt     120
ttctcatttg cacaaggaga ataatagttt actacttcat agggttgtga tgagtctgac     180
aatgagtcat tatgtgtaaa atgttttca cagtgcctga cacagaatgc tatagtagat      240
caacatttgc tgtaactatt actatttgtt attagtgcaa ttgctgtatt ttgtttaatg    300
agaggaagtt taataacact aggattaaaa cattccttct ggtcatgtct tcctgacaag    360
taaaaaagtt gctacttgtt ttccttggct aatcattgaa aaaaaaaaaa caaaaaacaa    420
aaaaaaaaaa aaagggcggc c                                               441
```

<210> SEQ ID NO 60
<211> LENGTH: 784
<212> TYPE: DNA
<213> ORGANISM: Homo sapiens
<220> FEATURE:
<221> NAME/KEY: SITE
<222> LOCATION: (56)
<223> OTHER INFORMATION: n equals a,t,g, or c

<400> SEQUENCE: 60

```
gatttttagt actgctatac tcagttgcct gtctgtagta cccctgtacg tagtantctt      60
ttcttacaac tctgttccca gtaccctat gtttagtccc ttgttctcat gttctcacta     120
ccccaatact taatatactt tgttctcagt atccttgttg ttagtaccct gttctcacta    180
ccccttttct tagtacccct gagggggaa aaaaggatg ataatggggt ataagtctca      240
aaaaacttt ggattgtttg atttgamctg rgtcaaaggt aaaaccagtg ttctggagtt     300
cgacttctgg gtgcaaatcc ctgttgcatc attactggcc ttgtggctga ataggttatt    360
aaactctgta aaatgggcat taaaaycgtg tgtcattcat agtgttgctg tgaatawgtg    420
```

| | |
|---|---|
| agccattcca tattgagggt tcacacagtg tccagcaact ggctaaagtt tgcaaacctt | 480 |
| acccattatt attgtcattg ttagtggtat actttgaggc tgtcacaaat aagcagatat | 540 |
| ttcttcttgt gagagctata taatccctta gtgtagagaa aaatttaatt ttgttacaag | 600 |
| tgatccaagc caggtatggt ggcaagtgcc tgtataccca gctgtacttg ggagggtgaa | 660 |
| gtgggaagat tgcttgagac cagggggttcg aggctgccgt gagccttgtt tgcatcactg | 720 |
| cattccagcc tggatgacat agcaagaccc tgtctcctta aaaaaaaaaa aaaaaaaact | 780 |
| cgta | 784 |

<210> SEQ ID NO 61
<211> LENGTH: 540
<212> TYPE: DNA
<213> ORGANISM: Homo sapiens

<400> SEQUENCE: 61

| | |
|---|---|
| ccacgcgtcc gacctcctac atttatgagc aaagctcggt ttcccttttt ggctttccct | 60 |
| ccgctggttc tctgcttaga acactcacag gcatccttgg gaaccagact ccctgtggtc | 120 |
| acaccatcct cactcccctc ctcctgcaag ggaataggat gtggtttcct ggagcttgga | 180 |
| tagaaagaac aggaagggcg ttttcatatg cccggcatta aggctttgaa gttcttaaaa | 240 |
| cccottctag ggtgaaaccg ttagggaatt tcaacgacgt actagaatta ttgaacaaat | 300 |
| gcaatgggag gatcttgcct tgatcctgaa gcaacaaata cactttaaaa tgacgttta | 360 |
| gagggaaatg ggggaaattg aatatggact gggaactaaa tgattgaaag tagttttgtt | 420 |
| aatcttgttg gtataatatt ttgtagttct gttttttaaac tgctgcagtg tttatggcca | 480 |
| gagtctaaat gtttacgagt tgctttgctt ttaaaatatt ccaacaaaaa aaaaaaaaaa | 540 |

<210> SEQ ID NO 62
<211> LENGTH: 604
<212> TYPE: DNA
<213> ORGANISM: Homo sapiens

<400> SEQUENCE: 62

| | |
|---|---|
| ggtttgggga gtcgggtcga cagkacttgt ttatggattg gatgtggaga gtgacgagga | 60 |
| gaggagagtt aacttcatgt ctgtctggag ccacgtacct gttttttttat ggtgtctcaa | 120 |
| caccccatgc acttgccacc tacttgagaa aactactaga ccttaaaagt gagagttta | 180 |
| aacaaatgaa tgtttgtttt gttttacatt taccgtggga aatttttaaat atatacagaa | 240 |
| atagagtatc atagcaagcc tgcattcatc tgtcacccag ctccaaaaat tataaactca | 300 |
| tagctaatct tgtttcactt ttactcccac ttctttccct ccccactcca ctggatcatt | 360 |
| ttgaagcaaa ttccaaatgt cacgtcgttt cattagcttc tatttctaaa taaggtgtct | 420 |
| cttaaacata accagaatac ccccttttga aaggaaggc tgggtgaggt gactcattcc | 480 |
| tctaatccca gcactttagg aagccaaggt caggatgatc gcttgaggcc aggagttcaa | 540 |
| ggccagactg agcagcatag tgagatccag tcttaaaaaa aaaaaaaaa aaaaagggc | 600 |
| ggcc | 604 |

<210> SEQ ID NO 63
<211> LENGTH: 752
<212> TYPE: DNA
<213> ORGANISM: Homo sapiens

<400> SEQUENCE: 63

| | |
|---|---|
| attgaaggat gatgttaatt ttgtattata gtgttatata tgtaactacc tgtccctaaa | 60 |

```
tataacactg tatgtatcat ttcaacatac ttgccagctc tactgattat gaatattaat      120
cacagataag gaaattgtaa aatatccttt tctcaaaagg cagacacatt tatagccctg      180
tgatcctgac tgacacagta tgaagagctt tcctagtaca tatttcaaaa gttctagctt      240
ccagaatacc aaataccaga ctggtgttat aagtgttctg atttcttatg aaatagagta      300
tgctgctttc tatcatttgt cttgtaagat cactcttcca tcatctgtga gcagraattg      360
tttcatttct gaayccttag tggcctcaca gtgcctggac acataaaggt actcaatgtt      420
tgctgaagga aaaataagtt acagtattag ccaggtgtgg tggctcacac tgtaatccca      480
gcatttggga ggccraggcg gcggatcac gagktcagga gattgagacc atcctggcta      540
atgcggtgaa accccgtctc tactgaagat acaaaaaaat tagcctggcg tggtggcggg      600
tgcctgtagt cccagctact tgggaggctg aagcgggaga atggcatgaa cccaggaggc      660
agagcttgca gtgagtcgag attacgccgc tgcaatccag cctgggcgac agagtgaaga      720
ctctgtctca aaaaaaaaa aaaaaaactc ga                                    752

<210> SEQ ID NO 64
<211> LENGTH: 848
<212> TYPE: DNA
<213> ORGANISM: Homo sapiens
<220> FEATURE:
<221> NAME/KEY: SITE
<222> LOCATION: (388)
<223> OTHER INFORMATION: n equals a,t,g, or c

<400> SEQUENCE: 64
aattcggcag aggaaacaca atactgtttc tgcgtcataa caaagatcta gttgcgcaaa      60
ctgcacagcc agaccaaccc aattatggtt ttcctctgga tctcttacgc tgtgaaagcc      120
ttcttggttt ggaccctgca acttgcagca gagttctaaa caaaaattac acgctgcttg      180
tttccatggc tcccctcacc aatgaaatcc ggcctgtcag cagctgcacc cctcagcata      240
ttggaccagc tatcccagaa gtcagctctg tctggtttaa actgtacatt tatcatgtca      300
ctggacaagg accaccatcc cttttattgt ccaaaggtac aagacttcga aaactgccag      360
atatatttca gagttatgat cgattgcnaa taacatcttg gggtcatgat cctggagtag      420
ttcctacctc aaatgtgctc acgatgttga atgatgcttt aacacattct gcagttttaa      480
ttcaggggca tggtctgcat gggataggag aaactgtcca tgtcccattt ccatttgatg      540
aaacagaact acaaggagag ttcactcgtg tcaatatggg tgttcataaa gcattgcaga      600
tactaaggaa cagagtgrac ttacagcatc tctgtggata tgtcaccatg ttgaatgctt      660
ccagccaact tgcagataga aaactcagtg atgcttctga tgagagagga gaacctgatt      720
tggcttctgg ctcagatgta aatgggagta cagagtcatt tgaaatggtc attgaggaag      780
caactataga ttcagcaaca aagcaaacct ctggtgccac aacagaagca gattgggttc      840
ctctcgta                                                              848

<210> SEQ ID NO 65
<211> LENGTH: 769
<212> TYPE: DNA
<213> ORGANISM: Homo sapiens

<400> SEQUENCE: 65
gcacgagaat ttttgtactg ctatactcag ttgcctgtct gtagtacccc tgtacgtatc      60
ttttcttaca actctgttcc cagtaccct atgtttagtc ccttgttctc atgttctcac      120
```

-continued

```
tacccaata cttaaaactt gttctcagta tccttgttgt tagtaccctg ttctcactcc      180 cctttctta gtacccctga gggggaaaa aagtgataa tgggtataa gtccaaaaac      240 ttttggattg tttgatttga actgagtcaa agtaaaccag tgttctggag ttcgacttcg      300
ggtgcaaatc cctgttgcat catttactgg ccttgtggct gaataggtta ttaaactctg      360
taaaatgggc attaaaacgt gtgtcattca tagtgttgct gtgaatatgt gagccattcc      420
atattgaggg ttcacacagt gtccagcaac tggctaaagt ttgcaaacct tacccattat      480
tattgtcatt gttagtggta tactttgagg ctgtcacaaa taagcagata tttcttcttg      540
tgagagctat ataatccctt agtgtagaga aaaatttaat tttgttacaa gtgatccaag      600
ccaggtatgg tggcaagtgc ctgtataccc agctgtactt gggagggtga agtgggaaga      660
ttgcttgaga ccagggttc gaggctgccg tgagccttgt ttgcatcact gcattccagc      720
ctggatgaca tagcaagacc ctgtctcctt aaaaaaaaaa aaaaaaaaa                  769
```

<210> SEQ ID NO 66
<211> LENGTH: 539
<212> TYPE: DNA
<213> ORGANISM: Homo sapiens

<400> SEQUENCE: 66

```
gacctcctac atttatgagc aaagctcggt ttcccttttt gctttccctc cgctggttct       60
ctgcttagaa cactcacagg catccttggg aaccagactc cctgtggtca caccatcctc      120
actcccctcc tcctgcaagg aataggatgt ggtttcctgg agcttggata gaaagaacag      180
gaagggcgtt tcatatgcc cggcattaag gctttgaagt tcttaaaacc ccttctaggg      240
tgaaaccgtt agggaatttc aacgacgtac tagaattatt gaacaaatgc aatgggagga      300
tcttgccttg atcctgaagc aacaaataca ctttaaaatg acgttttaga gggaaatggg      360
ggaaattgaa tatggactgg gaactaaatg attgaaagta gttttgttaa tcttgttggt      420
ataatatttt gtagttctgt ttttaaactg ctgtcagtgt ttatggccag agtctaaatg      480
tttacgagtt gctttgcttt taaaatattc caacaaaaaa aaaaaaaaag ggcggcgct       539
```

<210> SEQ ID NO 67
<211> LENGTH: 74
<212> TYPE: PRT
<213> ORGANISM: Homo sapiens
<220> FEATURE:
<221> NAME/KEY: SITE
<222> LOCATION: (74)
<223> OTHER INFORMATION: Xaa equals stop translation

<400> SEQUENCE: 67

```
Met Ser Ser Cys Phe Gln Leu Leu Leu Thr Tyr Arg Ala Trp Phe Ser
  1               5                  10                  15

Thr Ser Ser Leu Ala Glu Gln Met Cys Arg Thr Gly Leu Lys Ser Arg
             20                  25                  30

His Ser Pro Thr Ser Glu Gln Thr Glu Arg Cys Ala Arg Ser Trp Cys
         35                  40                  45

Leu Val His His Cys Phe Pro Ser Gln Thr Phe Leu Phe His Ala Cys
     50                  55                  60

Leu Thr Asp Lys Pro Leu Ala Arg Pro Xaa
 65                  70
```

<210> SEQ ID NO 68
<211> LENGTH: 60
<212> TYPE: PRT

```
<213> ORGANISM: Homo sapiens
<220> FEATURE:
<221> NAME/KEY: SITE
<222> LOCATION: (15)
<223> OTHER INFORMATION: Xaa equals any of the naturally occurring
      L-amino acids
<220> FEATURE:
<221> NAME/KEY: SITE
<222> LOCATION: (60)
<223> OTHER INFORMATION: Xaa equals stop translation

<400> SEQUENCE: 68

Met Asn Cys Asp Val Leu Trp Cys Val Leu Leu Val Cys Xaa Ser
 1               5                  10                  15

Leu Phe Ser Ala Val Gly His Gly Leu Trp Ile Trp Arg Tyr Gln Glu
                20                  25                  30

Lys Lys Ser Leu Phe Tyr Val Pro Lys Ser Asp Gly Ser Ser Leu Ser
            35                  40                  45

Pro Val Thr Ala Ala Val Asn Ser Phe Leu Thr Xaa
        50                  55                  60

<210> SEQ ID NO 69
<211> LENGTH: 135
<212> TYPE: PRT
<213> ORGANISM: Homo sapiens
<220> FEATURE:
<221> NAME/KEY: SITE
<222> LOCATION: (135)
<223> OTHER INFORMATION: Xaa equals stop translation

<400> SEQUENCE: 69

Met Ser Tyr Lys Pro Ala Leu Phe Gly Phe Leu Phe Leu Leu Leu
 1               5                  10                  15

Leu Ser Asn Trp Leu Val Lys Tyr Glu His Lys Leu Thr Leu Pro Glu
                20                  25                  30

Pro Gln Gln Glu Glu Lys Pro Lys Thr Ser Glu Asn Asp Ser Lys
            35                  40                  45

Asn Ser Lys Ala Val Asn Thr Lys Glu Val Asn Arg Thr His Ala Cys
        50                  55                  60

Phe Ala Leu Gln Asp Glu Ile Leu Gln Arg Leu Leu Phe Ser Glu Met
65                  70                  75                  80

Lys Met Lys Val Leu Glu Asn Gln Met Phe Ile Ile Trp Asn Lys Met
                85                  90                  95

Asn His His Gly Arg Ser Ser Arg His Arg Asn Phe Pro Met Lys Lys
            100                 105                 110

His Arg Met Arg Arg His Glu Ser Ile Cys Pro Thr Leu Ser Asp Cys
        115                 120                 125

Thr Ser Ser Ser Pro Ser Xaa
        130                 135

<210> SEQ ID NO 70
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation

<400> SEQUENCE: 70

Met Gly Gly Gln Met Met Asn Gln Leu Ile Thr Val Ala Phe Val Arg
 1               5                  10                  15
```

```
Trp Arg Phe Leu Ile Cys Phe Leu Ser Leu Met Lys Ala Ile Leu Lys
            20                  25                  30

Lys Pro Thr Xaa
        35
```

<210> SEQ ID NO 71
<211> LENGTH: 126
<212> TYPE: PRT
<213> ORGANISM: Homo sapiens
<220> FEATURE:
<221> NAME/KEY: SITE
<222> LOCATION: (126)
<223> OTHER INFORMATION: Xaa equals stop translation

<400> SEQUENCE: 71

```
Met Arg Trp Ile Leu Ile Leu Val Ile Ala Leu Trp Phe Ile Glu Leu
 1               5                  10                  15

Leu Asp Val Trp Ser Thr Cys Ser Gln Pro Ile Cys Ala Lys Trp Thr
            20                  25                  30

Arg Thr Glu Ala Glu Gly Ser Lys Lys Ser Leu Ser Ser Glu Gly His
        35                  40                  45

His Met Asp Leu Pro Asp Val Val Ile Thr Ser Leu Pro Gly Ser Gly
    50                  55                  60

Ala Glu Ile Leu Lys Gln Leu Phe Phe Asn Ser Ser Asp Phe Leu Tyr
65                  70                  75                  80

Ile Arg Val Pro Thr Ala Tyr Ile Asp Ile Pro Glu Thr Glu Leu Glu
                85                  90                  95

Ile Asp Ser Phe Val Asp Ala Cys Glu Trp Lys Cys Gln Ile Ser Ala
            100                 105                 110

Val Gly Ile Phe Val Tyr Ser Glu Ala Gly Cys Ser Leu Xaa
        115                 120                 125
```

<210> SEQ ID NO 72
<211> LENGTH: 52
<212> TYPE: PRT
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 72

```
Met Leu Ser Thr Ile Leu Ser Phe Val Cys Asn Cys Ala Cys Arg Leu
 1               5                  10                  15

Asn Arg Ile Leu Ile Val Leu Ile Thr Cys Leu Ile Leu Val Ser Pro
            20                  25                  30

Val Arg Gln Ala Cys Phe Leu Glu Ala Gly Thr Glu Cys His Ser His
        35                  40                  45

Leu Cys Ser Xaa
        50
```

<210> SEQ ID NO 73
<211> LENGTH: 98
<212> TYPE: PRT
<213> ORGANISM: Homo sapiens
<220> FEATURE:
<221> NAME/KEY: SITE
<222> LOCATION: (98)
<223> OTHER INFORMATION: Xaa equals stop translation

<400> SEQUENCE: 73

```
Met Ser Ile Met Leu Leu Thr Phe Thr Leu His Phe Pro Ser Thr Leu
```

-continued

```
                1               5                      10                     15
Leu Ser Tyr Leu Pro Glu Asn Tyr Val Ile Pro Ser Leu Phe Ser Asn
                        20                      25                     30

Leu Gln His Trp Ile Cys Cys Val His Ser Gln Leu Val Thr Cys Phe
            35                      40                      45

Val Phe Gln Arg Asp Asn Val Ser Thr Glu Lys Arg Thr Leu Ala His
        50                      55                      60

Ser Asn Thr Ser Ser Ala Thr Ser His His Leu Ser Pro Cys Thr Thr
65                      70                      75                      80

Gly Asp Gly Leu Pro Ser Ser Trp Gly Gln Thr His Pro Leu Leu
                        85                      90                      95

His Xaa

<210> SEQ ID NO 74
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 74

Met His Leu Leu Leu Ile Asn Phe Leu Pro Ala Val Cys Ile Ile Leu
1               5                       10                      15

Leu Lys Asn Leu Gln Gln Ala Leu Cys Phe Ala Gln Leu Phe Ile Met
            20                      25                      30

Ser Ile Asn Gln Gly Leu Gly Pro Asn Glu Met Ser Xaa
            35                      40                      45

<210> SEQ ID NO 75
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 75

Met Ala Phe Arg Val Leu Tyr Tyr Ser Val Trp Phe Ile Phe Leu His
1               5                       10                      15

Val Ser Phe Ala Thr Pro Lys Val Thr Gly Leu Ile Ala Ser Thr Tyr
            20                      25                      30

His Phe Leu Tyr Val Phe Met Phe Leu Leu Met Ile Leu Ser Ala Xaa
            35                      40                      45

<210> SEQ ID NO 76
<211> LENGTH: 27
<212> TYPE: PRT
<213> ORGANISM: Homo sapiens
<220> FEATURE:
<221> NAME/KEY: SITE
<222> LOCATION: (27)
<223> OTHER INFORMATION: Xaa equals stop translation

<400> SEQUENCE: 76

Met Val Phe Ile Leu Glu Gln Ile Lys Asn Gln Val Phe Phe Leu Phe
1               5                       10                      15

Leu Leu Leu Lys Leu Thr Cys Val Ser His Xaa
            20                      25
```

```
<210> SEQ ID NO 77
<211> LENGTH: 42
<212> TYPE: PRT
<213> ORGANISM: Homo sapiens
<220> FEATURE:
<221> NAME/KEY: SITE
<222> LOCATION: (40)
<223> OTHER INFORMATION: Xaa equals any of the naturally occurring
      L-amino acids
<220> FEATURE:
<221> NAME/KEY: SITE
<222> LOCATION: (42)
<223> OTHER INFORMATION: Xaa equals stop translation

<400> SEQUENCE: 77

Met Gln Leu Ile Gln Leu Ile Thr Leu Thr Ile Thr Gln Val Leu Phe
 1               5                  10                  15

Leu Asp Thr Ile Met Ser Thr Tyr Val Ala Asp Thr Asp Tyr Val Val
            20                  25                  30

Leu Pro Val Ser Ser His Lys Xaa Phe Xaa
        35                  40

<210> SEQ ID NO 78
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation

<400> SEQUENCE: 78

Met Thr Leu Met Thr Ser Ile Tyr Phe Phe Leu Ala Ile Phe Met Ser
 1               5                  10                  15

Thr Arg Ser Glu Arg Leu Xaa
            20

<210> SEQ ID NO 79
<211> LENGTH: 59
<212> TYPE: PRT
<213> ORGANISM: Homo sapiens
<220> FEATURE:
<221> NAME/KEY: SITE
<222> LOCATION: (59)
<223> OTHER INFORMATION: Xaa equals stop translation

<400> SEQUENCE: 79

Met Ser Leu Leu Phe Ile Val Ser Leu Leu Glu Leu Gly Pro Met Ala
 1               5                  10                  15

Leu Leu Ala Glu Arg Lys Ala Met Lys Pro Ser Leu Gly Leu Arg Leu
            20                  25                  30

Glu Glu Glu Glu Glu Glu Thr Pro Phe Glu Glu Gln Arg Ala Val Ser
        35                  40                  45

Val Ile Pro Gly Val Pro Val Thr Tyr Leu Xaa
    50                  55

<210> SEQ ID NO 80
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 80
```

-continued

```
Met Asn Phe Val Ala Ala Leu Ile Phe Ser Pro Asp Gln Tyr Asn Phe
 1               5                  10                  15

Ile Leu Arg Ile Arg Leu Phe Trp Phe Leu Ile Ile Cys Val Leu Ser
                20                  25                  30

Gly Ile Leu Leu Phe Pro Ser Arg Thr Phe Ser Leu His Pro Xaa
            35                  40                  45
```

<210> SEQ ID NO 81
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 81

```
Met Ser Phe Leu Val Phe Ser Phe Phe Cys Phe Gly Phe Ser Asn Ser
 1               5                  10                  15

Arg Phe Ser Arg Asp Tyr Gln His Tyr Leu Ser Leu Leu Ser Ser Pro
                20                  25                  30

His Ala Gln Lys Arg Asn Lys Ile Ile Arg Glu Ser Ser Ile Ser Ala
            35                  40                  45

Leu Leu Thr Ser Xaa
        50
```

<210> SEQ ID NO 82
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 82

```
Met Gln Ile Pro Phe Leu Leu Glu Val Phe Val Ile His Thr Gly Val
 1               5                  10                  15

Leu Gly Ser Lys Leu Leu Lys Ser Gly Gly Leu Phe Asp Leu Thr Ser
                20                  25                  30

Phe Ser Pro Met Ile Ile Cys Phe Ser Asn Lys Ser Xaa
            35                  40                  45
```

<210> SEQ ID NO 83
<211> LENGTH: 61
<212> TYPE: PRT
<213> ORGANISM: Homo sapiens
<220> FEATURE:
<221> NAME/KEY: SITE
<222> LOCATION: (59)
<223> OTHER INFORMATION: Xaa equals any of the naturally occurring
      L-amino acids
<220> FEATURE:
<221> NAME/KEY: SITE
<222> LOCATION: (61)
<223> OTHER INFORMATION: Xaa equals stop translation

<400> SEQUENCE: 83

```
Met Val Ser Phe Ala Cys Phe Cys Phe His Cys Leu Phe Leu Val Ser
 1               5                  10                  15

Tyr Pro Arg Asn His Cys Gln Ile Gln Cys Arg Asp Ala Phe Ser Arg
                20                  25                  30

Ser Phe Leu Leu Gly Val Phe Gln Val Leu Tyr Leu Gly Phe Ile Asn
```

-continued

```
                       35                  40                  45
Tyr Ile Thr Phe Tyr Val Glu Glu Lys Thr Xaa Glu Xaa
            50                  55                  60

<210> SEQ ID NO 84
<211> LENGTH: 253
<212> TYPE: PRT
<213> ORGANISM: Homo sapiens

<400> SEQUENCE: 84

Met Val Phe Leu Trp Asp Leu Leu Arg Cys Glu Ser Leu Leu Gly Leu
 1               5                  10                  15

Asp Pro Ala Thr Cys Ser Arg Val Leu Asn Lys Asn Tyr Thr Leu Leu
            20                  25                  30

Val Ser Met Ala Pro Leu Thr Asn Glu Ile Arg Pro Val Ser Ser Cys
        35                  40                  45

Thr Pro Gln His Ile Gly Pro Ala Ile Pro Glu Val Ser Ser Val Trp
    50                  55                  60

Phe Lys Leu Tyr Ile Tyr His Val Thr Gly Gln Gly Pro Pro Ser Leu
65                  70                  75                  80

Leu Leu Ser Lys Gly Thr Arg Leu Arg Lys Leu Pro Asp Ile Phe Gln
                85                  90                  95

Ser Tyr Asp Arg Leu Leu Ile Thr Ser Trp Gly His Asp Pro Gly Val
            100                 105                 110

Val Pro Thr Ser Asn Val Leu Thr Met Leu Asn Asp Ala Leu Thr His
        115                 120                 125

Ser Ala Val Leu Ile Gln Gly His Gly Leu His Gly Ile Gly Glu Thr
    130                 135                 140

Val His Val Pro Phe Pro Phe Asp Glu Thr Glu Leu Gln Gly Glu Phe
145                 150                 155                 160

Thr Arg Val Asn Met Gly Val His Lys Ala Leu Gln Ile Leu Arg Asn
                165                 170                 175

Arg Val Asp Leu Gln His Leu Cys Gly Tyr Val Thr Met Leu Asn Ala
            180                 185                 190

Ser Ser Gln Leu Ala Asp Arg Lys Leu Ser Asp Ala Ser Asp Glu Arg
        195                 200                 205

Gly Glu Pro Asp Leu Ala Ser Gly Ser Asp Val Asn Gly Ser Thr Glu
    210                 215                 220

Ser Phe Glu Met Val Ile Glu Glu Ala Thr Ile Asp Ser Ala Thr Lys
225                 230                 235                 240

Gln Thr Ser Gly Ala Thr Thr Glu Ala Asp Trp Val Pro
                245                 250

<210> SEQ ID NO 85
<211> LENGTH: 21
<212> TYPE: PRT
<213> ORGANISM: Homo sapiens
<220> FEATURE:
<221> NAME/KEY: SITE
<222> LOCATION: (21)
<223> OTHER INFORMATION: Xaa equals stop translation

<400> SEQUENCE: 85

Met Phe Ile Val Ala Leu Leu Ile Leu His Trp Ala Leu Gly Gly Thr
 1               5                  10                  15

Val Met Ser Lys Xaa
            20
```

```
<210> SEQ ID NO 86
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

<400> SEQUENCE: 86

Met Cys Val Cys Leu Ile Cys Ser Ile Cys Gln Phe Leu Trp Cys Lys
  1               5                  10                  15

Tyr Ser His Tyr Ser Cys Phe Gln Ala Asn Ile Val Ile Pro Gln Lys
             20                  25                  30

Met Glu Leu Gly Arg His Asn Gln Asp Xaa
         35                  40

<210> SEQ ID NO 87
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 87

Met Thr Phe Gly Leu Gly Gln Gly Leu Cys Phe Leu Phe Cys Tyr Gln
  1               5                  10                  15

Val Leu Val Ala Phe Arg Leu Thr Asn Gln Ile Pro Ala Leu Gly Tyr
             20                  25                  30

Ile Ser His Leu Ser Ser His Ile Pro Tyr Leu Ala Leu Phe Gly Xaa
         35                  40                  45

<210> SEQ ID NO 88
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 88

Met Cys Leu Ala Ile Leu Leu Phe Leu Ile Leu Ser Val Leu Asp Glu
  1               5                  10                  15

Asn Val Tyr Phe Thr Glu Leu Cys Gln Arg Val Ser Thr Phe Phe Cys
             20                  25                  30

Leu Ile Ile Gly Glu Lys Gly Leu Ser Tyr Phe Xaa
         35                  40

<210> SEQ ID NO 89
<211> LENGTH: 60
<212> TYPE: PRT
<213> ORGANISM: Homo sapiens
<220> FEATURE:
<221> NAME/KEY: SITE
<222> LOCATION: (54)
<223> OTHER INFORMATION: Xaa equals any of the naturally occurring
      L-amino acids
<220> FEATURE:
<221> NAME/KEY: SITE
<222> LOCATION: (60)
<223> OTHER INFORMATION: Xaa equals stop translation

<400> SEQUENCE: 89
```

```
Met Trp Thr Ala Arg Arg Cys Thr Glu Thr Val Ala Val Ser Leu Arg
 1               5                  10                  15

Ile Phe Pro Leu Val Leu Ala Met Pro Leu Gln Gly Lys Cys Thr Ser
                20                  25                  30

Thr Cys Gln Arg Lys Pro Leu Leu Val Phe Ile Phe Val Val Asn
        35                  40                  45

Phe Leu Tyr Ile Pro Xaa Ala Ala Phe Leu His Xaa
        50                  55              60
```

<210> SEQ ID NO 90
<211> LENGTH: 52
<212> TYPE: PRT
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 90

```
Met Leu Thr Ser Trp Ile Ala Ser Ile Pro Ser Arg Cys Gly Val Leu
 1               5                  10                  15

Cys Ile Cys Leu Cys Phe Gly Leu Val His Cys Leu Asp Leu Ser Arg
                20                  25                  30

Lys Ile Thr Ile Phe Ser Gly Ala Val Tyr Met Val Lys Asn Ile Gln
        35                  40                  45

Phe Trp Leu Xaa
        50
```

<210> SEQ ID NO 91
<211> LENGTH: 32
<212> TYPE: PRT
<213> ORGANISM: Homo sapiens
<220> FEATURE:
<221> NAME/KEY: SITE
<222> LOCATION: (32)
<223> OTHER INFORMATION: Xaa equals stop translation

<400> SEQUENCE: 91

```
Met Val Ser Leu Ile Ala Phe Ser Ser Leu Gly Leu Cys Leu Gly Glu
 1               5                  10                  15

Ser Pro Ser Lys Ile Pro Phe Thr Ala Phe Phe His Arg Glu Gly Xaa
                20                  25                  30
```

<210> SEQ ID NO 92
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation

<400> SEQUENCE: 92

```
Met Cys Leu Ser Leu Leu Leu Ser Leu Ser Cys Leu Ala Val Pro
 1               5                  10                  15

Trp Trp Pro His Ser Val Thr Ala Leu Gln Leu Ser Pro Glu Ser Asp
                20                  25                  30

His His Ser Xaa
        35
```

<210> SEQ ID NO 93
<211> LENGTH: 49

```
<212> TYPE: PRT
<213> ORGANISM: Homo sapiens

<400> SEQUENCE: 93

Met Ser Phe Gln Ser Ile Lys Asn Leu Leu Thr Cys Arg Ala Arg Trp
 1               5                  10                  15

Leu Thr Pro Val Ile Pro Ala Leu Trp Gly Ala Arg Ala Gly Gly Ser
                20                  25                  30

Ser Glu Glu Phe Glu Thr Ser Leu Thr Asn Met Val Lys Pro His Leu
            35                  40                  45

Tyr

<210> SEQ ID NO 94
<211> LENGTH: 25
<212> TYPE: PRT
<213> ORGANISM: Homo sapiens
<220> FEATURE:
<221> NAME/KEY: SITE
<222> LOCATION: (25)
<223> OTHER INFORMATION: Xaa equals stop translation

<400> SEQUENCE: 94

Met His Thr Cys Val Tyr Cys Ser Ile Ile His Asn Ser Lys Asp Leu
 1               5                  10                  15

Gly Thr Asn Pro Asn Val Gln Gln Xaa
                20                  25

<210> SEQ ID NO 95
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 95

Met Ser Tyr Phe Ser Leu Thr Tyr Thr Tyr Thr Val Val Tyr Ile Leu
 1               5                  10                  15

Lys Ser Leu Cys Ile Ser Ser Leu His Asn Ile Tyr Leu Leu Ile Phe
                20                  25                  30

Ile Phe Leu Phe Ser Ser Val His Thr Thr Glu Tyr Val Leu Xaa
            35                  40                  45

<210> SEQ ID NO 96
<211> LENGTH: 87
<212> TYPE: PRT
<213> ORGANISM: Homo sapiens
<220> FEATURE:
<221> NAME/KEY: SITE
<222> LOCATION: (87)
<223> OTHER INFORMATION: Xaa equals stop translation

<400> SEQUENCE: 96

Met Pro Trp His Val Cys Phe Phe Leu Ser Gly Leu Leu Phe Pro Ser
 1               5                  10                  15

Pro Gln Thr Ser Leu Gln His Leu Cys Leu Leu Thr Ser Leu Ile Leu
                20                  25                  30

Gly Val Thr Ile Ser Ala Tyr Glu His Ala Ile Asn Leu Pro Ser Leu
            35                  40                  45

Gln Asn Ser Leu Leu Thr Ser His Pro Ser Val Ala Ala Leu Ser Leu
        50                  55                  60
```

-continued

```
Leu Ser Ser Ser Leu Gln Gln Asn Ser Leu Lys Glu Leu Leu Ala Gly
 65                  70                  75                  80

His Ser Gly Ser Leu Leu Xaa
                 85
```

<210> SEQ ID NO 97
<211> LENGTH: 112
<212> TYPE: PRT
<213> ORGANISM: Homo sapiens
<220> FEATURE:
<221> NAME/KEY: SITE
<222> LOCATION: (112)
<223> OTHER INFORMATION: Xaa equals stop translation

<400> SEQUENCE: 97

```
Met Lys Ser Leu Leu Phe Thr Leu Ala Val Phe Met Leu Leu Ala Gln
 1               5                  10                  15

Leu Val Ser Gly Asn Trp Tyr Val Lys Lys Cys Leu Asn Asp Val Gly
                 20                  25                  30

Ile Cys Lys Lys Lys Cys Lys Pro Glu Glu Met His Val Lys Asn Gly
             35                  40                  45

Trp Ala Met Cys Gly Lys Gln Arg Asp Cys Cys Val Pro Ala Asp Arg
         50                  55                  60

Arg Ala Asn Tyr Pro Val Phe Cys Val Gln Thr Lys Thr Thr Arg Ile
 65                  70                  75                  80

Ser Thr Val Thr Ala Thr Thr Ala Thr Thr Leu Met Met Thr Thr
                     85                  90                  95

Ala Ser Met Ser Ser Met Ala Pro Thr Pro Val Ser Pro Thr Gly Xaa
                100                 105                 110
```

<210> SEQ ID NO 98
<211> LENGTH: 301
<212> TYPE: PRT
<213> ORGANISM: Homo sapiens
<220> FEATURE:
<221> NAME/KEY: SITE
<222> LOCATION: (301)
<223> OTHER INFORMATION: Xaa equals stop translation

<400> SEQUENCE: 98

```
Met Lys Phe Leu Leu Asp Ile Leu Leu Leu Pro Leu Leu Ile Val
 1               5                  10                  15

Cys Ser Leu Glu Ser Phe Val Lys Leu Phe Ile Pro Lys Arg Arg Lys
                 20                  25                  30

Ser Val Thr Gly Glu Ile Val Leu Ile Thr Gly Ala Gly His Gly Ile
             35                  40                  45

Gly Arg Leu Thr Ala Tyr Glu Phe Ala Lys Leu Lys Ser Lys Leu Val
         50                  55                  60

Leu Trp Asp Ile Asn Lys His Gly Leu Glu Glu Thr Ala Ala Lys Cys
 65                  70                  75                  80

Lys Gly Leu Gly Ala Lys Val His Thr Phe Val Val Asp Cys Ser Asn
                     85                  90                  95

Arg Glu Asp Ile Tyr Ser Ser Ala Lys Val Lys Ala Glu Ile Gly
                100                 105                 110

Asp Val Ser Ile Leu Val Asn Asn Ala Gly Val Val Tyr Thr Ser Asp
            115                 120                 125

Leu Phe Ala Thr Gln Asp Pro Gln Ile Glu Lys Thr Phe Glu Val Asn
        130                 135                 140

Val Leu Ala His Phe Trp Thr Thr Lys Ala Phe Leu Pro Ala Met Thr
```

```
                145                 150                 155                 160
Lys Asn Asn His Gly His Ile Val Thr Val Ala Ser Ala Ala Gly His
                    165                 170                 175

Val Ser Val Pro Phe Leu Leu Ala Tyr Cys Ser Ser Lys Phe Ala Ala
            180                 185                 190

Val Gly Phe His Lys Thr Leu Thr Asp Glu Leu Ala Ala Leu Gln Ile
        195                 200                 205

Thr Gly Val Lys Thr Thr Cys Leu Cys Pro Asn Phe Val Asn Thr Gly
    210                 215                 220

Phe Ile Lys Asn Pro Ser Thr Ser Leu Gly Pro Thr Leu Glu Pro Glu
225                 230                 235                 240

Glu Val Val Asn Arg Leu Met His Gly Ile Leu Thr Glu Gln Lys Met
                245                 250                 255

Ile Phe Ile Pro Ser Ser Ile Ala Phe Leu Thr Thr Leu Glu Arg Ile
            260                 265                 270

Leu Pro Glu Arg Phe Leu Ala Val Leu Lys Arg Lys Ile Ser Val Lys
        275                 280                 285

Phe Asp Ala Val Ile Gly Tyr Lys Met Lys Ala Gln Xaa
        290                 295                 300

<210> SEQ ID NO 99
<211> LENGTH: 105
<212> TYPE: PRT
<213> ORGANISM: Homo sapiens
<220> FEATURE:
<221> NAME/KEY: SITE
<222> LOCATION: (105)
<223> OTHER INFORMATION: Xaa equals stop translation

<400> SEQUENCE: 99

Met Trp Tyr Cys Leu Leu Cys Gly Cys Ser Cys His Ala Lys Ala Val
1               5                   10                  15

Pro Ser Val Leu Ser Arg Leu Ser Cys Asn Leu Pro Ala Leu Leu Ser
                20                  25                  30

His Ala Leu Pro Gln Pro Ser Pro Ser Val Gly Ala Pro Pro Gly Ser
            35                  40                  45

Pro Arg Pro Val Pro Pro His Pro Leu Ser Asp Pro His Ser Cys Leu
        50                  55                  60

Pro Thr Pro Ala Phe Arg Gly Leu Cys Ser Pro Pro Leu Cys Pro Leu
65                  70                  75                  80

Leu Pro Pro Arg Phe Ser Leu Lys Leu Pro Pro Leu Ser Leu Asp Pro
                85                  90                  95

Gln Leu Ile Pro Pro Ala Thr Tyr Xaa
            100                 105

<210> SEQ ID NO 100
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 100

Met Cys Met Phe Ser Thr Cys Gly Leu Ser Asn Tyr Leu Ile Ile Thr
1               5                   10                  15

Thr Phe Leu Leu Leu Ser Ile Ser Ser Leu Val Pro Thr Pro Ser
                20                  25                  30
```

```
Lys Leu Phe Asp Ser Ser Ser His Trp Lys Tyr Xaa
        35                  40

<210> SEQ ID NO 101
<211> LENGTH: 50
<212> TYPE: PRT
<213> ORGANISM: Homo sapiens
<220> FEATURE:
<221> NAME/KEY: SITE
<222> LOCATION: (50)
<223> OTHER INFORMATION: Xaa equals stop translation

<400> SEQUENCE: 101

Met His Leu Leu Leu Ser Cys Leu Leu Ala Gly Lys Ala Ser Cys
 1               5                  10                  15

His Val Val Arg Ser Pro Val Asp Asn Pro Leu Trp Gln Gly Asn
                20                  25                  30

Ala Tyr Gly Gln Gln Pro Val Arg Thr Gly Pro Cys Gln Pro His
        35                  40                  45

Lys Xaa
    50

<210> SEQ ID NO 102
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 102

Met Thr Leu Tyr Leu Ser Leu Leu Asn Met Ile Pro Leu Asn Leu Ala
 1               5                  10                  15

Ser Cys Ser Ser His Leu Glu Leu Leu Lys Lys Leu Ile Met Ser Tyr
                20                  25                  30

Arg Val Phe Thr Phe Pro Ile Pro Asp Thr Cys His Leu His Ile Xaa
        35                  40                  45

<210> SEQ ID NO 103
<211> LENGTH: 100
<212> TYPE: PRT
<213> ORGANISM: Homo sapiens
<220> FEATURE:
<221> NAME/KEY: SITE
<222> LOCATION: (100)
<223> OTHER INFORMATION: Xaa equals stop translation

<400> SEQUENCE: 103

Met Tyr Phe Leu Leu Thr Cys Arg Phe Ser Leu His Leu Leu Pro Cys
 1               5                  10                  15

Pro Leu Phe Leu Cys Phe Leu Pro Pro Cys Ser Leu Phe Val Glu Glu
                20                  25                  30

Thr Ser Tyr Leu Cys Phe Val Ser His Gly Met Asn Phe Ala Glu Cys
        35                  40                  45

Ile Phe Thr Cys Ser Leu Met Cys Cys Leu Val Leu His Ile Ser Cys
    50                  55                  60

Lys Leu Thr Val Glu Ser Thr Ser Leu Ile Thr Phe Thr Phe Phe Leu
65                  70                  75                  80

Gly Trp Trp Gly Trp Arg Tyr Thr Gln Leu Phe Pro Phe His Asp Val
                85                  90                  95
```

-continued

```
Ser Ser Arg Xaa
        100

<210> SEQ ID NO 104
<211> LENGTH: 59
<212> TYPE: PRT
<213> ORGANISM: Homo sapiens
<220> FEATURE:
<221> NAME/KEY: SITE
<222> LOCATION: (59)
<223> OTHER INFORMATION: Xaa equals stop translation

<400> SEQUENCE: 104

Met His His Ile Cys Gly Ser Ile Val Leu Leu Cys Leu Phe Asp
 1               5                  10                  15

Leu Cys Met Ala Ala Val Gly Gln Leu His Ile Trp Ser Pro Tyr Ser
            20                  25                  30

Lys Met Gln Ser Thr Leu Leu Thr Ala His Ile Pro Ser Pro Lys Gln
        35                  40                  45

Asn Leu Asn Phe Gln Leu Cys Pro Leu Lys Xaa
    50                  55

<210> SEQ ID NO 105
<211> LENGTH: 65
<212> TYPE: PRT
<213> ORGANISM: Homo sapiens
<220> FEATURE:
<221> NAME/KEY: SITE
<222> LOCATION: (65)
<223> OTHER INFORMATION: Xaa equals stop translation

<400> SEQUENCE: 105

Met Leu Gly Ser Val Cys Arg Ala Leu His Val Leu Thr Cys Leu Leu
 1               5                  10                  15

Leu Ser Ser Asn Pro Val Val Gln Ala Pro Cys Ser Leu Asn Glu Glu
            20                  25                  30

Ser Lys Ser Gln Gly Val Thr Cys Ala Val Leu Pro Ala Gly Asp Leu
        35                  40                  45

Asn Pro Gly Ser Leu Val Ser Ala Cys Val Pro Leu Thr Val Thr Leu
    50                  55                  60

Xaa
 65

<210> SEQ ID NO 106
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 106

Met Pro Cys His Gly Leu Leu Ala Gln Gly Leu Ser Leu Ala Pro Leu
 1               5                  10                  15

Pro Pro Trp Ala Leu Cys Cys Val Gly Val Ser Arg Ala Leu Gln Asp
            20                  25                  30

Ile Gln Gln His Pro Arg Pro Ala Pro Cys Gln Xaa
        35                  40                  45

<210> SEQ ID NO 107
<211> LENGTH: 93
<212> TYPE: PRT
```

```
<213> ORGANISM: Homo sapiens
<220> FEATURE:
<221> NAME/KEY: SITE
<222> LOCATION: (61)
<223> OTHER INFORMATION: Xaa equals any of the naturally occurring
      L-amino acids
<220> FEATURE:
<221> NAME/KEY: SITE
<222> LOCATION: (68)
<223> OTHER INFORMATION: Xaa equals any of the naturally occurring
      L-amino acids
<220> FEATURE:
<221> NAME/KEY: SITE
<222> LOCATION: (93)
<223> OTHER INFORMATION: Xaa equals stop translation

<400> SEQUENCE: 107

Met Gly Ser Thr Trp Gly Ser Pro Gly Trp Val Arg Leu Ala Leu Cys
 1               5                  10                  15

Leu Thr Gly Leu Val Leu Ser Leu Tyr Ala Leu His Val Lys Ala Ala
             20                  25                  30

Arg Ala Arg Asp Arg Asp Tyr Arg Ala Leu Cys Asp Val Gly Thr Ala
         35                  40                  45

Ile Ser Cys Ser Arg Val Phe Ser Ser Arg Leu Pro Xaa Asp Thr Leu
     50                  55                  60

Gly Leu Cys Xaa Asp Ala Ala Glu Leu Pro Gly Val Ser Arg Trp Phe
 65                  70                  75                  80

Cys Leu Pro Gly Leu Asp Pro Val Leu Arg Ala Leu Xaa
             85                  90

<210> SEQ ID NO 108
<211> LENGTH: 26
<212> TYPE: PRT
<213> ORGANISM: Homo sapiens
<220> FEATURE:
<221> NAME/KEY: SITE
<222> LOCATION: (26)
<223> OTHER INFORMATION: Xaa equals stop translation

<400> SEQUENCE: 108

Met Gln Thr Ile His Phe Thr Pro Ala Val Leu His Phe Leu Phe Leu
 1               5                  10                  15

Trp Ser Ser Thr Trp Ser Val Ser Ile Xaa
             20                  25

<210> SEQ ID NO 109
<211> LENGTH: 68
<212> TYPE: PRT
<213> ORGANISM: Homo sapiens
<220> FEATURE:
<221> NAME/KEY: SITE
<222> LOCATION: (68)
<223> OTHER INFORMATION: Xaa equals stop translation

<400> SEQUENCE: 109

Met Cys Ile Leu His Ser His Cys Leu Leu Phe Leu Asn Leu Asn Gln
 1               5                  10                  15

Val Val Cys Phe His Gly Asn Phe Ser Leu Ser Cys Phe Cys Gln Thr
             20                  25                  30

Gln Ile Ser Tyr Ile Asn Ile Phe Ser Gly Lys Asn Gly Cys Asp Ser
         35                  40                  45

Lys Leu Glu His Leu Leu Phe Tyr Phe Arg Lys Ser Leu Leu Asn Ile
     50                  55                  60

Phe Leu Val Xaa
```

<210> SEQ ID NO 110
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 110

Met Ser Thr Gly Ser Leu Met Thr Trp Trp Leu Arg Ser Ser Leu
 1               5                  10                  15

Arg Val Ala Leu Cys Gly Pro Ala Arg Thr Met Thr Glu Met Cys Ser
            20                  25                  30

Gln Thr Ser Trp Pro Arg Ala Leu Ala Pro Leu Ala Xaa
        35                  40                  45

<210> SEQ ID NO 111
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 111

Met His Asn Leu Leu Leu Ser Cys Val Ile Phe Asn Phe Pro Leu Val
 1               5                  10                  15

Phe Ile Val Ala Arg Thr Pro Tyr Leu Pro Ser Leu Leu Ser Ile Cys
            20                  25                  30

Asn Leu Glu Ala Pro Val Tyr Leu Arg Ile Asp Pro Gly Trp Pro His
        35                  40                  45

Leu Cys Met Ala Xaa
    50

<210> SEQ ID NO 112
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 112

Met Val Asp Leu Ile Leu Leu Leu Phe His Ser Ala Val Gly Cys Asn
 1               5                  10                  15

Leu Lys Ser Arg Gly Ala Leu Gln Thr Leu His Asp Ser Met Thr Leu
            20                  25                  30

Ser Ser Phe Tyr Ser Ser Lys Thr Ser Leu Ile Xaa
        35                  40

<210> SEQ ID NO 113
<211> LENGTH: 65
<212> TYPE: PRT
<213> ORGANISM: Homo sapiens
<220> FEATURE:
<221> NAME/KEY: SITE
<222> LOCATION: (65)
<223> OTHER INFORMATION: Xaa equals stop translation

<400> SEQUENCE: 113

```
Met Phe Cys Pro Ser Gln Met Asp Leu Glu Pro Phe Trp Phe Cys Leu
 1               5                  10                  15

Met Ala Ala Leu Phe Ile Phe Tyr Cys Leu Leu Leu Tyr Phe Leu His
            20                  25                  30

Ile Phe Lys Asp Gly Val Ser Arg Leu Pro Ser Thr Glu Tyr Lys Tyr
            35                  40                  45

Lys Ser Leu Ser Val Leu Val Phe Cys Lys Lys His Asp Cys Ser Phe
        50                  55                  60

Xaa
 65
```

```
<210> SEQ ID NO 114
<211> LENGTH: 70
<212> TYPE: PRT
<213> ORGANISM: Homo sapiens
<220> FEATURE:
<221> NAME/KEY: SITE
<222> LOCATION: (70)
<223> OTHER INFORMATION: Xaa equals stop translation

<400> SEQUENCE: 114
```

```
Met Phe Glu Ser Ala Gly Gln Val Leu Leu His Ile Ala Gly Leu Gln
 1               5                  10                  15

Val Trp Val Phe Leu Thr Cys Leu Ser Ser Phe Leu Val Pro Leu Ser
            20                  25                  30

Tyr Ser Gly Tyr Ile Pro Leu Met Val Met Ala Glu Ala His Gln Met
            35                  40                  45

Ala Ser Pro Thr Thr Gln Ala Leu Phe Lys Leu Leu Phe Ala Ser His
        50                  55                  60

Leu Leu Thr Phe Tyr Xaa
 65                  70
```

```
<210> SEQ ID NO 115
<211> LENGTH: 54
<212> TYPE: PRT
<213> ORGANISM: Homo sapiens
<220> FEATURE:
<221> NAME/KEY: SITE
<222> LOCATION: (54)
<223> OTHER INFORMATION: Xaa equals stop translation

<400> SEQUENCE: 115
```

```
Met Ala Trp Val Gln Ile Pro Leu Leu Pro Phe Thr Ser Cys Val Thr
 1               5                  10                  15

Leu Gly Lys Tyr Leu Asn Leu Ser Val Pro His Phe Ser His Leu His
            20                  25                  30

Lys Glu Asn Asn Ser Leu Leu Leu His Arg Val Val Met Ser Leu Thr
            35                  40                  45

Met Ser His Tyr Val Xaa
        50
```

```
<210> SEQ ID NO 116
<211> LENGTH: 41
<212> TYPE: PRT
<213> ORGANISM: Homo sapiens

<400> SEQUENCE: 116
```

```
Met Phe Ser Leu Pro Gln Tyr Leu Ile Tyr Phe Val Leu Ser Ile Leu
 1               5                  10                  15

Val Val Ser Thr Leu Phe Ser Leu Pro Leu Phe Leu Val Pro Leu Arg
```

```
                    20                  25                  30

Gly Glu Lys Lys Asp Asp Asn Gly Val
            35                  40

<210> SEQ ID NO 117
<211> LENGTH: 52
<212> TYPE: PRT
<213> ORGANISM: Homo sapiens

<400> SEQUENCE: 117

Met Ser Lys Ala Arg Phe Pro Phe Leu Ala Phe Pro Pro Leu Val Leu
  1               5                  10                  15

Cys Leu Glu His Ser Gln Ala Ser Leu Gly Thr Arg Leu Pro Val Val
                 20                  25                  30

Thr Pro Ser Ser Leu Pro Ser Ser Cys Lys Gly Ile Gly Cys Gly Phe
             35                  40                  45

Leu Glu Leu Gly
         50

<210> SEQ ID NO 118
<211> LENGTH: 71
<212> TYPE: PRT
<213> ORGANISM: Homo sapiens
<220> FEATURE:
<221> NAME/KEY: SITE
<222> LOCATION: (71)
<223> OTHER INFORMATION: Xaa equals stop translation

<400> SEQUENCE: 118

Met Trp Arg Val Thr Arg Arg Gly Glu Leu Thr Ser Cys Leu Ser Gly
  1               5                  10                  15

Ala Thr Tyr Leu Phe Phe Tyr Gly Val Ser Thr Pro His Ala Leu Ala
                 20                  25                  30

Thr Tyr Leu Arg Lys Leu Leu Asp Leu Lys Ser Glu Ser Phe Lys Gln
             35                  40                  45

Met Asn Val Cys Phe Val Leu His Leu Pro Trp Glu Ile Leu Asn Ile
         50                  55                  60

Tyr Arg Asn Arg Val Ser Xaa
 65                  70

<210> SEQ ID NO 119
<211> LENGTH: 17
<212> TYPE: PRT
<213> ORGANISM: Homo sapiens
<220> FEATURE:
<221> NAME/KEY: SITE
<222> LOCATION: (17)
<223> OTHER INFORMATION: Xaa equals stop translation

<400> SEQUENCE: 119

Met Leu Leu Ser Ile Ile Cys Leu Val Arg Ser Leu Phe His His Leu
  1               5                  10                  15

Xaa

<210> SEQ ID NO 120
<211> LENGTH: 25
<212> TYPE: PRT
<213> ORGANISM: Homo sapiens
<220> FEATURE:
<221> NAME/KEY: SITE
<222> LOCATION: (25)
<223> OTHER INFORMATION: Xaa equals stop translation
```

```
<400> SEQUENCE: 120

Met Val Phe Leu Trp Ile Ser Tyr Ala Val Lys Ala Phe Leu Val Trp
 1               5                  10                  15

Thr Leu Gln Leu Ala Ala Glu Phe Xaa
             20                  25

<210> SEQ ID NO 121
<211> LENGTH: 27
<212> TYPE: PRT
<213> ORGANISM: Homo sapiens
<220> FEATURE:
<221> NAME/KEY: SITE
<222> LOCATION: (27)
<223> OTHER INFORMATION: Xaa equals stop translation

<400> SEQUENCE: 121

Met Phe Ser Leu Pro Gln Tyr Leu Lys Leu Val Leu Ser Ile Leu Val
 1               5                  10                  15

Val Ser Thr Leu Phe Ser Leu Pro Phe Ser Xaa
             20                  25

<210> SEQ ID NO 122
<211> LENGTH: 18
<212> TYPE: PRT
<213> ORGANISM: Homo sapiens
<220> FEATURE:
<221> NAME/KEY: SITE
<222> LOCATION: (18)
<223> OTHER INFORMATION: Xaa equals stop translation

<400> SEQUENCE: 122

Met Ser Lys Ala Arg Phe Pro Phe Leu Leu Ser Leu Arg Trp Phe Ser
 1               5                  10                  15

Ala Xaa

<210> SEQ ID NO 123
<211> LENGTH: 153
<212> TYPE: PRT
<213> ORGANISM: Homo sapiens

<400> SEQUENCE: 123

His Glu Leu Gly Gly Leu Leu Ala Asp Phe Leu Leu Ser Arg Lys Ile
 1               5                  10                  15

Leu Arg Leu Ile Thr Ile Arg Lys Leu Phe Thr Ala Ile Gly Val Leu
             20                  25                  30

Phe Pro Ser Val Ile Leu Val Ser Leu Pro Trp Val Arg Ser Ser His
         35                  40                  45

Ser Met Thr Met Thr Phe Leu Val Leu Ser Ser Ala Ile Ser Ser Phe
     50                  55                  60

Cys Glu Ser Gly Ala Leu Val Asn Phe Leu Asp Ile Ala Pro Arg Tyr
 65                  70                  75                  80

Thr Gly Phe Leu Lys Gly Leu Leu Gln Val Phe Ala His Ile Ala Gly
                 85                  90                  95

Ala Ile Ser Pro Thr Ala Ala Gly Phe Phe Ile Ser Gln Asp Ser Glu
                100                 105                 110

Phe Gly Trp Arg Asn Val Phe Leu Leu Ser Ala Ala Val Asn Ile Ser
            115                 120                 125

Gly Leu Val Phe Tyr Leu Ile Phe Gly Arg Ala Asp Val Gln Asp Trp
        130                 135                 140

Ala Lys Glu Gln Thr Phe Thr His Leu
```

145            150

<210> SEQ ID NO 124
<211> LENGTH: 108
<212> TYPE: PRT
<213> ORGANISM: Homo sapiens

<400> SEQUENCE: 124

Leu Met Lys Asn Pro Ala Ala Val Gly Glu Met Ala Pro Ala Met Cys
1               5                   10                  15

Ala Lys Thr Cys Asn Ser Pro Leu Arg Lys Pro Val Tyr Arg Gly Ala
            20                  25                  30

Ile Ser Lys Lys Leu Thr Arg Ala Pro Asp Ser Gln Lys Leu Leu Met
        35                  40                  45

Ala Glu Asp Ser Thr Lys Lys Val Met Val Met Leu Trp Leu Asp Leu
    50                  55                  60

Thr Gln Gly Arg Asp Thr Arg Ile Thr Asp Gly Lys Arg Thr Pro Met
65                  70                  75                  80

Ala Val Lys Ser Phe Leu Met Val Met Ser Leu Arg Ile Phe Leu Glu
                85                  90                  95

Arg Arg Lys Ser Ala Ser Arg Pro Pro Ser Ser Cys
            100                 105

<210> SEQ ID NO 125
<211> LENGTH: 22
<212> TYPE: PRT
<213> ORGANISM: Homo sapiens

<400> SEQUENCE: 125

His Glu Leu Gly Gly Leu Leu Ala Asp Phe Leu Leu Ser Arg Lys Ile
1               5                   10                  15

Leu Arg Leu Ile Thr Ile
            20

<210> SEQ ID NO 126
<211> LENGTH: 24
<212> TYPE: PRT
<213> ORGANISM: Homo sapiens

<400> SEQUENCE: 126

Arg Lys Leu Phe Thr Ala Ile Gly Val Leu Phe Pro Ser Val Ile Leu
1               5                   10                  15

Val Ser Leu Pro Trp Val Arg Ser
            20

<210> SEQ ID NO 127
<211> LENGTH: 24
<212> TYPE: PRT
<213> ORGANISM: Homo sapiens

<400> SEQUENCE: 127

Ser His Ser Met Thr Met Thr Phe Leu Val Leu Ser Ser Ala Ile Ser
1               5                   10                  15

Ser Phe Cys Glu Ser Gly Ala Leu
            20

<210> SEQ ID NO 128
<211> LENGTH: 23
<212> TYPE: PRT
<213> ORGANISM: Homo sapiens

<400> SEQUENCE: 128

Val Asn Phe Leu Asp Ile Ala Pro Arg Tyr Thr Gly Phe Leu Lys Gly
1               5                   10                  15

Leu Leu Gln Val Phe Ala His
            20

<210> SEQ ID NO 129
<211> LENGTH: 24
<212> TYPE: PRT
<213> ORGANISM: Homo sapiens

<400> SEQUENCE: 129

Ile Ala Gly Ala Ile Ser Pro Thr Ala Ala Gly Phe Phe Ile Ser Gln
1               5                   10                  15

Asp Ser Glu Phe Gly Trp Arg Asn
            20

<210> SEQ ID NO 130
<211> LENGTH: 36
<212> TYPE: PRT
<213> ORGANISM: Homo sapiens

<400> SEQUENCE: 130

Val Phe Leu Leu Ser Ala Ala Val Asn Ile Ser Gly Leu Val Phe Tyr
1               5                   10                  15

Leu Ile Phe Gly Arg Ala Asp Val Gln Asp Trp Ala Lys Glu Gln Thr
            20                  25                  30

Phe Thr His Leu
        35

<210> SEQ ID NO 131
<211> LENGTH: 28
<212> TYPE: PRT
<213> ORGANISM: Homo sapiens

<400> SEQUENCE: 131

Leu Met Lys Asn Pro Ala Ala Val Gly Glu Met Ala Pro Ala Met Cys
1               5                   10                  15

Ala Lys Thr Cys Asn Ser Pro Leu Arg Lys Pro Val
            20                  25

<210> SEQ ID NO 132
<211> LENGTH: 31
<212> TYPE: PRT
<213> ORGANISM: Homo sapiens

<400> SEQUENCE: 132

Tyr Arg Gly Ala Ile Ser Lys Lys Leu Thr Arg Ala Pro Asp Ser Gln
1               5                   10                  15

Lys Leu Leu Met Ala Glu Asp Ser Thr Lys Lys Val Met Val Met
            20                  25                  30

<210> SEQ ID NO 133
<211> LENGTH: 49
<212> TYPE: PRT
<213> ORGANISM: Homo sapiens

<400> SEQUENCE: 133

Leu Trp Leu Asp Leu Thr Gln Gly Arg Asp Thr Arg Ile Thr Asp Gly
1               5                   10                  15

Lys Arg Thr Pro Met Ala Val Lys Ser Phe Leu Met Val Met Ser Leu

-continued

```
                    20                  25                  30
Arg Ile Phe Leu Glu Arg Arg Lys Ser Ala Ser Arg Pro Ser Ser
            35                  40                  45
Cys

<210> SEQ ID NO 134
<211> LENGTH: 106
<212> TYPE: PRT
<213> ORGANISM: Homo sapiens
<220> FEATURE:
<221> NAME/KEY: SITE
<222> LOCATION: (72)
<223> OTHER INFORMATION: Xaa equals any of the naturally occurring
      L-amino acids

<400> SEQUENCE: 134

Glu Tyr Ser Thr Pro Asp Thr Val His Leu Arg Lys Thr Ile Leu Phe
 1               5                  10                  15

Ser Val Lys Val Pro Val Leu Ser Glu Lys Met Tyr Cys Ile Cys Pro
                20                  25                  30

Lys Ser Ser Val Met Phe Arg Ala Arg His Cys Ser Cys Glu Ser Val
            35                  40                  45

Ser Ser Ser Tyr Asn Cys Met Ser Trp Leu Met Lys Tyr Thr Trp His
    50                  55                  60

Ala Leu Thr Ile Ser Met Glu Xaa Tyr Lys Glu Met Gly Ser Lys Pro
65                  70                  75                  80

Ala Glu Leu Tyr His Val Lys Asn Glu Leu Thr Ala Ala Val Thr Gly
                85                  90                  95

Asp Lys Glu Leu Pro Ser Asp Leu Gly Thr
            100                 105

<210> SEQ ID NO 135
<211> LENGTH: 20
<212> TYPE: PRT
<213> ORGANISM: Homo sapiens
<220> FEATURE:
<221> NAME/KEY: SITE
<222> LOCATION: (15)
<223> OTHER INFORMATION: Xaa equals any of the naturally occurring
      L-amino acids

<400> SEQUENCE: 135

Asn Gln Gly Ser Ala Glu Gln Gln Trp Ala Pro Leu Gln Ala Xaa Lys
 1               5                  10                  15

Leu Glu Arg Gln
            20

<210> SEQ ID NO 136
<211> LENGTH: 42
<212> TYPE: PRT
<213> ORGANISM: Homo sapiens
<220> FEATURE:
<221> NAME/KEY: SITE
<222> LOCATION: (12)
<223> OTHER INFORMATION: Xaa equals any of the naturally occurring
      L-amino acids
<220> FEATURE:
<221> NAME/KEY: SITE
<222> LOCATION: (13)
<223> OTHER INFORMATION: Xaa equals any of the naturally occurring
      L-amino acids
<220> FEATURE:
<221> NAME/KEY: SITE
<222> LOCATION: (37)
<223> OTHER INFORMATION: Xaa equals any of the naturally occurring
```

L-amino acids

<400> SEQUENCE: 136

Ile Arg His Glu Thr Leu Arg Asn Thr Asp Ala Xaa Xaa Gly Ile Val
1               5                   10                  15

Ile Tyr Ala Gly His Glu Thr Lys Ala Leu Leu Asn Asn Ser Gly Pro
            20                  25                  30

Arg Tyr Lys Arg Xaa Ser Trp Arg Gly Arg
        35                  40

<210> SEQ ID NO 137
<211> LENGTH: 129
<212> TYPE: PRT
<213> ORGANISM: Homo sapiens
<220> FEATURE:
<221> NAME/KEY: SITE
<222> LOCATION: (13)
<223> OTHER INFORMATION: Xaa equals any of the naturally occurring
      L-amino acids

<400> SEQUENCE: 137

Tyr Ser Ser Ala Gly Phe Asp Pro Ile Ser Leu Tyr Xaa Ser Ile Glu
1               5                   10                  15

Ile Val Lys Ala Cys Gln Val Tyr Phe Ile Asn Gln Asp Met Gln Leu
            20                  25                  30

Tyr Asp Glu Glu Thr Asp Ser Gln Leu Gln Cys Arg Ala Leu Asn Ile
        35                  40                  45

Thr Glu Asp Leu Gly Gln Ile Gln Tyr Ile Phe Ser Asp Lys Thr Gly
    50                  55                  60

Thr Leu Thr Glu Asn Lys Met Val Phe Arg Arg Cys Thr Val Ser Gly
65                  70                  75                  80

Val Glu Tyr Ser His Asp Ala Asn Glu Gly Leu Leu Arg Asp Ala Gln
                85                  90                  95

Trp Ser Thr Arg Leu Ala Gly Ser Ile Ser Ile Ser Phe Ser Gly Leu
            100                 105                 110

Leu Thr Gly Pro Cys Cys Phe Asp Ser Ala Pro Cys Leu Cys Leu Lys
        115                 120                 125

Phe

<210> SEQ ID NO 138
<211> LENGTH: 26
<212> TYPE: PRT
<213> ORGANISM: Homo sapiens
<220> FEATURE:
<221> NAME/KEY: SITE
<222> LOCATION: (13)
<223> OTHER INFORMATION: Xaa equals any of the naturally occurring
      L-amino acids

<400> SEQUENCE: 138

Tyr Ser Ser Ala Gly Phe Asp Pro Ile Ser Leu Tyr Xaa Ser Ile Glu
1               5                   10                  15

Ile Val Lys Ala Cys Gln Val Tyr Phe Ile
            20                  25

<210> SEQ ID NO 139
<211> LENGTH: 26
<212> TYPE: PRT
<213> ORGANISM: Homo sapiens

<400> SEQUENCE: 139

-continued

```
Asn Gln Asp Met Gln Leu Tyr Asp Glu Thr Asp Ser Gln Leu Gln
 1               5                  10                  15

Cys Arg Ala Leu Asn Ile Thr Glu Asp Leu
             20                  25

<210> SEQ ID NO 140
<211> LENGTH: 28
<212> TYPE: PRT
<213> ORGANISM: Homo sapiens

<400> SEQUENCE: 140

Gly Gln Ile Gln Tyr Ile Phe Ser Asp Lys Thr Gly Thr Leu Thr Glu
 1               5                  10                  15

Asn Lys Met Val Phe Arg Arg Cys Thr Val Ser Gly
             20                  25

<210> SEQ ID NO 141
<211> LENGTH: 28
<212> TYPE: PRT
<213> ORGANISM: Homo sapiens

<400> SEQUENCE: 141

Val Glu Tyr Ser His Asp Ala Asn Glu Gly Leu Leu Arg Asp Ala Gln
 1               5                  10                  15

Trp Ser Thr Arg Leu Ala Gly Ser Ile Ser Ile Ser
             20                  25

<210> SEQ ID NO 142
<211> LENGTH: 21
<212> TYPE: PRT
<213> ORGANISM: Homo sapiens

<400> SEQUENCE: 142

Phe Ser Gly Leu Leu Thr Gly Pro Cys Cys Phe Asp Ser Ala Pro Cys
 1               5                  10                  15

Leu Cys Leu Lys Phe
             20

<210> SEQ ID NO 143
<211> LENGTH: 40
<212> TYPE: PRT
<213> ORGANISM: Homo sapiens

<400> SEQUENCE: 143

His Glu Leu Gly Pro Val Cys Leu His Ala Ile Met Leu Ala Glu Leu
 1               5                  10                  15

Ile Phe Leu Phe Arg Ser Leu His Gly Ile Leu Ala Ser Ala Gly Thr
             20                  25                  30

Ile Gly Ala Val Ala Ala Trp Leu
         35                  40

<210> SEQ ID NO 144
<211> LENGTH: 195
<212> TYPE: PRT
<213> ORGANISM: Homo sapiens
<220> FEATURE:
<221> NAME/KEY: SITE
<222> LOCATION: (5)
<223> OTHER INFORMATION: Xaa equals any of the naturally occurring
      L-amino acids

<400> SEQUENCE: 144

Asp Phe Gly Thr Xaa Ser Asp Pro Lys Leu Phe Glu Met Ile Lys Tyr
```

```
                 1               5                  10                  15
              Cys Leu Leu Lys Ile Leu Lys Gln Tyr Gln Thr Leu Arg Glu Ala Leu
                            20                  25                  30

Val Ala Ala Gly Lys Glu Val Ile Trp His Gly Arg Thr Asn Asp Glu
                            35                  40                  45

Pro Ala His Tyr Cys Ser Ile Cys Glu Val Glu Val Phe Asn Leu Leu
                            50                  55                  60

Phe Val Thr Asn Glu Ser Asn Thr Gln Lys Thr Tyr Ile Val His Cys
               65                  70                  75                  80

His Asp Cys Ala Arg Lys Thr Ser Lys Ser Leu Glu Asn Phe Val Val
                                85                  90                  95

Leu Glu Gln Tyr Lys Met Glu Asp Leu Ile Gln Val Tyr Asp Gln Phe
                            100                 105                 110

Thr Leu Ala Ser Pro Trp Pro Met Asp Gln Ser Ala Phe Thr Ser
                            115                 120                 125

Ser Leu Leu Arg Pro Ile Lys Ala Leu Gly Ser Gly Arg Ala Glu Gln
                            130                 135                 140

Thr Ser Gly Asp Gln Leu Gln Lys Gly Ala Thr His Ser Arg Ala Ser
              145                 150                 155                 160

Ser Leu Leu Arg Ala Ala Glu Met Thr Arg Arg Pro Ala Ser Arg Glu
                                165                 170                 175

Glu Leu Pro Asp Pro Gly Leu Phe Cys His Ser Ile Lys Leu Leu Phe
                            180                 185                 190

Val Leu Leu
                            195

<210> SEQ ID NO 145
<211> LENGTH: 26
<212> TYPE: PRT
<213> ORGANISM: Homo sapiens
<220> FEATURE:
<221> NAME/KEY: SITE
<222> LOCATION: (5)
<223> OTHER INFORMATION: Xaa equals any of the naturally occurring
      L-amino acids

<400> SEQUENCE: 145

Asp Phe Gly Thr Xaa Ser Asp Pro Lys Leu Phe Glu Met Ile Lys Tyr
 1               5                  10                  15

Cys Leu Leu Lys Ile Leu Lys Gln Tyr Gln
            20                  25

<210> SEQ ID NO 146
<211> LENGTH: 28
<212> TYPE: PRT
<213> ORGANISM: Homo sapiens

<400> SEQUENCE: 146

Thr Leu Arg Glu Ala Leu Val Ala Ala Gly Lys Glu Val Ile Trp His
 1               5                  10                  15

Gly Arg Thr Asn Asp Glu Pro Ala His Tyr Cys Ser
            20                  25

<210> SEQ ID NO 147
<211> LENGTH: 26
<212> TYPE: PRT
<213> ORGANISM: Homo sapiens

<400> SEQUENCE: 147
```

Ile Cys Glu Val Glu Val Phe Asn Leu Phe Val Thr Asn Glu Ser
1               5                   10                  15

Asn Thr Gln Lys Thr Tyr Ile Val His Cys
                20                  25

<210> SEQ ID NO 148
<211> LENGTH: 30
<212> TYPE: PRT
<213> ORGANISM: Homo sapiens

<400> SEQUENCE: 148

His Asp Cys Ala Arg Lys Thr Ser Lys Ser Leu Glu Asn Phe Val Val
1               5                   10                  15

Leu Glu Gln Tyr Lys Met Glu Asp Leu Ile Gln Val Tyr Asp
                20                  25                  30

<210> SEQ ID NO 149
<211> LENGTH: 30
<212> TYPE: PRT
<213> ORGANISM: Homo sapiens

<400> SEQUENCE: 149

Gln Phe Thr Leu Ala Ser Pro Trp Pro Pro Met Asp Gln Ser Ala Phe
1               5                   10                  15

Thr Ser Ser Leu Leu Arg Pro Ile Lys Ala Leu Gly Ser Gly
                20                  25                  30

<210> SEQ ID NO 150
<211> LENGTH: 29
<212> TYPE: PRT
<213> ORGANISM: Homo sapiens

<400> SEQUENCE: 150

Arg Ala Glu Gln Thr Ser Gly Asp Gln Leu Gln Lys Gly Ala Thr His
1               5                   10                  15

Ser Arg Ala Ser Ser Leu Leu Arg Ala Ala Glu Met Thr
                20                  25

<210> SEQ ID NO 151
<211> LENGTH: 26
<212> TYPE: PRT
<213> ORGANISM: Homo sapiens

<400> SEQUENCE: 151

Arg Arg Pro Ala Ser Arg Glu Glu Leu Pro Asp Pro Gly Leu Phe Cys
1               5                   10                  15

His Ser Ile Lys Leu Leu Phe Val Leu Leu
                20                  25

<210> SEQ ID NO 152
<211> LENGTH: 25
<212> TYPE: PRT
<213> ORGANISM: Homo sapiens

<400> SEQUENCE: 152

Leu Pro Gly Asn Phe Arg Pro Pro Arg Val Ile Leu Thr Phe Gln Trp
1               5                   10                  15

Arg Phe Tyr Leu Ser Phe Arg Lys Leu
                20                  25

<210> SEQ ID NO 153
<211> LENGTH: 95

```
<212> TYPE: PRT
<213> ORGANISM: Homo sapiens

<400> SEQUENCE: 153

Tyr Leu Leu Leu Pro Cys Gly Leu Leu Ser Phe Trp Met Cys Gly Ala
 1               5                  10                  15

Leu Val Val Ser Pro Phe Val Gln Asn Gly Gln Gly Gln Arg Leu Arg
                20                  25                  30

Glu Ala Arg Ser Leu Cys Leu Leu Lys Gly Thr Thr Trp Ile Phe Leu
            35                  40                  45

Met Leu Ser Leu Pro His Phe Leu Val Gln Glu Leu Lys Phe Ser Asn
     50                  55                  60

Asn Phe Phe Ser Thr Val Val Ile Phe Ser Thr Ser Gly Phe Leu Gln
 65                  70                  75                  80

Pro Thr Leu Ile Phe Leu Lys Leu Ser Trp Lys Ser Thr His Leu
                85                  90                  95

<210> SEQ ID NO 154
<211> LENGTH: 31
<212> TYPE: PRT
<213> ORGANISM: Homo sapiens
<220> FEATURE:
<221> NAME/KEY: SITE
<222> LOCATION: (1)
<223> OTHER INFORMATION: Xaa equals any of the naturally occurring
      L-amino acids
<220> FEATURE:
<221> NAME/KEY: SITE
<222> LOCATION: (5)
<223> OTHER INFORMATION: Xaa equals any of the naturally occurring
      L-amino acids
<220> FEATURE:
<221> NAME/KEY: SITE
<222> LOCATION: (6)
<223> OTHER INFORMATION: Xaa equals any of the naturally occurring
      L-amino acids

<400> SEQUENCE: 154

Xaa Ile Pro Pro Xaa Xaa Leu Pro Gly Asn Phe Arg Pro Pro Arg Val
 1               5                  10                  15

Ile Leu Thr Phe Gln Trp Arg Phe Tyr Leu Ser Phe Arg Lys Leu
                20                  25                  30

<210> SEQ ID NO 155
<211> LENGTH: 64
<212> TYPE: PRT
<213> ORGANISM: Homo sapiens

<400> SEQUENCE: 155

Tyr Met Met Val His Cys Lys Tyr Ser Val Tyr Asn Leu Leu Asn Lys
 1               5                  10                  15

Trp Ile Gly Phe Ser Ile Phe Pro His Trp Thr Trp Ile Asp Leu Glu
                20                  25                  30

Ile Gly Gly Leu Asn Leu Gln Val Glu Ile Lys Gly Pro Asn Asn Cys
            35                  40                  45

Arg Val Ala Gly Glu Gly Arg Tyr Lys Cys Ser Lys Gly Gly Ser Arg
     50                  55                  60

<210> SEQ ID NO 156
<211> LENGTH: 74
<212> TYPE: PRT
<213> ORGANISM: Homo sapiens
<220> FEATURE:
<221> NAME/KEY: SITE
```

```
<222> LOCATION: (53)
<223> OTHER INFORMATION: Xaa equals any of the naturally occurring
      L-amino acids
<220> FEATURE:
<221> NAME/KEY: SITE
<222> LOCATION: (60)
<223> OTHER INFORMATION: Xaa equals any of the naturally occurring
      L-amino acids
<220> FEATURE:
<221> NAME/KEY: SITE
<222> LOCATION: (61)
<223> OTHER INFORMATION: Xaa equals any of the naturally occurring
      L-amino acids
<220> FEATURE:
<221> NAME/KEY: SITE
<222> LOCATION: (72)
<223> OTHER INFORMATION: Xaa equals any of the naturally occurring
      L-amino acids
<220> FEATURE:
<221> NAME/KEY: SITE
<222> LOCATION: (73)
<223> OTHER INFORMATION: Xaa equals any of the naturally occurring
      L-amino acids

<400> SEQUENCE: 156

Met Ser Ala Ala Leu Trp Thr Tyr Met Arg Phe Leu Ala Cys Leu Asn
 1               5                  10                  15

His Ser Ser Gly Ser Met Tyr Leu Ser Val Asn Ser Thr Pro Val Leu
            20                  25                  30

Leu Leu Leu Leu Val Pro Asn Ser Ala Arg Ala Arg Ala Glu Phe Leu
        35                  40                  45

Gln Pro Gly Gly Xaa Thr Ser Ser Arg Ala Ala Xaa Xaa Ala Val Glu
    50                  55                  60

Leu Gln Leu Leu Phe Pro Leu Xaa Xaa Gly
65                  70

<210> SEQ ID NO 157
<211> LENGTH: 65
<212> TYPE: PRT
<213> ORGANISM: Homo sapiens

<400> SEQUENCE: 157

Phe Arg Gln Ala Arg Asn Leu Met Tyr Val His Asn Ala Ala Asp Ile
 1               5                  10                  15

His Ser Ser Leu Pro Gln His Ile Thr Val Ile Ser Pro Arg Glu Leu
            20                  25                  30

Cys His Thr Phe Ser Leu Leu Lys Pro Ala Thr Leu Asp Leu Leu Cys
        35                  40                  45

Ser Leu Ser Val Gly Asn Leu Phe Arg Ile Ser Glu Arg Gln Cys Lys
    50                  55                  60

His
65

<210> SEQ ID NO 158
<211> LENGTH: 56
<212> TYPE: PRT
<213> ORGANISM: Homo sapiens
<220> FEATURE:
<221> NAME/KEY: SITE
<222> LOCATION: (55)
<223> OTHER INFORMATION: Xaa equals any of the naturally occurring
      L-amino acids

<400> SEQUENCE: 158

Arg Val Asn Val Ser Ser Ile Met Asp Ile His Glu Val Pro Gly Leu
 1               5                  10                  15
```

```
Ser Lys Ser Gln Leu Trp Phe Asn Val Pro Val Cys Gln Leu His Thr
            20                  25                  30

Cys Val Ala Val Ala Ala Arg Ala Glu Phe Gly Thr Ser Ser Cys Arg
        35                  40                  45

Ile Pro Ala Ala Arg Gly Xaa His
    50                  55

<210> SEQ ID NO 159
<211> LENGTH: 26
<212> TYPE: PRT
<213> ORGANISM: Homo sapiens

<400> SEQUENCE: 159

Ile Arg His Glu Gly Asn Ser Cys Thr Asn Lys Thr Ala His Ala Val
 1               5                  10                  15

Leu Thr Ala Ser Tyr Thr Glu Cys Ser Cys
            20                  25

<210> SEQ ID NO 160
<211> LENGTH: 49
<212> TYPE: PRT
<213> ORGANISM: Homo sapiens
<220> FEATURE:
<221> NAME/KEY: SITE
<222> LOCATION: (43)
<223> OTHER INFORMATION: Xaa equals any of the naturally occurring
      L-amino acids

<400> SEQUENCE: 160

Tyr Lys Val Val Leu Val Trp Arg Glu Asp Gln Ser Ser His Lys Ile
 1               5                  10                  15

His Leu Ser Gln Thr Leu Ile Gln Asn Lys Ala Leu Thr Leu Phe Asn
            20                  25                  30

Ser Met Lys Ala Glu Arg Gly Glu Ala Xaa Gly Lys Asn Val Ser
        35                  40                  45

Ser

<210> SEQ ID NO 161
<211> LENGTH: 91
<212> TYPE: PRT
<213> ORGANISM: Homo sapiens
<220> FEATURE:
<221> NAME/KEY: SITE
<222> LOCATION: (87)
<223> OTHER INFORMATION: Xaa equals any of the naturally occurring
      L-amino acids

<400> SEQUENCE: 161

Asp Gly Glu Leu Ser Lys Cys Cys Met Cys Ser Asp Tyr Thr Ile Asp
 1               5                  10                  15

Cys Tyr Phe Pro Ile Ser Leu Pro Leu Gly Arg Pro Tyr Tyr Leu
            20                  25                  30

Arg His Asn Ile Glu Ile Arg Pro Tyr Ile Asn His Thr Met Ala Ser
        35                  40                  45

Lys Gly Ser Ser Lys Arg Met Gly Cys Thr Ser Phe Thr Leu Thr Gln
    50                  55                  60

Lys Leu Glu Ile Ile Ile Leu Ser Glu Lys Gly Met Trp Lys Ala Glu
65                  70                  75                  80

Ile Gly Gln Lys Leu Gly Xaa Leu His His Ser
                85                  90
```

```
<210> SEQ ID NO 162
<211> LENGTH: 24
<212> TYPE: PRT
<213> ORGANISM: Homo sapiens

<400> SEQUENCE: 162

Tyr Lys Val Val Leu Val Trp Arg Glu Asp Gln Ser Ser His Lys Ile
 1               5                  10                  15

His Leu Ser Gln Thr Leu Ile Gln
            20

<210> SEQ ID NO 163
<211> LENGTH: 25
<212> TYPE: PRT
<213> ORGANISM: Homo sapiens
<220> FEATURE:
<221> NAME/KEY: SITE
<222> LOCATION: (19)
<223> OTHER INFORMATION: Xaa equals any of the naturally occurring
      L-amino acids

<400> SEQUENCE: 163

Asn Lys Ala Leu Thr Leu Phe Asn Ser Met Lys Ala Glu Arg Gly Glu
 1               5                  10                  15

Glu Ala Xaa Gly Lys Asn Val Ser Ser
            20                  25

<210> SEQ ID NO 164
<211> LENGTH: 31
<212> TYPE: PRT
<213> ORGANISM: Homo sapiens

<400> SEQUENCE: 164

Asp Gly Glu Leu Ser Lys Cys Cys Met Cys Ser Asp Tyr Thr Ile Asp
 1               5                  10                  15

Cys Tyr Phe Pro Ile Ser Leu Pro Leu Leu Gly Arg Pro Tyr Tyr
            20                  25                  30

<210> SEQ ID NO 165
<211> LENGTH: 32
<212> TYPE: PRT
<213> ORGANISM: Homo sapiens

<400> SEQUENCE: 165

Leu Arg His Asn Ile Glu Ile Arg Pro Tyr Ile Asn His Thr Met Ala
 1               5                  10                  15

Ser Lys Gly Ser Ser Lys Arg Met Gly Cys Thr Ser Phe Thr Leu Thr
            20                  25                  30

<210> SEQ ID NO 166
<211> LENGTH: 28
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring
      L-amino acids

<400> SEQUENCE: 166

Gln Lys Leu Glu Ile Ile Ile Leu Ser Glu Lys Gly Met Trp Lys Ala
 1               5                  10                  15

Glu Ile Gly Gln Lys Leu Gly Xaa Leu His His Ser
            20                  25
```

<210> SEQ ID NO 167
<211> LENGTH: 14
<212> TYPE: PRT
<213> ORGANISM: Homo sapiens

<400> SEQUENCE: 167

Met Leu Cys Ile Asn Val Gln Thr His Val Tyr Glu Cys Ala
 1               5                  10

<210> SEQ ID NO 168
<211> LENGTH: 99
<212> TYPE: PRT
<213> ORGANISM: Homo sapiens

<400> SEQUENCE: 168

Leu Cys Cys Pro Gly Trp Ser Ala Val Val Arg Ser Trp Leu Thr Ala
 1               5                  10                  15

Thr Leu Ala Ser Trp Val Gln Ala Ile Leu Met Asp Ser Ala Ser Gln
            20                  25                  30

Val Ala Gly Ile Thr Ser Val His His Gln Ala Gln Leu Ser Phe Val
        35                  40                  45

Phe Leu Val Glu Met Gly Leu Cys His Val Gly Gln Ala Gly Leu Lys
    50                  55                  60

Leu Leu Ala Ser Ser Asp Leu Pro Ala Ser Ala Ser Gln Ser Ala Gly
65                  70                  75                  80

Ile Thr Gly Met Ser His His Ser Trp Pro Glu Arg Thr Ser Phe Ile
                85                  90                  95

Phe Lys Ile

<210> SEQ ID NO 169
<211> LENGTH: 32
<212> TYPE: PRT
<213> ORGANISM: Homo sapiens

<400> SEQUENCE: 169

Leu Cys Cys Pro Gly Trp Ser Ala Val Val Arg Ser Trp Leu Thr Ala
 1               5                  10                  15

Thr Leu Ala Ser Trp Val Gln Ala Ile Leu Met Asp Ser Ala Ser Gln
            20                  25                  30

<210> SEQ ID NO 170
<211> LENGTH: 35
<212> TYPE: PRT
<213> ORGANISM: Homo sapiens

<400> SEQUENCE: 170

Val Ala Gly Ile Thr Ser Val His His Gln Ala Gln Leu Ser Phe Val
 1               5                  10                  15

Phe Leu Val Glu Met Gly Leu Cys His Val Gly Gln Ala Gly Leu Lys
            20                  25                  30

Leu Leu Ala
        35

<210> SEQ ID NO 171
<211> LENGTH: 32
<212> TYPE: PRT
<213> ORGANISM: Homo sapiens

<400> SEQUENCE: 171

-continued

Ser Ser Asp Leu Pro Ala Ser Ala Ser Gln Ser Ala Gly Ile Thr Gly
 1               5                  10                  15

Met Ser His His Ser Trp Pro Glu Arg Thr Ser Phe Ile Phe Lys Ile
                20                  25                  30

<210> SEQ ID NO 172
<211> LENGTH: 282
<212> TYPE: PRT
<213> ORGANISM: Homo sapiens
<220> FEATURE:
<221> NAME/KEY: SITE
<222> LOCATION: (129)
<223> OTHER INFORMATION: Xaa equals any of the naturally occurring
      L-amino acids
<220> FEATURE:
<221> NAME/KEY: SITE
<222> LOCATION: (206)
<223> OTHER INFORMATION: Xaa equals any of the naturally occurring
      L-amino acids

<400> SEQUENCE: 172

Phe Gly Arg Gly Asn Thr Ile Leu Phe Leu Arg His Asn Lys Asp Leu
 1               5                  10                  15

Val Ala Gln Thr Ala Gln Pro Asp Gln Pro Asn Tyr Gly Phe Pro Leu
                20                  25                  30

Asp Leu Leu Arg Cys Glu Ser Leu Leu Gly Leu Asp Pro Ala Thr Cys
            35                  40                  45

Ser Arg Val Leu Asn Lys Asn Tyr Thr Leu Leu Val Ser Met Ala Pro
        50                  55                  60

Leu Thr Asn Glu Ile Arg Pro Val Ser Ser Cys Thr Pro Gln His Ile
65                  70                  75                  80

Gly Pro Ala Ile Pro Glu Val Ser Ser Val Trp Phe Lys Leu Tyr Ile
                85                  90                  95

Tyr His Val Thr Gly Gln Gly Pro Pro Ser Leu Leu Leu Ser Lys Gly
            100                 105                 110

Thr Arg Leu Arg Lys Leu Pro Asp Ile Phe Gln Ser Tyr Asp Arg Leu
        115                 120                 125

Xaa Ile Thr Ser Trp Gly His Asp Pro Gly Val Val Pro Thr Ser Asn
130                 135                 140

Val Leu Thr Met Leu Asn Asp Ala Leu Thr His Ser Ala Val Leu Ile
145                 150                 155                 160

Gln Gly His Gly Leu His Gly Ile Gly Glu Thr Val His Val Pro Phe
                165                 170                 175

Pro Phe Asp Glu Thr Glu Leu Gln Gly Glu Phe Thr Arg Val Asn Met
            180                 185                 190

Gly Val His Lys Ala Leu Gln Ile Leu Arg Asn Arg Val Xaa Leu Gln
        195                 200                 205

His Leu Cys Gly Tyr Val Thr Met Leu Asn Ala Ser Ser Gln Leu Ala
    210                 215                 220

Asp Arg Lys Leu Ser Asp Ala Ser Asp Glu Arg Gly Glu Pro Asp Leu
225                 230                 235                 240

Ala Ser Gly Ser Asp Val Asn Gly Ser Thr Glu Ser Phe Glu Met Val
                245                 250                 255

Ile Glu Glu Ala Thr Ile Asp Ser Ala Thr Lys Gln Thr Ser Gly Ala
            260                 265                 270

Thr Thr Glu Ala Asp Trp Val Pro Leu Val
        275                 280

```
<210> SEQ ID NO 173
<211> LENGTH: 175
<212> TYPE: PRT
<213> ORGANISM: Homo sapiens
<220> FEATURE:
<221> NAME/KEY: SITE
<222> LOCATION: (129)
<223> OTHER INFORMATION: Xaa equals any of the naturally occurring
      L-amino acids

<400> SEQUENCE: 173
```

Phe Gly Arg Gly Asn Thr Ile Leu Phe Leu Arg His Asn Lys Asp Leu
 1               5                  10                  15

Val Ala Gln Thr Ala Gln Pro Asp Gln Pro Asn Tyr Gly Phe Pro Leu
            20                  25                  30

Asp Leu Leu Arg Cys Glu Ser Leu Gly Leu Asp Pro Ala Thr Cys
        35                  40                  45

Ser Arg Val Leu Asn Lys Asn Tyr Thr Leu Leu Val Ser Met Ala Pro
    50                  55                  60

Leu Thr Asn Glu Ile Arg Pro Val Ser Ser Cys Thr Pro Gln His Ile
65                  70                  75                  80

Gly Pro Ala Ile Pro Glu Val Ser Ser Val Trp Phe Lys Leu Tyr Ile
                85                  90                  95

Tyr His Val Thr Gly Gln Gly Pro Pro Ser Leu Leu Ser Lys Gly
                100                 105                 110

Thr Arg Leu Arg Lys Leu Pro Asp Ile Phe Gln Ser Tyr Asp Arg Leu
            115                 120                 125

Xaa Ile Thr Ser Trp Gly His Asp Pro Gly Val Val Pro Thr Ser Asn
130                 135                 140

Val Leu Thr Met Leu Asn Asp Ala Leu Thr His Ser Ala Val Leu Ile
145                 150                 155                 160

Gln Gly His Gly Leu His Gly Ile Gly Glu Thr Val His Val Pro
                165                 170                 175

```
<210> SEQ ID NO 174
<211> LENGTH: 21
<212> TYPE: PRT
<213> ORGANISM: Homo sapiens

<400> SEQUENCE: 174
```

Leu Arg His Asn Lys Asp Leu Val Ala Gln Thr Ala Gln Pro Asp Gln
 1               5                  10                  15

Pro Asn Tyr Gly Phe
            20

```
<210> SEQ ID NO 175
<211> LENGTH: 21
<212> TYPE: PRT
<213> ORGANISM: Homo sapiens

<400> SEQUENCE: 175
```

Phe Pro Leu Asp Leu Leu Arg Cys Glu Ser Leu Leu Gly Leu Asp Pro
 1               5                  10                  15

Ala Thr Cys Ser Arg
            20

```
<210> SEQ ID NO 176
<211> LENGTH: 21
<212> TYPE: PRT
<213> ORGANISM: Homo sapiens
```

```
<400> SEQUENCE: 176

Arg Val Leu Asn Lys Asn Tyr Thr Leu Leu Val Ser Met Ala Pro Leu
 1               5                  10                  15

Thr Asn Glu Ile Arg
            20

<210> SEQ ID NO 177
<211> LENGTH: 20
<212> TYPE: PRT
<213> ORGANISM: Homo sapiens

<400> SEQUENCE: 177

Arg Pro Val Ser Ser Cys Thr Pro Gln His Ile Gly Pro Ala Ile Pro
 1               5                  10                  15

Glu Val Ser Ser
            20

<210> SEQ ID NO 178
<211> LENGTH: 21
<212> TYPE: PRT
<213> ORGANISM: Homo sapiens

<400> SEQUENCE: 178

Ser Val Trp Phe Lys Leu Tyr Ile Tyr His Val Thr Gly Gln Gly Pro
 1               5                  10                  15

Pro Ser Leu Leu Leu
            20

<210> SEQ ID NO 179
<211> LENGTH: 21
<212> TYPE: PRT
<213> ORGANISM: Homo sapiens
<220> FEATURE:
<221> NAME/KEY: SITE
<222> LOCATION: (21)
<223> OTHER INFORMATION: Xaa equals any of the naturally occurring
      L-amino acids

<400> SEQUENCE: 179

Leu Ser Lys Gly Thr Arg Leu Arg Lys Leu Pro Asp Ile Phe Gln Ser
 1               5                  10                  15

Tyr Asp Arg Leu Xaa
            20

<210> SEQ ID NO 180
<211> LENGTH: 20
<212> TYPE: PRT
<213> ORGANISM: Homo sapiens
<220> FEATURE:
<221> NAME/KEY: SITE
<222> LOCATION: (1)
<223> OTHER INFORMATION: Xaa equals any of the naturally occurring
      L-amino acids

<400> SEQUENCE: 180

Xaa Ile Thr Ser Trp Gly His Asp Pro Gly Val Val Pro Thr Ser Asn
 1               5                  10                  15

Val Leu Thr Met
            20

<210> SEQ ID NO 181
<211> LENGTH: 21
<212> TYPE: PRT
<213> ORGANISM: Homo sapiens
```

-continued

```
<400> SEQUENCE: 181

Met Leu Asn Asp Ala Leu Thr His Ser Ala Val Leu Ile Gln Gly His
  1               5                  10                  15

Gly Leu His Gly Ile
             20

<210> SEQ ID NO 182
<211> LENGTH: 107
<212> TYPE: PRT
<213> ORGANISM: Homo sapiens
<220> FEATURE:
<221> NAME/KEY: SITE
<222> LOCATION: (31)
<223> OTHER INFORMATION: Xaa equals any of the naturally occurring
      L-amino acids

<400> SEQUENCE: 182

Phe Pro Phe Asp Glu Thr Glu Leu Gln Gly Glu Phe Thr Arg Val Asn
  1               5                  10                  15

Met Gly Val His Lys Ala Leu Gln Ile Leu Arg Asn Arg Val Xaa Leu
             20                  25                  30

Gln His Leu Cys Gly Tyr Val Thr Met Leu Asn Ala Ser Ser Gln Leu
         35                  40                  45

Ala Asp Arg Lys Leu Ser Asp Ala Ser Asp Glu Arg Gly Glu Pro Asp
 50                  55                  60

Leu Ala Ser Gly Ser Asp Val Asn Gly Ser Thr Glu Ser Phe Glu Met
 65                  70                  75                  80

Val Ile Glu Glu Ala Thr Ile Asp Ser Ala Thr Lys Gln Thr Ser Gly
                 85                  90                  95

Ala Thr Thr Glu Ala Asp Trp Val Pro Leu Val
            100                 105

<210> SEQ ID NO 183
<211> LENGTH: 21
<212> TYPE: PRT
<213> ORGANISM: Homo sapiens

<400> SEQUENCE: 183

Gly Glu Phe Thr Arg Val Asn Met Gly Val His Lys Ala Leu Gln Ile
  1               5                  10                  15

Leu Arg Asn Arg Val
             20

<210> SEQ ID NO 184
<211> LENGTH: 20
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally occurring
      L-amino acids

<400> SEQUENCE: 184

Val Xaa Leu Gln His Leu Cys Gly Tyr Val Thr Met Leu Asn Ala Ser
  1               5                  10                  15

Ser Gln Leu Ala
             20

<210> SEQ ID NO 185
<211> LENGTH: 21
```

```
<212> TYPE: PRT
<213> ORGANISM: Homo sapiens

<400> SEQUENCE: 185

Ala Asp Arg Lys Leu Ser Asp Ala Ser Asp Glu Arg Gly Glu Pro Asp
 1               5                  10                  15

Leu Ala Ser Gly Ser
            20

<210> SEQ ID NO 186
<211> LENGTH: 21
<212> TYPE: PRT
<213> ORGANISM: Homo sapiens

<400> SEQUENCE: 186

Ser Asp Val Asn Gly Ser Thr Glu Ser Phe Glu Met Val Ile Glu Glu
 1               5                  10                  15

Ala Thr Ile Asp Ser
            20

<210> SEQ ID NO 187
<211> LENGTH: 11
<212> TYPE: PRT
<213> ORGANISM: Homo sapiens

<400> SEQUENCE: 187

Leu Arg Lys Leu His Ser Gln Thr Asn Pro Ile
 1               5                  10

<210> SEQ ID NO 188
<211> LENGTH: 16
<212> TYPE: PRT
<213> ORGANISM: Homo sapiens

<400> SEQUENCE: 188

Arg Asn Phe Tyr Leu Tyr Phe Leu Pro Tyr Cys Val Val Cys Val Cys
 1               5                  10                  15

<210> SEQ ID NO 189
<211> LENGTH: 31
<212> TYPE: PRT
<213> ORGANISM: Homo sapiens

<400> SEQUENCE: 189

Gly Thr Arg Ser Ile Asn Leu Leu Phe Phe Arg Cys Ile Leu Glu Gly
 1               5                  10                  15

Gly Lys Ser Val Glu Glu Gln Leu Cys Asn Ser Tyr Lys Phe Ser
            20                  25                  30

<210> SEQ ID NO 190
<211> LENGTH: 136
<212> TYPE: PRT
<213> ORGANISM: Homo sapiens
<220> FEATURE:
<221> NAME/KEY: SITE
<222> LOCATION: (42)
<223> OTHER INFORMATION: Xaa equals any of the naturally occurring
      L-amino acids
<220> FEATURE:
<221> NAME/KEY: SITE
<222> LOCATION: (67)
<223> OTHER INFORMATION: Xaa equals any of the naturally occurring
      L-amino acids
<220> FEATURE:
<221> NAME/KEY: SITE
<222> LOCATION: (121)
```

```
<223> OTHER INFORMATION: Xaa equals any of the naturally occurring
      L-amino acids
<220> FEATURE:
<221> NAME/KEY: SITE
<222> LOCATION: (126)
<223> OTHER INFORMATION: Xaa equals any of the naturally occurring
      L-amino acids
<220> FEATURE:
<221> NAME/KEY: SITE
<222> LOCATION: (134)
<223> OTHER INFORMATION: Xaa equals any of the naturally occurring
      L-amino acids

<400> SEQUENCE: 190

Leu Thr Val Pro Arg Arg Cys Pro Ala Ala Thr Glu Thr Asn Val Asp
  1               5                  10                  15

Gly Gln Lys Val Tyr Arg Asp Cys Ser Cys Ile Pro Gln Asn Leu Ser
             20                  25                  30

Ser Gly Phe Gly His Ala Thr Ala Gly Xaa Met His Phe Asn Leu Ser
         35                  40                  45

Glu Lys Ala Pro Pro Ser Gly Phe His Ile Arg Cys Glu Phe Ser Leu
     50                  55                  60

His Ser Xaa Ser Ser Ile Pro Ala Leu Thr Ala Thr Leu Arg Cys Val
 65                  70                  75                  80

Arg Asp Pro Gln Arg Ser Phe Ala Leu Gly Ile Gln Trp Ile Val Val
                 85                  90                  95

Arg Ile Leu Gly Gly Ile Pro Gly Pro Ile Ala Phe Gly Trp Val Ile
            100                 105                 110

Asp Lys Ala Cys Leu Leu Trp Gln Xaa Gln Cys Gly Gln Xaa Gly Ser
        115                 120                 125

Cys Leu Val Tyr Gln Xaa Arg Pro
        130                 135

<210> SEQ ID NO 191
<211> LENGTH: 14
<212> TYPE: PRT
<213> ORGANISM: Homo sapiens

<400> SEQUENCE: 191

Val Ser Leu Cys His Ala Gly Ala Leu Gln Pro Arg Arg Arg
  1               5                  10

<210> SEQ ID NO 192
<211> LENGTH: 21
<212> TYPE: PRT
<213> ORGANISM: Homo sapiens

<400> SEQUENCE: 192

Ala Thr Glu Thr Asn Val Asp Gly Gln Lys Val Tyr Arg Asp Cys Ser
  1               5                  10                  15

Cys Ile Pro Gln Asn
             20

<210> SEQ ID NO 193
<211> LENGTH: 21
<212> TYPE: PRT
<213> ORGANISM: Homo sapiens
<220> FEATURE:
<221> NAME/KEY: SITE
<222> LOCATION: (13)
<223> OTHER INFORMATION: Xaa equals any of the naturally occurring
      L-amino acids

<400> SEQUENCE: 193
```

```
Asn Leu Ser Ser Gly Phe Gly His Ala Thr Ala Gly Xaa Met His Phe
  1               5                  10                  15

Asn Leu Ser Glu Lys
             20

<210> SEQ ID NO 194
<211> LENGTH: 21
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring
      L-amino acids

<400> SEQUENCE: 194

Lys Ala Pro Pro Ser Gly Phe His Ile Arg Cys Glu Phe Ser Leu His
  1               5                  10                  15

Ser Xaa Ser Ser Ile
             20

<210> SEQ ID NO 195
<211> LENGTH: 20
<212> TYPE: PRT
<213> ORGANISM: Homo sapiens

<400> SEQUENCE: 195

Ile Pro Ala Leu Thr Ala Thr Leu Arg Cys Val Arg Asp Pro Gln Arg
  1               5                  10                  15

Ser Phe Ala Leu
             20

<210> SEQ ID NO 196
<211> LENGTH: 21
<212> TYPE: PRT
<213> ORGANISM: Homo sapiens

<400> SEQUENCE: 196

Leu Gly Ile Gln Trp Ile Val Val Arg Ile Leu Gly Gly Ile Pro Gly
  1               5                  10                  15

Pro Ile Ala Phe Gly
             20

<210> SEQ ID NO 197
<211> LENGTH: 15
<212> TYPE: PRT
<213> ORGANISM: Homo sapiens

<400> SEQUENCE: 197

Gly Thr Ala His Leu Pro Thr Leu His Trp Lys Pro Leu Leu Ser
  1               5                  10                  15

<210> SEQ ID NO 198
<211> LENGTH: 39
<212> TYPE: PRT
<213> ORGANISM: Homo sapiens

<400> SEQUENCE: 198

Leu Val Met Gln Cys Leu Gly Gln Val Leu Ser Pro Leu Arg Thr Ser
  1               5                  10                  15

Val Cys Leu Pro Ile Glu Arg Gly Arg Trp Pro Gly Met Val Pro His
                 20                  25                  30
```

-continued

```
Thr Thr Ser Ala Leu Gly Gly
        35

<210> SEQ ID NO 199
<211> LENGTH: 76
<212> TYPE: PRT
<213> ORGANISM: Homo sapiens

<400> SEQUENCE: 199

Gln Asn Thr Ile His Ser Leu Leu Pro Gln Gly Arg Met Thr Lys Ser
1               5                   10                  15

Leu Val Leu Glu Gln Lys Arg Lys Ala Gly Arg Ser Glu Met Lys
            20                  25                  30

Leu Glu Leu Leu Met Arg Val Ser Leu Trp Tyr Ser Gly Gln Ala Leu
        35                  40                  45

Val Leu Leu Gly Leu Ile Thr Asn Leu Ser Cys Ser Val Leu Gly Lys
    50                  55                  60

Ser Phe His Leu Ser Gly Pro Leu Ser Val Ser Leu
65                  70                  75

<210> SEQ ID NO 200
<211> LENGTH: 7
<212> TYPE: PRT
<213> ORGANISM: Homo sapiens

<400> SEQUENCE: 200

Glu Pro Ala Cys Leu Ser His
1               5

<210> SEQ ID NO 201
<211> LENGTH: 20
<212> TYPE: PRT
<213> ORGANISM: Homo sapiens

<400> SEQUENCE: 201

Arg Asp Phe Gly Cys Glu Pro Ser Pro Gly Thr Asp Thr Gly Ser Leu
1               5                   10                  15

Ser Phe Leu Val
            20

<210> SEQ ID NO 202
<211> LENGTH: 9
<212> TYPE: PRT
<213> ORGANISM: Homo sapiens

<400> SEQUENCE: 202

Ser Val Ile Leu Leu Cys Pro Phe Phe
1               5

<210> SEQ ID NO 203
<211> LENGTH: 9
<212> TYPE: PRT
<213> ORGANISM: Homo sapiens

<400> SEQUENCE: 203

Ala Arg Asp Arg Thr His Cys Leu Leu
1               5

<210> SEQ ID NO 204
<211> LENGTH: 10
<212> TYPE: PRT
<213> ORGANISM: Homo sapiens
```

```
<400> SEQUENCE: 204

Thr His Gln Thr Leu Ala Ala Thr Lys Gly
 1               5                  10

<210> SEQ ID NO 205
<211> LENGTH: 75
<212> TYPE: PRT
<213> ORGANISM: Homo sapiens

<400> SEQUENCE: 205

Met Pro Arg Pro Ser Pro Leu Ser Ser Pro Gly Ser Pro Val Thr Ser
 1               5                  10                  15

Gln Leu Cys Ser Pro Met Pro Ser Leu Asn Pro Ala Leu Pro Trp Gly
                20                  25                  30

Leu Leu Leu Ala Leu Pro Gly Leu Ser Leu His Thr Pro Phe Gln Thr
            35                  40                  45

Leu Thr Ala Ala Ser Pro His Gln Pro Ser Gly Asp Ser Ala Ala His
        50                  55                  60

Leu Ser Ala His Ser Phe Leu Leu Asp Ser His
65                  70                  75

<210> SEQ ID NO 206
<211> LENGTH: 13
<212> TYPE: PRT
<213> ORGANISM: Homo sapiens

<400> SEQUENCE: 206

Val Pro Cys Gly Thr Ala Cys Ser Val Gly Ala Ala Ala
 1               5                  10

<210> SEQ ID NO 207
<211> LENGTH: 39
<212> TYPE: PRT
<213> ORGANISM: Homo sapiens

<400> SEQUENCE: 207

Thr Ser Arg Ser Met Phe Phe Thr Ser Arg Pro Arg Thr Pro Trp Thr
 1               5                  10                  15

Ser Cys Leu Gln Ile Ala Pro Leu Ala Leu Leu Gln Ser Leu Gly Ile
                20                  25                  30

Trp Gln His Ser Ile Gly Ala
            35

<210> SEQ ID NO 208
<211> LENGTH: 35
<212> TYPE: PRT
<213> ORGANISM: Homo sapiens

<400> SEQUENCE: 208

Gly Thr Ala Gly Phe Ser Asp Leu Leu Leu Val Asn Val Met Cys Gln
 1               5                  10                  15

Thr Arg Arg Ser Ile Thr Phe Lys Asn Lys Leu Gln Lys Glu Ser Arg
                20                  25                  30

Ile Tyr Pro
        35

<210> SEQ ID NO 209
<211> LENGTH: 105
<212> TYPE: PRT
<213> ORGANISM: Homo sapiens
```

```
<400> SEQUENCE: 209

Pro Phe Arg Asn Ser Arg Val Arg Pro Lys Gly Ser Arg Asp Ala Leu
 1               5                  10                  15

Ser Trp Ser Ser Cys Thr Gly Pro Gln Pro Gly Thr Ser Ala Thr Val
            20                  25                  30

Gly Ser Leu Leu Cys Gly Gly Val Pro Cys Ile Ala Gly His Pro Ala
        35                  40                  45

Ala Ser Pro Ala Ser Cys Ser Val Pro Val Ala Pro His Pro Ala Val
    50                  55                  60

Val Thr Ala Gln Val Ser Arg Cys Ala Glu Cys Pro Leu Val Met Leu
65                  70                  75                  80

Arg Gly Thr Gly Val Leu Pro Pro Gly Phe Glu Arg Cys Leu Thr Pro
                85                  90                  95

Thr Ser Gly Val Ser Leu Pro Cys Val
            100                 105

<210> SEQ ID NO 210
<211> LENGTH: 55
<212> TYPE: PRT
<213> ORGANISM: Homo sapiens

<400> SEQUENCE: 210

Met Asp Thr Tyr Thr Phe Leu Ile Lys Ile Cys Lys Ile Phe Cys Ser
 1               5                  10                  15

Phe Leu Lys Cys His Ile Gln Val Cys Gly His Leu Leu Phe Leu Ile
            20                  25                  30

Phe Thr Ser Ile Lys Trp Ala Arg Lys Gln His His Cys Ser Arg Cys
        35                  40                  45

Lys Ala Ile Gly Leu Ser Ser
    50                  55

<210> SEQ ID NO 211
<211> LENGTH: 358
<212> TYPE: PRT
<213> ORGANISM: Homo sapiens
<220> FEATURE:
<221> NAME/KEY: SITE
<222> LOCATION: (83)
<223> OTHER INFORMATION: Xaa equals any of the naturally occurring
      L-amino acids

<400> SEQUENCE: 211

Asp Pro Arg Leu Ala Val Leu Leu Gly Val Gln Ile Leu Val Glu
 1               5                  10                  15

Arg Trp Arg Leu Gln Trp Asp His Tyr Tyr Leu Cys Pro His Arg Val
            20                  25                  30

Gln Ala Glu Glu Asp Val Glu Lys Ser Gln Trp Asn Tyr Pro Glu His
        35                  40                  45

Pro Gly Gly Asp Cys Leu Pro Gly Ala His His Leu Gln Lys His Pro
    50                  55                  60

Thr Pro Ser Pro Trp Leu Asp Gln Ala His His Trp Gln Ala Arg
65                  70                  75                  80

Pro Trp Xaa Pro Val Gln Gly His Arg Leu Cys Gly Arg Pro Gly Arg
                85                  90                  95

His Phe Gln Asn Gly Leu His Pro Lys Arg Trp Gln Trp Cys Gln Gly
            100                 105                 110

Val Gly Ser Val Gln Leu Pro Arg Ser Gly Val Gly Met Gly Met Tyr
        115                 120                 125
```

```
Asn Thr Asp Glu Ser Ile Ser Gly Phe Ala His Ser Cys Phe Gln Tyr
    130                 135                 140

Ala Ile Gln Lys Lys Trp Pro Leu Tyr Met Ser Thr Lys Asn Thr Ile
145                 150                 155                 160

Leu Lys Ala Tyr Asp Gly Arg Phe Lys Asp Ile Phe Gln Glu Ile Phe
                165                 170                 175

Asp Lys His Tyr Lys Thr Asp Phe Asp Lys Asn Lys Ile Trp Tyr Glu
                180                 185                 190

His Arg Leu Ile Asp Asp Met Val Ala Gln Val Leu Lys Ser Ser Gly
            195                 200                 205

Gly Phe Val Trp Ala Cys Lys Asn Tyr Asp Gly Asp Val Gln Ser Asp
    210                 215                 220

Ile Leu Ala Gln Gly Phe Gly Ser Leu Gly Leu Met Thr Ser Val Leu
225                 230                 235                 240

Val Cys Pro Asp Gly Lys Thr Ile Glu Ala Glu Ala Ala His Gly Thr
                245                 250                 255

Val Thr Arg His Tyr Arg Glu His Gln Lys Gly Arg Pro Thr Ser Thr
                260                 265                 270

Asn Pro Ile Ala Ser Ile Phe Ala Trp Thr Arg Gly Leu Glu His Arg
            275                 280                 285

Gly Lys Leu Asp Gly Asn Gln Asp Leu Ile Arg Phe Ala Gln Met Leu
    290                 295                 300

Glu Lys Val Cys Val Glu Thr Val Glu Ser Gly Ala Met Thr Lys Asp
305                 310                 315                 320

Leu Ala Gly Cys Ile His Gly Leu Ser Asn Val Lys Leu Asn Glu His
                325                 330                 335

Phe Leu Asn Thr Thr Asp Phe Leu Asp Thr Ile Lys Ser Asn Leu Asp
                340                 345                 350

Arg Ala Leu Gly Arg Gln
            355

<210> SEQ ID NO 212
<211> LENGTH: 48
<212> TYPE: PRT
<213> ORGANISM: Homo sapiens

<400> SEQUENCE: 212

Asp Pro Arg Leu Ala Val Leu Leu Gly Val Gln Ile Leu Val Leu Glu
1               5                   10                  15

Arg Trp Arg Leu Gln Trp Asp His Tyr Tyr Leu Cys Pro His Arg Val
                20                  25                  30

Gln Ala Glu Glu Asp Val Glu Lys Ser Gln Trp Asn Tyr Pro Glu His
            35                  40                  45

<210> SEQ ID NO 213
<211> LENGTH: 54
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids

<400> SEQUENCE: 213

Pro Gly Gly Asp Cys Leu Pro Gly Ala His His Leu Gln Lys His Pro
1               5                   10                  15
```

-continued

```
Thr Pro Ser Pro Trp Leu Asp Gln Ala His His Trp Gln Ala Arg
            20                  25                  30

Pro Trp Xaa Pro Val Gln Gly His Arg Leu Cys Gly Arg Pro Gly Arg
        35                  40                  45

His Phe Gln Asn Gly Leu
    50
```

<210> SEQ ID NO 214
<211> LENGTH: 70
<212> TYPE: PRT
<213> ORGANISM: Homo sapiens

<400> SEQUENCE: 214

```
His Pro Lys Arg Trp Gln Trp Cys Gln Gly Val Gly Ser Val Gln Leu
 1               5                  10                  15

Pro Arg Ser Gly Val Gly Met Gly Met Tyr Asn Thr Asp Glu Ser Ile
            20                  25                  30

Ser Gly Phe Ala His Ser Cys Phe Gln Tyr Ala Ile Gln Lys Lys Trp
        35                  40                  45

Pro Leu Tyr Met Ser Thr Lys Asn Thr Ile Leu Lys Ala Tyr Asp Gly
    50                  55                  60

Arg Phe Lys Asp Ile Phe
65                  70
```

<210> SEQ ID NO 215
<211> LENGTH: 70
<212> TYPE: PRT
<213> ORGANISM: Homo sapiens

<400> SEQUENCE: 215

```
Gln Glu Ile Phe Asp Lys His Tyr Lys Thr Asp Phe Asp Lys Asn Lys
 1               5                  10                  15

Ile Trp Tyr Glu His Arg Leu Ile Asp Asp Met Val Ala Gln Val Leu
            20                  25                  30

Lys Ser Ser Gly Gly Phe Val Trp Ala Cys Lys Asn Tyr Asp Gly Asp
        35                  40                  45

Val Gln Ser Asp Ile Leu Ala Gln Gly Phe Gly Ser Leu Gly Leu Met
    50                  55                  60

Thr Ser Val Leu Val Cys
65                  70
```

<210> SEQ ID NO 216
<211> LENGTH: 70
<212> TYPE: PRT
<213> ORGANISM: Homo sapiens

<400> SEQUENCE: 216

```
Pro Asp Gly Lys Thr Ile Glu Ala Glu Ala His Gly Thr Val Thr
 1               5                  10                  15

Arg His Tyr Arg Glu His Gln Lys Gly Arg Pro Thr Ser Thr Asn Pro
            20                  25                  30

Ile Ala Ser Ile Phe Ala Trp Thr Arg Gly Leu Glu His Arg Gly Lys
        35                  40                  45

Leu Asp Gly Asn Gln Asp Leu Ile Arg Phe Ala Gln Met Leu Glu Lys
    50                  55                  60

Val Cys Val Glu Thr Val
65                  70
```

```
<210> SEQ ID NO 217
<211> LENGTH: 46
<212> TYPE: PRT
<213> ORGANISM: Homo sapiens

<400> SEQUENCE: 217

Glu Ser Gly Ala Met Thr Lys Asp Leu Ala Gly Cys Ile His Gly Leu
 1               5                  10                  15

Ser Asn Val Lys Leu Asn Glu His Phe Leu Asn Thr Thr Asp Phe Leu
            20                  25                  30

Asp Thr Ile Lys Ser Asn Leu Asp Arg Ala Leu Gly Arg Gln
        35                  40                  45

<210> SEQ ID NO 218
<211> LENGTH: 67
<212> TYPE: PRT
<213> ORGANISM: Homo sapiens
<220> FEATURE:
<221> NAME/KEY: SITE
<222> LOCATION: (17)
<223> OTHER INFORMATION: Xaa equals any of the naturally occurring
      L-amino acids
<220> FEATURE:
<221> NAME/KEY: SITE
<222> LOCATION: (18)
<223> OTHER INFORMATION: Xaa equals any of the naturally occurring
      L-amino acids
<220> FEATURE:
<221> NAME/KEY: SITE
<222> LOCATION: (57)
<223> OTHER INFORMATION: Xaa equals any of the naturally occurring
      L-amino acids
<220> FEATURE:
<221> NAME/KEY: SITE
<222> LOCATION: (67)
<223> OTHER INFORMATION: Xaa equals any of the naturally occurring
      L-amino acids

<400> SEQUENCE: 218

Met Ile Met Gly Tyr Lys Ser Gln Lys Thr Phe Gly Leu Phe Asp Leu
 1               5                  10                  15

Xaa Xaa Val Lys Gly Lys Thr Ser Val Leu Glu Phe Asp Phe Trp Val
            20                  25                  30

Gln Ile Pro Val Ala Ser Leu Leu Ala Leu Trp Leu Asn Arg Leu Leu
        35                  40                  45

Asn Ser Val Lys Trp Ala Leu Lys Xaa Cys Val Ile His Ser Val Ala
    50                  55                  60

Val Asn Xaa
 65

<210> SEQ ID NO 219
<211> LENGTH: 68
<212> TYPE: PRT
<213> ORGANISM: Homo sapiens
<220> FEATURE:
<221> NAME/KEY: SITE
<222> LOCATION: (59)
<223> OTHER INFORMATION: Xaa equals any of the naturally occurring
      L-amino acids

<400> SEQUENCE: 219

Met Lys Ser Phe Pro Ser Thr Tyr Phe Lys Ser Ser Phe Gln Asn
 1               5                  10                  15

Thr Lys Tyr Gln Thr Gly Val Ile Ser Val Leu Ile Ser Tyr Glu Ile
            20                  25                  30

Glu Tyr Ala Ala Phe Tyr His Leu Ser Cys Lys Ile Thr Leu Pro Ser
```

```
                    35                  40                  45
Ser Val Ser Arg Asn Cys Phe Ile Ser Glu Xaa Leu Val Ala Ser Gln
        50                  55                  60
Cys Leu Asp Thr
 65
```